(12) United States Patent
Bretschneider et al.

(10) Patent No.: US 8,592,610 B2
(45) Date of Patent: *Nov. 26, 2013

(54) SPIROHETEROCYCLIC TETRONIC ACID DERIVATIVES

(75) Inventors: Thomas Bretschneider, Lohmar (DE); Reiner Fischer, Monheim (DE); Stefan Lehr, Liederbach (DE); Olga Malsam, Rosrath (DE); Arnd Voerste, Cologne (DE)

(73) Assignee: Bayer CropScience AG, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/616,437

(22) Filed: Sep. 14, 2012

(65) Prior Publication Data

US 2013/0012384 A1   Jan. 10, 2013

Related U.S. Application Data

(62) Division of application No. 12/783,236, filed on May 19, 2010, now Pat. No. 8,318,956.

(30) Foreign Application Priority Data

May 19, 2009   (EP) .................................. 09160634

(51) Int. Cl.
*C07D 307/00* (2006.01)
*C07D 215/00* (2006.01)

(52) U.S. Cl.
USPC ............................................. 549/319; 546/16

(58) Field of Classification Search
USPC ............................................. 549/319; 546/16
See application file for complete search history.

(56) References Cited

U.S. PATENT DOCUMENTS

| | | |
|---|---|---|
| 2,842,476 A | 7/1958 | Schreiber |
| 4,623,727 A | 11/1986 | Hübele |
| 4,639,266 A | 1/1987 | Heubach et al. |
| 4,844,734 A | 7/1989 | Iwasaki et al. |
| 4,881,966 A | 11/1989 | Nyffeler et al. |
| 4,888,049 A | 12/1989 | Iwasaki et al. |
| 4,891,057 A | 1/1990 | Sohn et al. |
| 4,902,340 A | 2/1990 | Hubele |
| 4,944,790 A | 7/1990 | Moser et al. |
| 5,013,659 A | 5/1991 | Bedbrook et al. |
| 5,094,681 A | 3/1992 | Krämer et al. |
| 5,215,570 A | 6/1993 | Burckhardt et al. |
| 5,262,383 A | 11/1993 | Fischer et al. |
| 5,314,863 A | 5/1994 | Löher et al. |
| 5,380,852 A | 1/1995 | Schütze et al. |
| 5,401,700 A | 3/1995 | Sohn et al. |
| 5,462,912 A | 10/1995 | Hioki et al. |
| 5,500,367 A | 3/1996 | Hain et al. |
| 5,516,750 A | 5/1996 | Willms et al. |
| 5,538,937 A | 7/1996 | Hasebe et al. |
| 5,610,122 A | 3/1997 | Fischer et al. |
| 5,689,046 A | 11/1997 | Schröder et al. |
| 5,700,758 A | 12/1997 | Rösch et al. |
| 5,705,476 A | 1/1998 | Hoffarth |
| 5,739,079 A | 4/1998 | Holdgrün et al. |
| 5,792,755 A | 8/1998 | Sagenmüller et al. |
| 5,830,825 A | 11/1998 | Fischer et al. |
| 5,830,826 A | 11/1998 | Fischer et al. |
| 5,972,839 A | 10/1999 | Ziemer et al. |
| 5,994,274 A | 11/1999 | Fischer et al. |
| 6,114,374 A | 9/2000 | Lieb et al. |
| 6,140,358 A | 10/2000 | Lieb et al. |
| 6,200,932 B1 | 3/2001 | Fischer et al. |
| 6,235,680 B1 | 5/2001 | Ziemer et al. |
| 6,251,827 B1 | 6/2001 | Ziemer et al. |

(Continued)

FOREIGN PATENT DOCUMENTS

| CA | 1 162 071 A1 | 2/1984 |
|---|---|---|
| CA | 2 671 179 A1 | 6/2008 |

(Continued)

OTHER PUBLICATIONS

Baur et al., 1997, Pesticide Science 51, 131-152.*
Baur, P., et al., "Polydisperse Ethoxylated Fatty Alcohol Surfactants as Accelerators of Cuticular Penetration. 1. Effects of Ethoxy Chain Length and the Size of the Penetrants," *Pestic. Sci.* 51:131-152, SCI, United Kingdom (1997).
Braun, H.-P., et al., "The general mitochondrial processing peptidase from potato is an integral part of cytochrome *c* reductase of the respiratory chain," *The Embo Journal* 11(9):3219-3227, Oxford University Press, United Kingdom (1992).
Campbell, A.C., et al., "Synthesis of (*E*)- and (*Z*)-Pulvinones," *Journal of the Chemical Society, Perkin Transactions* 1:1567-1576, Royal Society of Chemistry, United Kingdom (1985).
Christou, P., "Transformation technology," *Trends in Plant Science* 1(12): 423-431, Elsevier Science Ltd., United Kingdom (1996).

(Continued)

*Primary Examiner* — Nizal Chandrakumar
(74) *Attorney, Agent, or Firm* — Sterne, Kessler, Goldstein & Fox P.L.L.C.

(57) ABSTRACT

The present invention relates to novel compounds of the formula (I), (I)

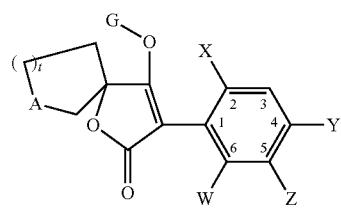

in which W, X, Y, Z, G, A and t have the meanings given above,
to a plurality of processes and intermediates for their preparation and to their use as pesticides and/or herbicides.
Moreover, the invention relates to selective herbicidal compositions comprising, firstly, the spiroheterocyclic tetronic acid derivates and, secondly, a crop plant compatibility-improving compound.
The present invention furthermore relates to increasing the activity of crop protection compositions comprising in particular phenyl-substituted bicyclooctane-1,3-dione derivates by adding ammonium salts or phosphonium salts and, if appropriate, penetrants, to the corresponding compositions, to processes for their preparation and to their use in crop protection as insecticides and/or acaricides and/or for preventing unwanted plant growth.

8 Claims, No Drawings

(56) References Cited

U.S. PATENT DOCUMENTS

| | | |
|---|---|---|
| 6,288,102 B1 | 9/2001 | Hagemann et al. |
| 6,316,486 B1 | 11/2001 | Lieb et al. |
| 6,358,887 B1 | 3/2002 | Fischer et al. |
| 6,451,843 B1 | 9/2002 | Lieb et al. |
| 6,458,965 B1 | 10/2002 | Lieb et al. |
| 6,589,976 B1 | 7/2003 | Fischer et al. |
| 6,602,823 B1 | 8/2003 | Röchling et al. |
| 6,645,914 B1 | 11/2003 | Woznica et al. |
| 6,861,391 B1 | 3/2005 | Fischer et al. |
| 6,894,005 B1 | 5/2005 | Maetzke et al. |
| 7,420,062 B2 * | 9/2008 | Fischer et al. ............ 548/363.1 |
| 8,318,956 B2 * | 11/2012 | Bretschneider et al. ...... 549/319 |
| 2003/0171219 A1 | 9/2003 | Lieb et al. |
| 2003/0216260 A1 | 11/2003 | Ruther et al. |
| 2003/0224939 A1 | 12/2003 | Miles |
| 2004/0127365 A1 | 7/2004 | Lieb et al. |
| 2004/0224844 A1 | 11/2004 | Bickers et al. |
| 2005/0009880 A1 | 1/2005 | Cottrell et al. |
| 2005/0037922 A1 | 2/2005 | Bickers et al. |
| 2005/0049145 A1 | 3/2005 | Bickers et al. |
| 2005/0096386 A1 | 5/2005 | Cottrell et al. |
| 2005/0256000 A1 | 11/2005 | Schaper et al. |
| 2006/0166829 A1 | 7/2006 | Fischer et al. |
| 2007/0015664 A1 | 1/2007 | Fischer et al. |
| 2007/0275858 A1 | 11/2007 | Fischer et al. |
| 2007/0298968 A1 | 12/2007 | Bretschneider et al. |
| 2008/0081807 A1 | 4/2008 | Lieb et al. |
| 2009/0209513 A1 | 8/2009 | Fischer et al. |
| 2009/0215624 A1 | 8/2009 | Fischer et al. |
| 2009/0227563 A1 | 9/2009 | Fischer et al. |
| 2009/0239906 A1 | 9/2009 | Fischer et al. |
| 2009/0298828 A1 | 12/2009 | Fischer et al. |
| 2009/0305891 A1 | 12/2009 | Fischer et al. |
| 2010/0004127 A1 | 1/2010 | Fischer et al. |
| 2010/0009850 A1 | 1/2010 | Fischer et al. |
| 2010/0168226 A1 | 7/2010 | Fischer et al. |
| 2010/0298145 A1 | 11/2010 | Bretschneider et al. |

FOREIGN PATENT DOCUMENTS

| | | |
|---|---|---|
| CA | 2 695 032 A1 | 2/2009 |
| CA | 2 700 292 A1 | 4/2009 |
| DE | 195 40 736 A1 | 6/1996 |
| EP | 0 142 924 A2 | 5/1985 |
| EP | 0 193 259 A1 | 9/1986 |
| EP | 0 221 044 A1 | 5/1987 |
| EP | 0 242 236 A1 | 10/1987 |
| EP | 0 242 246 A1 | 10/1987 |
| EP | 0 257 993 A2 | 3/1988 |
| EP | 0 346 620 A1 | 12/1989 |
| EP | 0 453 086 A2 | 10/1991 |
| JP | 60-87254 A | 5/1985 |
| WO | WO 84/02919 | 8/1984 |
| WO | WO 91/13972 A1 | 9/1991 |
| WO | WO 91/19806 A1 | 12/1991 |
| WO | WO 92/00377 A1 | 1/1992 |
| WO | WO 92/11376 A1 | 7/1992 |
| WO | WO 92/14827 A1 | 9/1992 |
| WO | WO 92/16108 A1 | 10/1992 |
| WO | WO 95/17817 * | 6/1995 |
| WO | WO 95/17817 A1 | 7/1995 |
| WO | WO 96/33270 A1 | 10/1996 |
| WO | WO 98/13361 A1 | 4/1998 |
| WO | WO 98/35553 A1 | 8/1998 |
| WO | WO 98/38856 A1 | 9/1998 |
| WO | WO 02/34048 A1 | 5/2002 |
| WO | WO 2007/023719 A1 | 3/2007 |
| WO | WO 2007/023764 A1 | 3/2007 |
| WO | WO 2007/024782 A2 | 3/2007 |
| WO | WO 2007/027777 A2 | 3/2007 |
| WO | WO 2009/049851 A1 | 4/2009 |
| ZA | 9805601 | 1/1999 |

OTHER PUBLICATIONS

Freyer, J.D., & Evans, S.A., "Weed Control Handbook," 5th Ed. Blackwell Scientific Publications, S. 101-103, United Kingdom (1968).

Klingman, G.C., "5. Surface Active Agents," in Weed Control as a Science: 81-91, John Wiley and Sons, Inc., New York, United States (1961).

Perry, J.H., Chemical Engineers' Handbook, 4th Ed., McGraw-Hill Book Company, Inc., S.8-57, United States (1973).

Sonnewald, U., et al., "Transgenic tobacco plants expressing yeast-derived invertase in either the cytosol, vacuole or apoplast: a powerful tool for studying sucrose metabolism and sink/source interactions," *The Plant Journal* 1(1):95-106, Wiley-Blackwell in association with the Society for Experimental Biology, United Kingdom (1991).

Sonntag, N.O.V., "The Reactions of Aliphatic Acid Chlorides," *Chemical Reviews* 52: 237-416, American Chemical Society, United States, (1953).

Wolter, F.P., et al., "*rbcS* genes in *Solanum tuberosum*: Conservation of transit peptide and exon shuffling during evolution," *Proc. Natl. Acad. Sci.* 85:846-850, National Academy of Sciences of the United States of America, United States (1988).

http://www.lifesci.susses.ac.uk/Home/Neil_Crichmore/Bt/, (accessed Sep. 29, 2010).

English language Abstract of European Patent Publication No. EP 0 346 620 A1, European Patent Office, espacenet database—Worldwide (1989).

English language Abstract of Japanese Patent Publication No. JP 60-087254 A, Japanese Patent Office, Patent & Utility Model Gazette DB, Patent Abstract of Japan (1985).

English language Abstract of WIPO Patent Publication No. WO 2007/023719 A1, European Patent Office, espacenet database—Worldwide (2007).

English language Abstract of WIPO Patent Publication No. WO 2007/023764 A1, European Patent Office, espacenet database—Worldwide (2007).

English language translation of DE 195 40 736 A1.

* cited by examiner

SPIROHETEROCYCLIC TETRONIC ACID DERIVATIVES

This is a divisional application of application Ser. No. 12/783,236, filed May 19, 2010, which claims priority to EP 091606343, filed May 19, 2009, each of which is wholly incorporated by reference herein.

The present invention relates to novel spiroheterocyclic tetronic acid derivatives, to a plurality of processes for their preparation and to their use as pesticides and/or herbicides. The invention also provides selective herbicidal compositions comprising, firstly, the spiroheterocyclic tetronic acid derivatives and, secondly, a crop plant compatibility-improving compound.

The present invention furthermore relates to increasing the activity of crop protection compositions comprising in particular spiroheterocyclic tetronic acid derivatives by adding ammonium salts or phosphonium salts and, if appropriate, penetrants, to the corresponding compositions, to processes for their preparation and to their use in crop protection as insecticides and/or for preventing unwanted plant growth.

It is known that certain substituted $\Delta^3$-dihydrofuran-2-one derivatives have herbicidal properties (cf. DE-A-4 014 420). The synthesis of the tetronic acid derivatives used as starting material (such as, for example, 3-(2-methylphenyl)-4-hydroxy-5-(4-fluorophenyl)-$\Delta^3$-dihydrofuran-2-one) is also described in DE-A-4 014 420. Compounds of a similar structure—without any stated insecticidal and/or acaricidal activity—are known from the publication Campbell et al, J. Chem. Soc., Perkin Trans. 1, 1985, (8) 1567-76. Moreover, 3-aryl-$\Delta^3$-dihydrofuranone derivatives having herbicidal, acaricidal and insecticidal properties are known from: EP-A-528 156, EP-A-647 637, WO 95/26 954, WO 96/20 196, WO 96/25 395, WO 96/35 664, WO 97/01 535, WO 97/02 243, WO 97/36 868, WO 98/05 638, WO 98/06 721, WO 99/16 748, WO 98/25 928, WO 99/43 649, WO 99/48 869, WO 99/55 673, WO 01/23354, WO 01/74 770, WO 01/17 972, WO 04/024 688, WO 04/080 962, WO 04/111 042, WO 05/092 897, WO 06/000 355, WO 06/029 799, WO 07/048,545, WO 07/073,856, WO 07/096,058, WO 07/121,868, WO 07/140, 881, WO 08/067,911, WO 08/083,950, WO 09/015,801, WO 09/039,975. WO 09/049,851 discloses spiroheterocyclic pyrrolidinediones having an oxo substituent.

This invention now provides novel compounds of the formula (I)

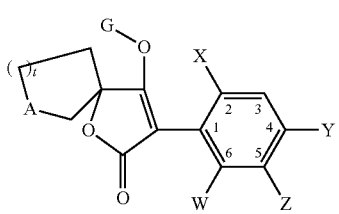

in which

W represents hydrogen, halogen, alkyl, alkenyl, alkynyl, optionally substituted cycloalkyl, alkoxy, alkenyloxy, haloalkyl, haloalkoxy or cyano, X represents halogen, alkyl, alkenyl, alkynyl, optionally substituted cycloalkyl, alkoxy, alkenyloxy, alkylthio, alkylsulphinyl, alkylsulphonyl, haloalkyl, haloalkoxy, haloalkenyloxy, nitro or cyano, Y and Z independently of one another represent hydrogen, alkyl, alkenyl, alkynyl, optionally substituted cycloalkyl, alkoxy, halogen, haloalkyl, haloalkoxy, cyano, nitro or in each case optionally substituted aryl or hetaryl, A represents

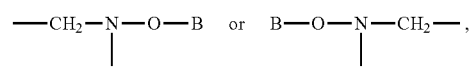

B represents hydrogen, alkyl, haloalkyl, alkoxylalkyl, alkoxylalkoxyalkyl, represents in each case optionally substituted alkenyl, alkynyl, represents cycloalkylalkyl which is optionally interrupted by heteroatoms, represents phenylalkyl, hetarylalkyl or represents a latentiating group from G, t represents the number 0 or 1, G represents hydrogen (a) or represents one of the groups

in which

E represents a metal ion or an ammonium ion,

L represents oxygen or sulphur,

M represents oxygen or sulphur, $R^1$ represents in each case optionally halogen- or cyano-substituted alkyl, alkenyl, alkoxy-allyl, alkylthioalkyl or polyalkoxyalkyl or represents in each case optionally halogen-, alkyl- or alkoxy-substituted cycloalkyl or heterocyclyl or represents in each case optionally substituted phenyl, phenylalkyl, hetaryl, phenoxyalkyl or hetaryloxyalkyl, $R^2$ represents in each case optionally halogen- or cyano-substituted alkyl, alkenyl, alkoxyalkyl or polyalkoxyalkyl or represents in each case optionally substituted cycloalkyl, phenyl or benzyl, $R^3$, $R^4$ and $R^5$ independently of one another represent in each case optionally halogen-substituted alkyl, alkoxy, alkylamino, dialkylamino, alkylthio, alkenylthio or cycloalkylthio or represent in each case optionally substituted phenyl, benzyl, phenoxy or phenylthio, $R^6$ and $R^7$ independently of one another represent hydrogen, in each case optionally halogen- or cyano-substituted alkyl, cycloalkyl, alkenyl, alkoxy, alkoxyalkyl, in each case optionally substituted phenyl or benzyl, or together with the nitrogen atom to which they are attached form an optionally substituted cycle which optionally contains oxygen or sulphur.

The latentiating groups G are selected to allow their removal by one or a combination of biochemical, chemical or physical processes to afford compounds of the formula (I) in which G represents hydrogen. Examples of these processes include enzymatic cleavage, chemical hydrolysis and photolysis. Compounds carrying such groups G may offer certain advantages, such as improved penetration of the cuticles of the plants treated, increased tolerance of crops, improved compatibility or stability in formulated mixtures containing other herbicides, herbicide safeners, plant growth regulators, fungicides or insecticides, or reduce leaching into the soil.

Depending inter alia on the nature of the substituents, the compounds of the formula (I) may be present as geometric and/or optical isomers or isomer mixtures of varying composition which, if appropriate, may be separated in a customary manner. The present invention provides both the pure isomers and the isomer mixtures, their preparation and use and compositions comprising them. However, for the sake of simplicity, hereinbelow only compounds of the formula (I) are referred to, although what is meant is both the pure compounds and, if appropriate, mixtures having various proportions of isomeric compounds.

Including the different meanings (a), (b), (c), (d), (e), (f) and (g) of group G, the following principle structures (I-a) to (I-g) result:

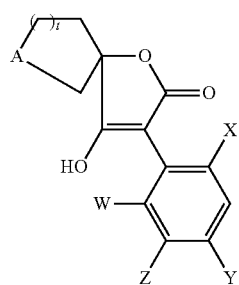

(I-a)

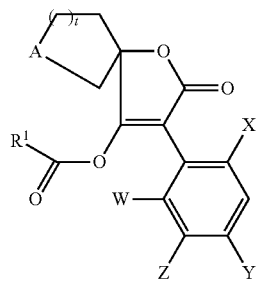

(I-b)

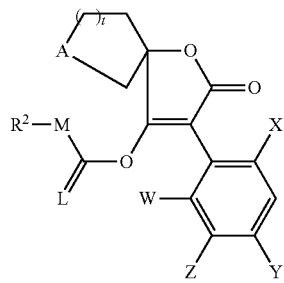

(I-c)

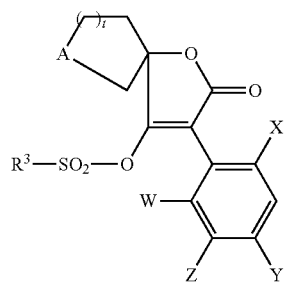

(I-d)

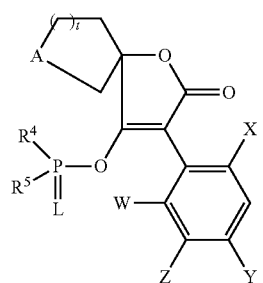

(I-e)

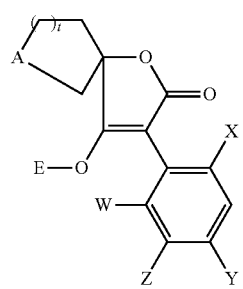

(I-f)

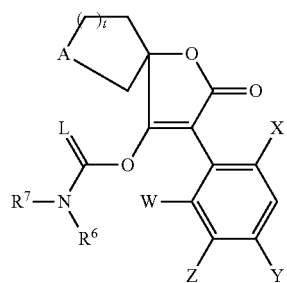

(I-g)

in which
A, E, L, M, W, X, Y, Z, t, $R^1$, $R^2$, $R^3$, $R^4$, $R^5$, $R^6$ and $R^7$ have the meanings given above.

Furthermore, it has been found that the novel compounds of the formula (I) are obtained by one of the processes described below:

(A) Compounds of the formula (I-a)

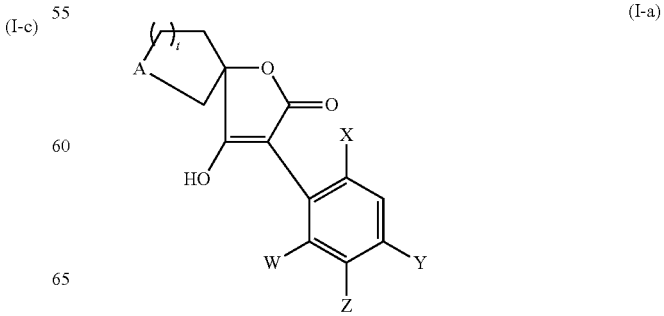

(I-a)

in which
A, t, W, X, Y and Z have the meaning given above
are obtained when
compounds of the formula (II)

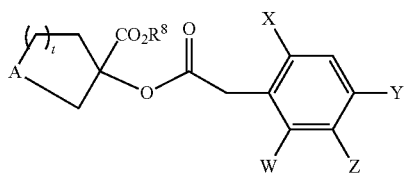

in which
A, t, W, X, Y and Z have the meanings given above,
and
$R^8$ represents alkyl (preferably $C_1$-$C_6$-alkyl),
are condensed intramolecularly in the presence of a diluent and in the presence of a base.

Moreover, it has been found
(B) that the compounds of the formula (I-b) shown above in which $R^1$, A, t, W, X, Y and Z have the meanings given above are obtained when compounds of the formula (I-a) shown above in which A, t, W, X, Y and Z have the meanings given above are in each case reacted
α) with compounds of the formula (III)

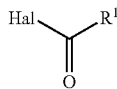

in which
$R^1$ has the meaning given above and
Hal represents halogen (in particular chlorine or bromine)
or
β) with carboxylic anhydrides of the formula (IV)

$$R^1\text{—CO—O—CO—}R^1 \qquad (IV)$$

in which
$R^1$ has the meaning given above,
if appropriate in the presence of a diluent and if appropriate in the presence of an acid binder;
(C) that the compounds of the formula (I-c) shown above in which $R^2$, A, t, M, W, X, Y and Z have the meanings given above and L represents oxygen are obtained when compounds of the formula (I-a) shown above in which A, t, W, X, Y and Z have the meanings given above are in each case reacted
with chloroformic esters or chloroformic thio esters of the formula (V)

$$R^2\text{-M-CO—Cl} \qquad (V)$$

in which
$R^2$ and M have the meanings given above,
if appropriate in the presence of a diluent and if appropriate in the presence of an acid binder;
(D) that compounds of the formula (I-c) shown above in which $R^2$, A, t, M, W, X, Y and Z have the meanings given above and L represents sulphur are obtained when compounds of the formula (I-a) shown above in which A, t, W, X, Y and Z have the meanings given above are in each case reacted
with chloromonothioformic esters or chlorodithioformic esters of the formula (VII)

in which
M and $R^2$ have the meanings given above,
if appropriate in the presence of a diluent and if appropriate in the presence of an acid binder,
(E) that compounds of the formula (I-d) shown above in which $R^3$, A, t, W, X, Y and Z have the meanings given above are obtained when compounds of the formula (I-a) shown above in which A, t, W, X, Y and Z have the meanings given above are in each case reacted
with sulphonyl chlorides of the formula (VII)

$$R^3\text{—}SO_2\text{—Cl} \qquad (VII)$$

in which
$R^3$ has the meaning given above,
if appropriate in the presence of a diluent and if appropriate in the presence of an acid binder,
(F) that compounds of the formula (Fe) shown above in which L, $R^4$, $R^5$, A, t, W, X, Y and Z have the meanings given above are obtained when compounds of the formula (I-a) shown above in which A, t, W, X, Y and Z have the meanings given above are in each case reacted
with phosphorus compounds of the formula (VII)

in which
F, $R^4$ and $R^5$ have the meanings given above and
Hal represents halogen (in particular chlorine or bromine),
if appropriate in the presence of a diluent and if appropriate in the presence of an acid binder,
(G) that compounds of the formula (I-f) shown above in which F, A, t, W, X, and Z have the meanings given above are obtained when compounds of the formula (I-a) in which A, t, W, X, V and Z have the meanings given above are in each case reacted
with metal compounds or amines of the formulae (IX) and (X) respectively,

in which
Me represents a mono- or divalent metal (preferably an alkali or alkaline earth metal such as lithium, sodium, potassium, magnesium or calcium),
t represents the number 1 or 2 and $R^{10}$, $R^{11}$, $R^{12}$ independently of one another represent hydrogen or alkyl (preferably $C_1$-$C_8$-alkyl), if appropriate in the presence of a diluent, (H) that compounds of the formula (I-g) shown above in which L, $R^6$, $R^7$, A, t, W, X, Y and Z have the meanings given above are obtained when compounds of the formula (I-a) shown above in which A, t, W, X, Y and Z have the meanings given above are in each case reacted α) with isocyanates or isothiocyanates of the formula (XI)

   (XI)

which $R^6$ and L have the meanings given above, if appropriate in the presence of a diluent and if appropriate in the presence of a catalyst, or β) with carbamoyl chlorides or thiocarbamoyl chlorides of the formula (XII)

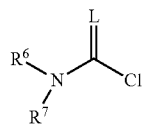   (XII)

in which

L, $R^6$ and $R^7$ have the meanings given above, if appropriate in the presence of a diluent and if appropriate in the presence of an acid binder, (Iα) that compounds of the formulae (I-a) to (I-g) shown above in which A, t, G, W, X, Y and Z have the meaning given above are obtained when compounds of the formulae (I-a') to (I-g') in which A, t, G, W, X and Y have the meaning given above and Z' preferably represents bromine or iodine

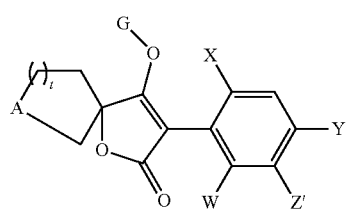   (I-a' to I-g')

and (Jβ) that compounds of the formulae (I-a) to (I-g) shown above in which A, t, G, W, X, Y and Z have the meaning given above are obtained when compounds of the formulae (I-a") to (I-g") in which A, t, G, W, X and Z have the meaning given above and Y' preferably represents bromine or iodine

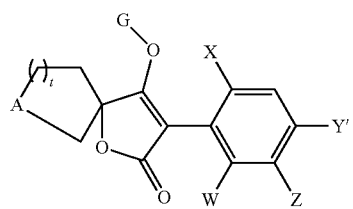   (I-a" to I-g")

are coupled with (het)aryl derivatives suitable for coupling, for example phenylboronic acids of the formulae (XIIIα) and (XIIIβ)

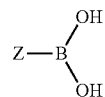   (XIIIα)

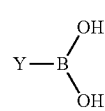   (XIIIβ)

or esters thereof, in the presence of a solvent, in the presence of a catalyst (for example Pd complexes) and in presence the of a base (for example sodium carbonate, potassium phosphate).

Furthermore, it has been found that the novel compounds of the formula (I) are very effective as pesticides, preferably as insecticides, acaricides and herbicides.

Surprisingly, it has now also been found that certain substituted cyclic ketoenoles, when used together with the crop plant compatibility-improving compounds (safener/antidotes) described below, efficiently prevent damage to the crop plants and can be used in a particularly advantageous manner as broad-spectrum combination preparations for the selective control of unwanted plants in crops of useful plants, such as, for example, in cereals, but also in maize, potatoes, soya beans and rice.

The invention also provides selective herbicidal compositions comprising an effective amount of an active compound combination comprising, as components, a') at least one compound of the formula (I), in which A, t, G, W, X, Y and Z have the meaning given above and (b') at least one crop plant compatibility-improving compound (safener).

The safeners are preferably selected from the group consisting of:

S1) Compounds of the formula (S1)

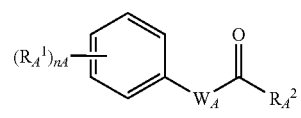   (S1)

where the symbols and indices have the following meanings:

$n_A$ is a natural number from 0 to 5, preferably from 0 to 3;

$R_A^1$ is halogen, ($C_1$-$C_4$)-alkyl, ($C_1$-$C_4$)-alkoxy, nitro or ($C_1$-$C_4$)-haloalkyl;

$W_A$ is an unsubstituted or substituted divalent heterocyclic radical from the group consisting of partially unsaturated or aromatic five-membered heterocycles having 1 to 3 hetero ring atoms from the group consisting of N and O, where at least one nitrogen atom and at most one oxygen atom is present in the ring, preferably a radical from the group consisting of ($W_A^1$) to ($W_A^4$),

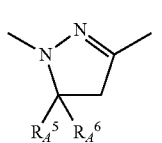  ($W_A^1$)

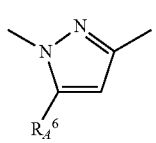  ($W_A^2$)

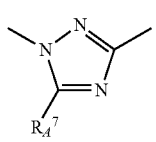  ($W_A^3$)

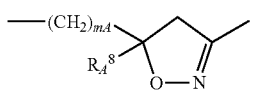  ($W_A^4$)

$m_A$ is 0 or 1;

$R_A^2$ is $OR_A^3$, $SR_A^3$ or $NR_A^3R_A^4$ or a saturated or unsaturated 3- to 7-membered heterocycle having at least one nitrogen atom and up to 3 heteroatoms, preferably from the group consisting of O and S, which is attached via the nitrogen atom to the carbonyl group in (S1) and which is unsubstituted or substituted by radicals from the group consisting of ($C_1$-$C_4$)-alkyl, ($C_1$-$C_4$)-alkoxy and optionally substituted phenyl, preferably a radical of the formula $OR_A^3$, $NHR_A^4$ or $N(CH_3)_2$, in particular of the formula $OR_A^3$;

$R_A^3$ is hydrogen or an unsubstituted or substituted aliphatic hydrocarbon radical having preferably a total of 1 to 18 carbon atoms;

$R_A^4$ is hydrogen, ($C_1$-$C_6$)-alkyl, ($C_1$-$C_6$)-alkoxy or substituted or unsubstituted phenyl;

$R_A^5$ is H, ($C_1$-$C_8$)-alkyl, ($C_1$-$C_8$)-haloalkyl, ($C_1$-$C_4$)-alkoxy-($C_1$-$C_8$)-alkyl, cyano or $COOR_A^9$ where $R_A^9$ is hydrogen, ($C_1$-$C_8$)-alkyl, ($C_1$-$C_8$)-haloalkyl, ($C_1$-$C_4$)-alkoxy-($C_1$-$C_4$)-alkyl, ($C_1$-$C_6$)-hydroxyallyl, ($C_3$-$C_{12}$)-cycloalkyl or tri-($C_1$-$C_4$)-alkylsilyl;

$R_A^6$, $R_A^7$, $R_A^8$ are identical or different and are hydrogen, ($C_1$-$C_8$)-alkyl, ($C_1$-$C_8$)-haloalkyl, ($C_3$-$C_{12}$)-cycloalkyl or substituted or unsubstituted phenyl;

preferably:

a) compounds of the type of the dichlorophenylpyrazoline-3-carboxylic acid ($S1^a$), preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds, as described in WO-A-91/07874;

b) derivatives of dichlorophenylpyrazolecarboxylic acid ($S1^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4) and related compounds, as described in EP-A-333 131 and EP-A-269 806;

c) derivatives of 1,5-diphenylpyrazole-3-carboxylic acid ($S1^c$), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds, as described, for example, in EP-A-268554;

d) compounds of the type of the triazolecarboxylic acids ($S1^d$), preferably compounds such as fenchlorazole(-ethyl), i.e. ethyl 1-(2,4-dichlorophenyl)-5-trichloromethyl-(1H)-1,2,4-triazole-3-carboxylate (S1-7), and related compounds, as described in EP-A-174 562 and EP-A-346 620;

e) compounds of the type of the 5-benzyl- or 5-phenyl-2-isoxazoline-3-carboxylic acid or the 5,5-diphenyl-2-isoxazoline-3-carboxylic acid ($S1^e$), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds, as described in WO-A-91/08202, or 5,5-diphenyl-2-isoxazolinecarboxylic acid (S1-10) or ethyl 5,5-diphenyl-2-isoxazolinecarboxylate (S1-11) ("isoxadifen-ethyl") or n-propyl 5,5-diphenyl-2-isoxazolinecarboxylate (S1-12) or ethyl 5-(4-fluorophenyl)-5-phenyl-2-isoxazoline-3-carboxylate (S1-13), as described in the patent application WO-A-95/07897.

S2) Quinoline derivatives of the formula (S2)

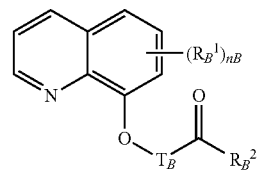  (S2)

where the symbols and indices have the following meanings:

$R_B^1$ is halogen, ($C_1$-$C_4$)-alkyl, ($C_1$-$C_4$)-alkoxy, nitro or ($C_1$-$C_4$)-haloalkyl;

$n_B$ is a natural number from 0 to 5, preferably from 0 to 3;

$R_B^2$ is $OR_B^3$, $SR_B^3$ or $NR_B^3R_B^4$ or a saturated or unsaturated 3- to 7-membered heterocycle having at least one nitrogen atom and up to 3 heteroatoms, preferably from the group consisting of O and S, which is attached via the nitrogen atom to the carbonyl group in (S2) and which is unsubstituted or substituted by radicals from the group consisting of ($C_1$-$C_4$)-alkyl, ($C_1$-$C_4$)-alkoxy and optionally substituted phenyl, preferably a radical of the formula $OR_B^3$;

$R_6^3$ is hydrogen or an unsubstituted or substituted aliphatic hydrocarbon radical having preferably a total of 1 to 18 carbon atoms;

$R_B^4$ is hydrogen, ($C_1$-$C_6$)-alkyl, ($C_1$-$C_6$)-alkoxy or substituted or unsubstituted phenyl;

$T_B$ is a ($C_1$- or $C_2$)-alkanediyl chart which is unsubstituted or substituted by one or two ($C_1$-$C_4$)-alkyl radicals or by [($C_1$-$C_3$)-alkoxyl]carbonyl;

preferably:

a) compounds of the type of the 8-quinolinoxyacetic acid ($S2^a$), preferably 1-methylhexyl (5-chloro-8-quinolinoxy)acetate ("cloquintocet-mexyl") (S2-1), 1,3-dimethyl-but-1-yl (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (82-5), methyl (5-chloro-8-quinolinoxy)acetate (82-6), allyl (5-chloro-8-quinolinoxy)acetate (82-7), 2-(2-propylideneiminoxy)-1-ethyl (5-chloro-8-quinolinoxy)acetate (S2-8), 2-oxo-prop-1-yl (5-chloro-8-quinolinoxy)acetate (S2-9) and related compounds, as described in EP-A-86 750, EP-A-94 349 and EP-A-191 736 or EP-A-0 492 366, and also (5-chloro-8-quinolinoxy)acetic acid (S2-10), its hydrates and salts, for example its lithium, sodium, potassium, calcium, magnesium, aluminium, iron, ammonium, quaternary ammonium, sulphonium or phosphonium salts, as described in WO-A-2002/34048;
b) compounds of the type of the (5-chloro-8-quinolinoxy) malonic acid (S2$^b$), preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds, as described in EP-A-0 582 198.

S3) Compounds of the formula (S3)

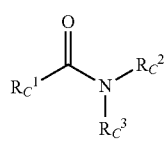

where the symbols and indices have the following meanings:
$R_C^1$ is $(C_1-C_4)$-alkyl, $(C_1-C_4)$-haloalkyl, $(C_1-C_4)$-alkenyl, $(C_2-C_4)$-haloalkenyl, $(C_3-C_7)$-cycloalkyl, preferably dichloromethyl;
$R_C^2$, $R_C^3$ are identical or different and are hydrogen, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_1-C_4)$-alkylcarbomyl-$(C_1-C_4)$-alkyl, $(C_2-C_4)$-alkenylcarbamoyl-$(C_1-C_4)$-allyl, $(C_1-C_4)$-alkoxy-$(C_1-C_4)$-alkyl, dioxolanyl-$(C_1-C_4)$-alkyl, thiazolyl, fury), furylalkyl, thienyl, piperidyl, substituted or unsubstituted phenyl, or $R_C^2$ and $R_C^3$ together form a substituted or unsubstituted heterocyclic ring, preferably an oxazolidine, thiazohdine, piperidine, morpholine, hexahydropyrimidine or benzoxazine ring;
preferably:
active compounds of the type of the dichloroacetamides which are frequently used as pre-emergence safeners (soil-acting safeners), such as, for example,
"dichlormid" (N,N-diallyl-2,2-dichloroacetamide) (83-1),
"R-29148" (3-dichloroacetyl-2,2,5-trimethyl-1,3-oxazolidine) from Stauffer (S3-21
"R-28725" (3-dichloroacetyl-2,2-dimethyl-1,3-oxazolidine) from Stauffer (83-3),
"benoxacor" (4-dichloroacetyl-3,4-dihydro-3-methyl-2H-1,4-benzoxazine) (S3-4),
"PPQ-1292" (N-allyl-N-[(1,3-dioxolan-2-yl)methyl] dichloroacetamide) from PPG industries (S3-5),
"DKA-24" (N-allyl-N-[(allylaminocarbonyl)methyl] dichloroacetamide) from Sagro-Chem (S3-6),
"AD-67" or "MON 4660" (3-dichloroacetyl-1-oxa-3-azaspiror[4,5]decane) from Nitrokemia or Monsanto (S3-7),
"TT-35" (1-dichloroacetazepane) from TRI-Chemical RT (S3-8)
"diclonon" (dicyclonon) "BAS145138" or "LAB145138" (83-9) (3-dichloroacetyl-2,5,5-trimethyl-1,3-diazabicyclo[4.3.0]nonane) from BASF,
"furilazole" or "MON 13900" ((RS)-3-dichloroacetyl-5-(2-furyl)-2,2-dimethyloxazolidine) (S3-10) and also its (R)-isomer (S3-11).

S4) N-Acylsulphonamides of the formula (S4) and their salts

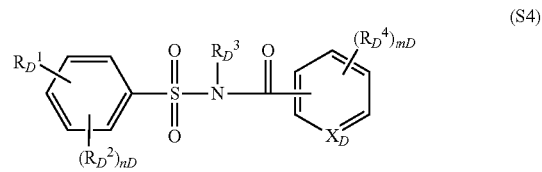

where the symbols and indices have the following meanings:
$X_D$ is CH or N;
$R_D^1$ is CO—$NR_D^5R_D^6$ or NHCO—$R_D^7$;
$R_D^2$ is halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulphonyl, $(C_1-C_4)$-alkoxycarbonyl or $(C_1-C_4)$-alkylcarbonyl;
$R_D^3$ is hydrogen, $(C_1-C_4)$-alkyl, $(C_2-C_4)$-alkenyl or $(C_2-C_4)$-alkynyl;
$R_D^4$ is halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkyl, cyano, $(C_1-C_4)$-alkylthio, sulphinyl, $(C_1-C_4)$-alkylsulphonyl, $(C_1-C_4)$-alkoxycarbonyl or $(C_1-C_4)$-alkylcarbonyl;
$R_D^5$ is hydrogen, $(C_1-C_6)$-alkyl, $(C_3-C_6)$-cycloalkyl, $(C_2-C_5)$-alkenyl, $(C_2-C_5)$-alkynyl, $(C_5-C_6)$-cycloalkenyl, phenyl or 3- to 6-membered heterocyclyl which contains $v_D$ heteroatoms from the group consisting of nitrogen, oxygen and sulphur, where the seven last-mentioned radicals are substituted by $v_D$ substituents from the group consisting of halogen, $(C_1-C_6)$-alkoxy, $(C_1-C_6)$-haloalkoxy, $(C_1-C_2)$-alkylsulphinyl, $(C_1-C_2)$-alkylsulphonyl, $(C_3-C_6)$-cycloalkyl, $(C_1-C_4)$-alkoxycarbonyl, $(C_1-C_4)$-alkylcarbonyl and phenyl and, in the case of cyclic radicals, also $(C_1-C_4)$-alkyl and $(C_1-C_4)$-haloalkyl;
$R_D^6$ is hydrogen, $(C_1-C_6)$-alkyl, $(C_2-C_5)$-alkenyl or $(C_2-C_6)$-alkynyl, where the three last-mentioned radicals are substituted by $v_D$ radicals from the group consisting of halogen, hydroxy, $(C_1-C_4)$-alkyl, $(C_1-C_4)$-alkoxy and $(C_1-C_4)$-alkylthio, or
$R_D^5$ and $R_D^6$ together with the nitrogen atom carrying them form a pyrrolidinyl or piperidinyl radical;
$R_D^7$ is hydrogen, $(C_1-C_4)$-alkylamino, di-$(C_1-C_4)$-alkylamino, $(C_1-C_6)$-alkyl, $(C_3-C_6)$-cycloalkyl, where the 2 last-mentioned radicals are substituted by $v_D$ substituents from the group consisting of halogen, $(C_1-C_4)$-alkoxy, halo-$(C_1-C_6)$-alkoxy and $(C_1-C_4)$-alkylthio and, in the case of cyclic radicals, also $(C_1-C_4)$-alkyl and $(C_1-C_4)$-haloalkyl;
$n_D$ is 0, 1 or 2;
$m_D$ is 1 or 2;
$v_D$ is 0, 1, 2 or 3;
from among these, preference is given to compounds of the type of the N-acylsulphonamides, for example of the formula (S4$^a$) below, which are known, for example, from WO-A-97/45016

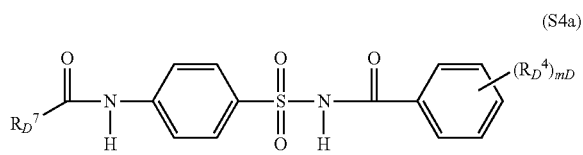

(S4a)

in which
- $R_D^7$ is $(C_1$-$C_6)$-alkyl, $(C_3$-$C_6)$-cycloalkyl, where the 2 last-mentioned radicals are substituted by $v_D$ substituents from the group consisting of halogen, $(C_1$-$C_4)$-alkoxy, halo-$(C_1$-$C_6)$-alkoxy and $(C_1$-$C_4)$-alkylthio and, in the case of cyclic radicals, also $(C_1$-$C_6)$-alkyl and $(C_1$-$C_4)$-haloalkyl;
- $R_D^4$) is halogen, $(C_1$-$C_4)$-alkyl, $(C_1$-$C_4)$-alkoxy, $CF_3$;
- $m_D$ 1 or 2;
- $v_D$ is 0, 1, 2 or 3;

and also
acylsulphamoylbenzamides, for example of the formula (S4$^b$) below, which are known, for example, from WO-A-99116744,

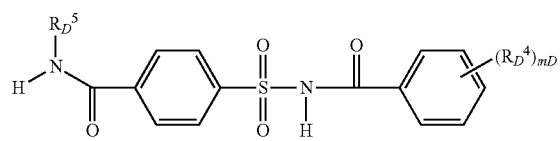

(S4b)

for example those in which
- $R_D^5$=cyclopropyl and $(R_D^4)$=2-OMe ("cyprosulfamide", S4-1),
- $R_D^5$=cyclopropyl and $(R_D^4)$=5-Cl-2-OMe (S4-2),
- $R_D^5$=ethyl and $(R_D^4)$=2-OMe (S4-3),
- $R_D^5$=isopropyl and $(R_D^4)$ 5-Cl-2-OMe (S4-4) and
- $R_D^5$ isopropyl and $(R_D^4)$=2-OMe (S4-5)

and also
compounds of the type of the N-acylsulphamoylphenylureas of the formula (S4$^c$), which are known, for example, from EP-A-365484,

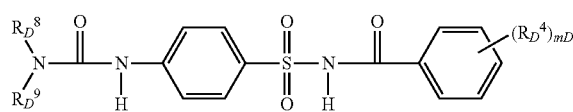

(S4c)

in which
- $R_D^8$ and $R_D^9$ independently of one another are hydrogen, $(C_1$-$C_8)$-alkyl, $(C_3$-$C_6)$-alkenyl, $(C_3$-$C_6)$-alkynyl,
- $R_D^4$ is halogen, $(C_1$-$C_4)$-alkyl, $(C_1$-$C_4)$-alkoxy, $CF_3$,
- $m_D$ is 1 or 2;

for example
1-[4-(N-2-methoxybenzoylsulphamoyl)phenyl]-3-methylurea,
1-[4-(N-2-methoxybenzoylsulphamoyl)phenyl]-3-dimethylurea,
1-[4-(N-4,5-dimethylbenzoylsulphamoyl)phenyl]-3-methylurea.

S5) Active compounds from the class of the hydroxyaromatics and aromatic-aliphatic carboxylic acid derivatives (S5), for example ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicylic acid, 2-hydroxycinnamic acid, 1,2-dihydro-2-oxo-6-trifluoromethylpyridine-3-carboxamide, 2,4-dichlorocinnamic acid, as described in WO-A-2004/084631, WO-A-2005/015994, WO-A-2005/016001.

S6) Active compounds from the class of the 1,2-dihydroquinoxalin-2-ones (S6), for example 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-[2-(diethylamino)ethyl]-6,7-dimethyl-3-thiophen-2-ylquinoxalin-2(1H)-one, 1-(2-methylsulphonylaminoethyl)-3-(2-thienyl)-1,2-dihydroquinoxalin-2-one, as described in WO-A-2005/112630.

S7) Compounds of the formula (S7), as described in WO-A-1998/38856,

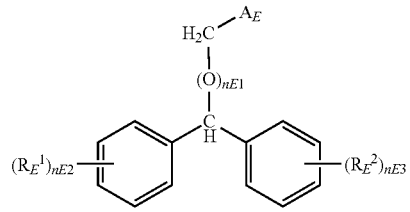

(S7)

where the symbols and indices have the following meanings:
- $R_E^1$, $R_E^2$ independently of one another are halogen, $(C_1$-$C_4)$-alkyl, $(C_1$-$C_4)$-alkoxy, $(C_1$-$C_4)$-haloalkyl, $(C_1$-$C_4)$-alkylamino, di-$(C_1$-$C_4)$-alkylamino, nitro;
- $A_E$ is $COOR_E^3$ or $COSR_E^4$
- $R_E^3$, $R_E^4$ independently of one another are hydrogen, $(C_1$-$C_4)$-alkyl, $(C_2$-$C_6)$-alkenyl, $(C_2$-$C_4)$-alkynyl, cyanoalkyl, $(C_1$-$C_4)$-haloalkyl, phenyl, nitrophenyl, benzyl, halobenzyl, pyridinylalkyl or alkylammonium,
- $n_E^1$ is 0 or 1;
- $n_E^2$, $n_E^3$ independently of one another are 0, 1 or 2, preferably:
- diphenylmethoxyacetic acid,
- ethyl diphenylmethoxyacetate,
- methyl diphenylmethoxyacetate (CAS Reg. No.: 41858-19-9) (S7-1).

S8) Compounds of the formula (S8), as described in WO-A-98/27049,

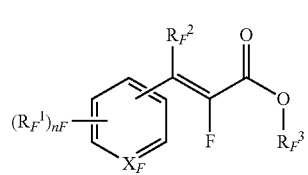

(S8)

in which
- $X_F$ is CH or N,
- $n_F$ is, if $X_F$=N, an integer from 0 to 4 and is, if $X_F$=CH, an integer from 0 to 5,
- $R_F^1$ is halogen, $(C_1$-$C_4)$-alkyl, $(C_1$-$C_4)$-haloalkyl, $(C_1$-$C_4)$-alkoxy, $(C_1$-$C_4)$-haloalkoxy, nitro, $(C_1$-$C_4)$-alkylthio, ($C_1$-$C_4$)-alkylsulphonyl, ($C_1$-$C_4$)-alkoxycarbonyl, optionally substituted phenyl, optionally substituted phenoxy, $R_F^2$ is hydrogen or ($C_1$-$C_4$)-alkyl, $R_F^3$ is hydrogen, ($C_1$-$C_8$)-alkyl, ($C_2$-$C_4$)-alkenyl, ($C_7$-$C_4$)-alkynyl or aryl, where each of the carbon-containing radicals mentioned above is unsubstituted or substituted by one or more, preferably by up to three, identical or different radicals from the group consisting of halogen and alkoxy; or salts thereof, preferably compounds in which $X_F$ is CH, $n_F$ is an integer from 0 to 2, $R_F^1$ is halogen, ($C_1$-$C_4$)-alkyl, ($C_1$-$C_4$)-haloalkyl, ($C_1$-$C_4$)-alkoxy, ($C_1$-$C_4$)-haloalkoxy, $R_F^2$ is hydrogen or ($C_1$-$C_4$)-alkyl, $R_F^3$ is hydrogen, ($C_1$-$C_8$)-alkyl, ($C_2$-$C_4$)-alkenyl, ($C_2$-$C_4$)-alkynyl or aryl, where each of the carbon-containing radicals mentioned above is unsubstituted or substituted by one or more, preferably by up to three, identical or different radicals from the group consisting of halogen and alkoxy; or salts thereof, S9) Active compounds from the class of the 3-(5-tetrazolylcarbonyl)-2-quinolones (S9), for example
1,2-dihydro-4-hydroxy-1-ethyl-3-(5-tetrazolylcarbonyl)-2-quinolone (CAS Reg. No.: 219479-18-2), 1,2-dihydro-4-hydroxy-1-methyl-3-(5-tetrazolylcarbonyl)-2-quinolone (CAS Reg. No.; 95855-00-8), as described in WO-A-1999/000020.

S10) Compounds of the formula (S10$^a$) or (S10$^b$) as described in WO-A-2007/023719 and WO-A-2007/023764

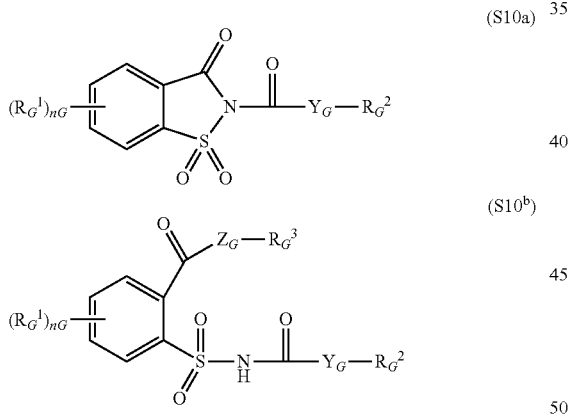

(S10a)

(S10b)

in which $R_G^1$ is halogen, ($C_1$-$C_4$)-alkyl, methoxy, nitro, cyano, $CF_3$, $OCF_3$ $Y_G$, $Z_G$ independently of one another are O or S, $n_G$ is an integer from 0 to 4, $R_G^2$ is ($C_1$-$C_{16}$)-alkyl, ($C_2$-$C_6$)-alkenyl, ($C_3$-$C_6$)-cycloalkyl, aryl; benzyl, halobenzyl, $R_G^3$ is hydrogen or ($C_1$-$C_6$)-alkyl.

S11) Active compounds of the type of the oxyimino compounds (S11), which are known as seed dressings, such as, for example, "oxabetrinil" ((Z)-1,3-dioxolan-2-ylmethoxyimino(phenyl)acetonitrile) (S11-1), which is known as seed dressing safener for millet against metolachlor damage, "fluxofenim" (1-(4-chlorophenyl)-2,2,2-trifluoro-1-ethanone O-(1,3-dioxolan-2-ylmethyl)oxime) (S11-2), which is known as seed dressing safener for millet against metolachlor damage, and "cyometrinil" or "CGA-43089" ((Z)-cyanomethoxyimino(phenyl)acetonitrile) (S11-3), which is known as seed dressing safener for millet against metolachlor damage.

S12) Active compounds from the class of the isothiochromanones (S12), such as, for example, methyl[(3-oxo-1H-2-benzothiopyran-4(3H)-ylidene)methoxy]acetate (CAS Reg. No.: 205121-04-6) (S12-1) and related compounds from WO-A-1998/13361.

S13) One or more compounds from group (S13):

"naphthalic anhydride" (1,8-naphthalenedicarboxylic anhydride) (S13-1), which is known as seed dressing safener for corn against thiocarbamate herbicide damage, "fenclorim" (4,6-dichloro-2-phenylpyrimidine) (S13-2), which is known as safener for pretilachlor in sown rice, "flurazole" (benzyl 2-chloro-4-trifluoromethyl-1,3-thiazole-5-carboxylate) (S13-3), which is known as seed dressing safener for millet against alachlor and metolachlor damage, "CL-304415" (CAS Reg. No.: 31541-57-8) (4-carboxy-3,4-dihydro-2H-1-benzopyran-4-acetic acid) (S13-4) from American Cyanamid, which is known as safener for corn against imidazolinone damage, "MG-191" (CAS Reg. No.: 96420-72-3) (2-dichloromethyl-2-methyl-1,3-dioxolane) (S13-5) from Nitrokemia, which is known as safener for corn, "MG-838" (CAS Reg. No.: 133993-74-5) (2-propenyl 1-oxa-4-azaspiro[4.5]decane-4-carbodithioate) (S13-6) from Nitrokemia, "disulfoton" (O,O-diethyl S-2-ethylthioethyl phosphorodithioate) (S13-7), "dietholate" (O,O-diethyl (1)-phenyl phosphorothioate) (S13-8), "mephenate" (4-chlorophenyl methylcarbamate) (S13-5).

S14) Active compounds which, besides a herbicidal effect against harmful plants, also have a safener effect on crop plants such as rice, such as, for example, "dimepiperate" or "MY-93" (S-1-phenylethyl piperidine-1-carbothioate), which is known as safener for rice against molinate herbicide damage, "daimuron" or "SK 23" (1-(1-methyl-1-phenylethyl)-3-p-tolylurea), which is known as safener for rice against imazosulphuron herbicide damage, "curnyluron"="JC-940" (3-(2-chlorophenylmethyl)-1-(1-methyl-1-phenyl-ethyl)urea, see JP-A-60087254), which is known as safener for rice against some herbicide damage, "methoxyphenone" or "NK 049" (3,3'-dimethyl-4-methoxybenzophenone), which is known as safener for rice against some herbicide damage, "CSB" (1-bromo-4-(chloromethylsulphortyl)benzene) from Kumiai, (CAS Reg. No. 54091-05-4), which is known as safener against some herbicide damage in rice.

S15) Active compounds which are primarily used as herbicides, but also have safener effect on crop plants, for example (2,4-dichlorophenoxy)acetic acid (2,4-D), (4-chlorophenoxy)acetic acid, (R,S)-2-(4-chloro-o-tolyloxy)propionic acid (mecoprop), 4-(2,4-dichlorophenoxy)butyric acid (2,4-DB), (4-chloro-o-tolyloxy)acetic acid (MCPA), 4-(4-chloro-o-tolyloxy)butyric acid, 4-(4-chlorophenoxy)butyric acid, 1,6-dichloro-2-methoxybenzoic acid (dicamba), 1-(ethoxycarbonyl)ethyl 3,6-dichloro-2-methoxybenzoate (lactidichlor-ethyl).

Most preferred crop plant compatibility-improving compounds [components (b')] are cloquintocet-mexyl, fenchlorazole-ethyl, isoxadifen-ethyl, mefenpyr-diethyl, fenclorim, cumyluron, S4-1 and S4-5, and particular emphasis is given to mefenpyr-diethyl. Emphasis is likewise given to cyprosulfamide (S4-1), and also to cloquintocet-mexyl.

Surprisingly, it has now been found that the above-defined active compound combinations of compounds of the general formula (I) and safeners (antidotes) of group (b') listed above, whilst being tolerated very well by crop plants, have particularly high herbicidal activity and can be used in various crops, in particular in cereal (especially wheat), but also in soya beans, potatoes, maize and rice, for the selective control of weeds.

Here, it has to be considered to be surprising that, from a large number of known safeners or antidotes which are capable of antagonizing the damaging effect of a herbicide on the crop plants, it is in particular the abovementioned compounds of group (b') which neutralize the damaging effect of substituted aryl ketones on the crop plants virtually completely without negatively affecting the herbicidal activity with respect to the weeds.

Emphasis is given here to the particularly advantageous effect of the particularly and most preferred combination partners from group (b'), in particular in respect of sparing cereal plants, such as, for example, wheat, barley and rye, but also maize and rice, as crop plants.

The formula (I) provides a general definition of the compounds according to the invention. Preferred substituents or ranges of the radicals given in the formula above and below are illustrated below:

W preferably represents hydrogen, halogen, $C_1$-$C_6$-alkyl, $C_2$-$C_6$-alkenyl, $C_2$-$C_6$-alkynyl, represents $C_3$-$C_6$-cycloalkyl which is optionally mono- or disubstituted by $C_1$-$C_2$-allyl, $C_1$-$C_2$-alkoxy, fluorine, chlorine, trifluoromethyl or $C_3$-$C_6$-cycloalkyl, represents $C_1$-$C_6$-alkoxy, $C_1$-$C_4$-haloalkyl, $C_1$-$C_4$-haloalkoxy or cyano, X preferably represents halogen, $C_1$-$C_6$-alkyl, $C_2$-$C_6$-alkenyl, $C_2$-$C_6$-alkynyl, represents $C_3$-$C_6$-cycloalkyl which is optionally mono- or disubstituted by $C_1$-$C_2$-alkyl, $C_1$-$C_2$-alkoxy, fluorine, chlorine, trifluoromethyl or $C_3$-$C_6$-cycloallyl, represents $C_1$-$C_6$-haloalkyl, $C_1$-$C_6$-alkoxy, $C_3$-$C_6$-alkenyloxy, $C_1$-$C_6$-alkylthio, $C_1$-$C_6$-alkylsulfinyl, $C_1$-$C_6$-alkylsulfonyl, $C_1$-$C_6$-haloalkoxy, $C_3$-$C_6$-haloalkenyloxy, nitro or cyano, Y and Z independently of one another preferably represent hydrogen, halogen, $C_1$-$C_6$-alkyl, $C_2$-$C_6$-alkenyl, $C_2$-$C_6$-alkynyl, represent $C_3$-$C_6$-cycloalkyl which is optionally mono- or disubstituted by $C_1$-$C_2$-alkyl, $C_1$-$C_2$-alkoxy, fluorine, chlorine, trifluoromethyl or $C_3$-$C_6$-cycloalkyl, represent $C_1$-$C_6$-alkoxy, $C_1$-$C_6$-haloalkyl, $C_1$-$C_6$-haloalkoxy, cyano, $C_2$-$C_6$-alkenyl, $C_2$-$C_6$-alkynyl or represent one of the (het)aryl radicals

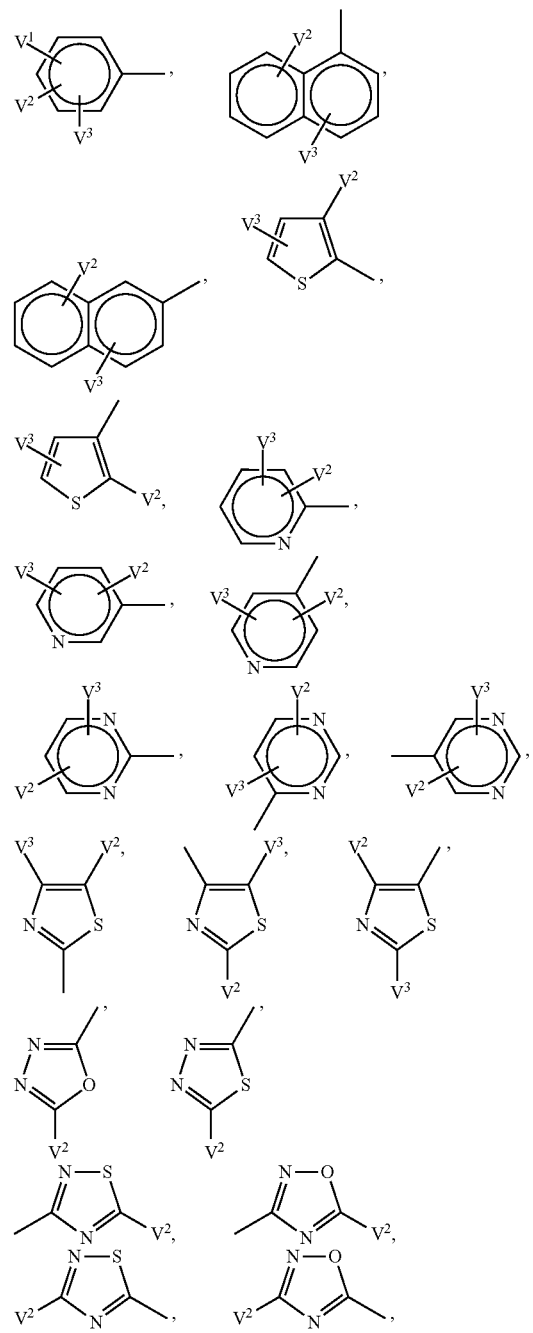

where in the case of (het)aryl only one of the radicals Y or Z may represent (het)aryl, $V^1$ preferably represents hydrogen, halogen, $C_1$-$C_{12}$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_1$-$C_4$-haloalkoxy, nitro, cyano or represents phenyl, phenoxy, phenoxy-$C_1$-$C_4$-alkyl, phenyl-$C_1$-$C_4$-alkoxy, phenylthio-$C_1$-$C_4$-alkyl or phenyl-$C_1$-$C_4$-alkylthio, each of which is optionally monosubstituted of polysubstituted by halogen, $C_1$-$C_6$-alkyl, $C_1$-$C_6$-alkoxy, $C_1$-$C_4$-haloalkyl, $C_1$-$C_4$-haloalkoxy, nitro or cyano, $V^2$ and $V^3$ stehen preferably independently of one another represent hydrogen, halogen, $C_1$-$C_6$-alkyl, $C_1$-$C_6$-alkoxy, $C_1$-$C_4$-haloalkyl or $C_1$-$C_4$-haloalkoxy, A preferably represents

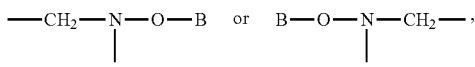

B preferably represents hydrogen, $C_1$-$C_6$-alkyl, $C_1$-$C_6$-haloalkyl, $C_1$-$C_4$-alkoxy-$C_1$-$C_4$-alkoxy-$C_1$-$C_4$-alkoxy-$C_1$-$C_4$-alkyl, represents in each case optionally halogen-substituted $C_3$-$C_6$-alkenyl, $C_3$-$C_6$-alkynyl, represents in each case optionally substituted phenyl-$C_1$-$C_4$-alkyl, heteroaryl-$C_1$-$C_4$-alkyl or $C_3$-$C_6$-cycloalkyl-$C_1$-$C_4$-alkyl which may optionally be interrupted by heteroatoms or represents a latentiating group from G, t preferably represents the number 0 or 1, G preferably represents hydrogen (a) or represents one of the groups

 (b)

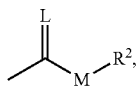 (c)

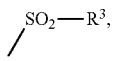 (d)

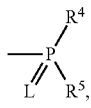 (e)

E, or (f)

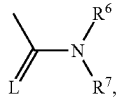 (g)

in which

E represents a metal ion or an ammonium ion,

L represents oxygen or sulphur and

M represents oxygen or sulphur, $R^1$ preferably represents in each case optionally halogen- or cyano-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl or poly-$C_1$-$C_8$-alkoxy-$C_1$-$C_8$-alkyl or represents optionally halogen-, $C_1$-$C_6$-alkyl- or $C_1$-$C_6$-alkoxy-substituted $C_3$-$C_8$-cycloalkyl in which optionally one or two not directly adjacent methylene groups are replaced by oxygen and/or sulphur, represents phenyl which is optionally substituted by halogen, cyano, nitro, $C_1$-$C_6$-alkyl, $C_1$-$C_6$-alkoxy, $C_1$-$C_6$-haloalkyl, $C_1$-$C_6$-haloalkoxy, $C_1$-$C_6$-alkylthio or $C_1$-$C_6$-alkyl-sulphonyl, represents phenyl-$C_1$-$C_6$-alkyl which is optionally substituted by halogen, nitro, cyano, $C_1$-$C_6$-alkyl, $C_1$-$C_6$-alkoxy, $C_1$-$C_6$-haloalkyl or $C_1$-$C_6$-haloalkoxy, represents optionally halogen- or $C_1$-$C_6$-alkyl-substituted 5- or 6-membered hetaryl having one or two heteroatoms from the group consisting of oxygen, sulphur and nitrogen, represents phenoxy-$C_1$-$C_6$-alkyl which is optionally substituted by halogen or $C_1$-$C_6$-alkyl or represents optionally halogen-, amino- or $C_1$-$C_6$-alkyl-substituted 5- or 6-membered hetaryloxy-$C_1$-$C_6$-alkyl having one or two heteroatoms from the group consisting of oxygen, sulphur and nitrogen, $R^2$ preferably represents in each case optionally halogen- or cyano-substituted $C_1$-$C_{20}$-alkyl, $C_2$-$C_{20}$-alkenyl, $C_1$-$C_8$-alkoxy-$C_2$-$C_8$-alkyl or poly-$C_1$-$C_8$-alkoxy-$C_2$-$C_8$-alkyl, represents $C_3$-$C_8$-cycloalkyl which is optionally substituted by halogen, $C_1$-$C_6$-alkyl or $C_1$-$C_6$-alkoxy, or represents in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl, $R^3$ preferably represents optionally halogen-substituted $C_1$-$C_8$-alkyl or in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl, $R^4$ and $R^5$ independently of one another represent in each case optionally halogen-substituted $C_1$-$C_8$-alkyl, $C_1$-$C_8$-alkoxy, $C_1$-$C_8$-alkylamino, di-($C_1$-$C_8$-alkyl)amino, $C_1$-$C_8$-allylthio or $C_3$-$C_8$-alkenylthio or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio, $R^6$ and $R^7$ independently of one another represent hydrogen, represent in each case optionally halogen- or cyano-substituted $C_1$-$C_8$-alkyl, $C_3$-$C_8$-cycloalkyl, $C_1$-$C_8$-alkoxy, $C_3$-$C_8$-alkenyl or $C_1$-$C_8$-alkoxy-$C_2$-$C_8$-alkyl, represent in each case optionally halogen-, $C_1$-$C_8$-alkyl-, $C_1$-$C_8$-haloalkyl- or $C_1$-$C_8$-alkoxy-substituted phenyl or benzyl or together represent an optionally $C_1$-$C_6$-alkyl-substituted $C_3$-$C_6$-alkylene radical in which optionally one methylene group is replaced by oxygen or sulphur.

In the radical definitions mentioned as being preferred, halogen represents fluorine, chlorine, bromine and iodine, in particular fluorine, chlorine and bromine.

W particularly preferably represents hydrogen, chlorine, bromine, $C_1$-$C_4$-alkyl, $C_2$-$C_4$-alkenyl, $C_2$-$C_4$-alkynyl, represents $C_3$-$C_6$-cycloalkyl which is optionally monosubstituted by methyl, ethyl, methoxy, fluorine, chlorine, trifluoromethyl or cyclopropyl, represents $C_1$-$C_4$-alkoxy, $C_1$-$C_2$-haloalkyl or $C_1$-$C_2$-haloalkoxy, X particularly preferably represents chlorine, bromine, $C_1$-$C_4$-alkyl, $C_2$-$C_4$-alkenyl, $C_2$-$C_4$-alkynyl, represents $C_3$-$C_6$-cycloalkyl which is optionally monosubstituted by methyl, ethyl, methoxy, fluorine, chlorine, trifluoromethyl or cyclopropyl, represents $C_1$-$C_4$-alkoxy, $C_1$-$C_2$-haloalkyl or $C_1$-$C_2$-haloalkoxy or cyano, Y and Z independently of one another particularly preferably represent hydrogen, fluorine, chlorine, bromine, iodine, $C_1$-$C_4$-alkyl, $C_2$-$C_4$-alkenyl, $C_2$-$C_4$-alkynyl, represent $C_3$-$C_6$-cycloalkyl which is optionally monosubstituted by methyl, ethyl, methoxy, fluorine, chlorine, trifluoromethyl or cyclopropyl, represent $C_1$-$C_6$-alkoxy, $C_1$-$C_4$-haloalkoxy, cyano, $C_2$-$C_4$-alkenyl, $C_2$-$C_4$-alkynyl or represent one of the (het)aryl radicals

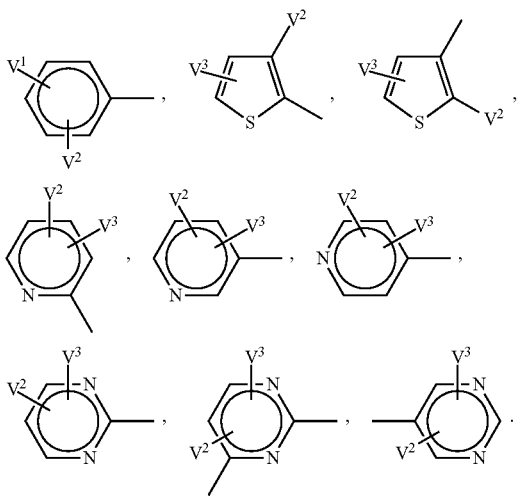

where in the case of (het)aryl only one of the radicals Y or Z may represent (het)aryl, $V^1$ particularly preferably represents hydrogen, fluorine, chlorine, bromine, $C_1$-$C_6$-alkyl, $C_1$-$C_4$-alkoxy, $C_1$-$C_2$-haloalkyl, $C_1$-$C_2$-haloalkoxy, nitro, cyano or represents phenyl which is optionally mono- or disubstituted by fluorine, chlorine, bromine, $C_1$-$C_4$-alkyl, $C_1$-$C_4$-alkoxy, $C_1$-$C_2$-haloalkyl, $C_1$-$C_2$-haloalkoxy, nitro or cyano, $V^2$ and $V^3$ independently of one another particularly preferably represent hydrogen, fluorine, chlorine, bromine, $C_1$-$C_4$-alkyl, $C_1$-$C_4$-alkoxy, $C_1$-$C_2$-haloalkyl or $C_1$-$C_2$-haloalkoxy, A particularly preferably represents

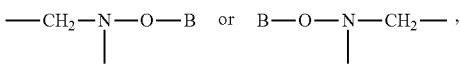

B particularly preferably represents hydrogen, $C_1$-$C_4$-allyl, $C_1$-$C_4$-haloalkyl, $C_1$-$C_4$-alkoxyl-$C_1$-$C_2$-alkyl, represents phenyl-$C_1$-$C_2$-alkyl, pyridyl-$C_1$-$C_2$-alkyl or $C_3$-$C_6$-cycloalkyl-$C_1$-$C_2$-alkyl (which may optionally be interrupted by an oxygen atom), each of which is optionally mono- or disubstituted by fluorine, chlorine, bromine, methyl, ethyl, trifluoromethyl, trifluoromethoxy, methoxy or ethoxy, t particularly preferably represents the number 1, G particularly preferably represents hydrogen (a) or represents one of the groups

 (b)

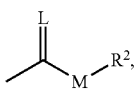 (c)

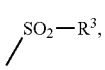 (d)

 (e)

E, or (f)

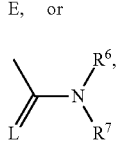 (g)

in which

E represents a metal ion or an ammonium ion,

L represents oxygen or sulphur and

M represents oxygen or sulphur, $R^1$ particularly preferably represents $C_1$-$C_{16}$-alkyl, $C_2$-$C_{16}$-alkenyl, $C_1$-$C_6$-alkoxy-$C_1$-$C_4$-alkyl, $C_1$-$C_6$-alkylthio-$C_1$-$C_4$-alkyl or poly-$C_1$-$C_6$-alkoxy-$C_1$-$C_4$-alkyl, each of which is optionally mono- to trisubstituted by fluorine or chlorine or represents $C_3$-$C_7$-cycloalkyl which is optionally mono- or disubstituted by fluorine, chlorine, $C_1$-$C_5$-alkyl or $C_1$-$C_5$-alkoxy and in which optionally one or two not directly adjacent methylene groups are replaced by oxygen and/or sulphur, represents phenyl which is optionally mono- to trisubstituted by fluorine, chlorine, bromine, cyano, nitro, $C_1$-$C_4$-alkyl, $C_1$-$C_4$-alkoxy, $C_1$-$C_3$-haloalkyl, $C_1$-$C_3$-haloalkoxy, $C_1$-$C_4$-alkylthio or $C_1$-$C_4$-alkylsulphonyl, represents phenyl-$C_1$-$C_4$-alkyl which is optionally mono- or disubstituted by fluorine, chlorine, bromine, $C_1$-$C_4$-alkyl, $C_1$-$C_4$-alkoxy, $C_1$-$C_3$-haloalkyl or $C_1$-$C_3$-haloalkoxy, represents pyrazolyl, thiazolyl, pyridyl, pyrimidyl, furanyl or thienyl, each of which is optionally mono- or disubstituted by fluorine, chlorine, bromine or $C_1$-$C_4$-alkyl, represents phenoxy-$C_1$-$C_5$-alkyl which is optionally mono- or disubstituted by fluorine, chlorine, bromine or $C_1$-$C_4$-alkyl or represents pyridyloxy-$C_1$-$C_5$-alkyl, pyrimidyloxy-$C_1$-$C_5$-alkyl or thiazolyl oxy-$C_1$-$C_5$-alkyl, each of which is optionally mono- or disubstituted by fluorine, chlorine, bromine, amino or $C_1$-$C_4$-alkyl, $R^2$ particularly preferably represents $C_1$-$C_{16}$-alkyl, $C_2$-$C_{16}$-alkenyl, $C_1$-$C_6$-alkoxy-$C_2$-$C_6$-alkyl or poly-$C_1$-$C_6$-alkoxy-$C_2$-$C_6$-alkyl, each of which is optionally mono- to trisubstituted by fluorine or chlorine, represents $C_3$-$C_7$-cycloalkyl which is optionally mono- or disubstituted by fluorine, chlorine, $C_1$-$C_4$-alkyl or $C_1$-$C_4$-alkoxy or represents phenyl or benzyl, each of which is optionally mono- to trisubstituted by fluorine, chlorine, bromine, cyano, nitro, $C_1$-$C_4$-alkyl, $C_1$-$C_3$-alkoxy, $C_1$-$C_3$-haloalkyl or $C_1$-$C_3$-haloalkoxy, $R^3$ particularly preferably represents $C_1$-$C_6$-alkyl which is optionally mono- to trisubstituted by fluorine or chlorine or represents phenyl or benzyl, each of which is optionally mono- or disubstituted by fluorine, chlorine, bromine, $C_1$-$C_4$-alkyl, $C_1$-$C_4$-alkoxy, $C_1$-$C_2$-halo-alkoxy, $C_1$-$C_2$-haloalkyl, cyano or nitro, $R^4$ and $R^5$ independently of one another particularly preferably represent $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio or $C_3$-$C_4$-alkenylthio, each of which is optionally mono- to trisubstituted by fluorine or chlorine, or represent phenyl, phenoxy or phenylthio, each of which is optionally mono- or disubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or $C_1$-$C_3$-haloalkyl, $R^6$ and $R^7$ independently of one another particularly preferably represent $C_1$-$C_6$-alkyl, $C_3$-$C_6$-cycloalkyl, $C_1$-$C_6$-alkoxy, $C_3$-$C_6$-alkenyl or $C_1$-$C_6$-alkoxy-$C_2$-$C_6$-alkyl, each of which is optionally mono- to trisubstituted by fluorine or chlorine, represent phenyl or benzyl, each of which is optionally mono- to trisubstituted by fluorine, chlorine, bromine, $C_1$-$C_5$-haloalkyl, $C_1$-$C_5$-alkyl or $C_1$-$C_5$-alkoxy, or together represent an optionally $C_1$-$C_4$-alkyl-substituted $C_3$-$C_6$-alkylene radical in which optionally one methylene group is replaced by oxygen or sulphur.

In the radical definitions mentioned as being particularly preferred, halogen represents fluorine, chlorine and bromine, in particular fluorine and chlorine.

W very particularly preferably represents hydrogen, chlorine, bromine, methyl, ethyl, vinyl, ethynyl, propynyl, cyclopropyl, methoxy, ethoxy or trifluoromethyl, X very particularly preferably represents chlorine, bromine, methyl, ethyl, propyl, isopropyl, vinyl, ethynyl, propynyl, cyclopropyl, methoxy, ethoxy, trifluoromethyl, difluoromethoxy, trifluoromethoxy or cyano, Y and Z independently of one another very particularly preferably represent hydrogen, fluorine, chlorine, bromine, iodine, methyl, ethyl, vinyl, ethynyl, propynyl, cyclopropyl, methoxy, trifluoromethyl, trifluoromethoxy, cyano or a phenyl radical,

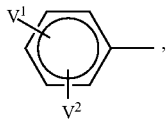

where in the case of phenyl only one of the radicals Y or Z may represent phenyl, $V^1$ very particularly preferably represents hydrogen, fluorine or chlorine, $V^2$ very particularly preferably represents hydrogen, fluorine, chlorine, methyl, ethyl, n-propyl, isopropyl, methoxy, ethoxy or trifluoromethyl, A very particularly preferably represents

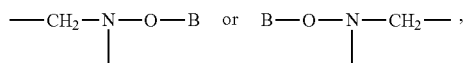

B very particularly preferably represents hydrogen, methyl, ethyl, propyl, methoxyethyl, ethoxyethyl, benzyl, cyclopropylmethyl or tetrahydrofuranylmethyl, t very particularly preferably represents the number 1, G very particularly preferably represents hydrogen (a) or represents one of the groups

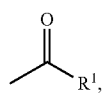
(b)

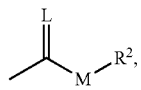
(c)

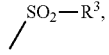
(d)

(e)

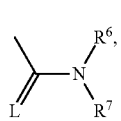
(f)

E, or
(g)

M which

E represents a metal ion or an ammonium ion,

L represents oxygen or sulphur and

M represents oxygen or sulphur, $R^1$ very particularly preferably represents $C_1$-$C_{10}$-alkyl, $C_2$-$C_2$-$C_{10}$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine or represents $C_3$-$C_6$-cycloalkyl which is optionally monosubstituted by fluorine, chlorine, methyl, ethyl or methoxy, represents phenyl which is optionally mono- or disubstituted by fluorine, chlorine, bromine, cyano, nitro, methyl, ethyl, n-propyl, isopropyl, methoxy, ethoxy, trifluoromethyl or trifluorornethoxy, represents furanyl, thienyl or pyridyl, each of which is optionally monosubstituted by chlorine, bromine or methyl, $R^2$ very particularly preferably represents $C_1$-$C_{10}$-alkyl, $C_2$-$C_{10}$-alkenyl or $C_1$-$C_4$-alkoxy-$C_2$-$C_4$-alkyl, each of which is optionally mono- to trisubstituted by fluorine or chlorine, represents cyclopentyl or cyclohexyl, or represents phenyl or benzyl, each of which is optionally mono- or disubstituted by fluorine, chlorine; cyano, nitro, methyl, ethyl, methoxy, trifluoromethyl or trifluoro-methoxy, $R^3$ very particularly preferably represents methyl, ethyl, propyl or isopropyl, each of which is optionally mono- to trisubstituted by fluorine or chlorine, or represents phenyl which is optionally monosubstituted by fluorine, chlorine, bromine, methyl, ethyl, isopropyl, tert-butyl, methoxy, ethoxy, isopropoxy, trifluoromethyl, trifluoromethoxy, cyano or nitro, $R^4$ and $R^5$ independently of one another very particularly preferably represent $C_1$-$C_4$-alkoxy or $C_1$-$C_4$-alkylthio or represent phenyl, phenoxy or phenylthio, each of which is optionally monosubstituted by fluorine, chlorine, bromine, nitro, cyano, methyl, methoxy, trifluoromethyl or trifluoromethoxy, $R^6$ and $R^7$ independently of one another very particularly preferably represent hydrogen, represent $C_1$-$C_4$-alkyl, $C_3$-$C_6$-cycloalkyl, $C_1$-$C_4$-alkoxy, $C_3$-$C_4$-alkenyl or $C_1$-$C_4$-alkoxy-$C_2$-$C_4$-alkyl, represent phenyl which is optionally mono- or disubstituted by fluorine, chlorine, bromine, methyl, methoxy or trifluoromethyl, or together represent a $C_5$-$C_6$-alkylene radical in which optionally one methylene group is replaced by oxygen or sulphur.

W especially preferably represents hydrogen, chlorine, bromine, methyl, ethyl or methoxy (with emphasis hydrogen, methyl or ethyl), X especially preferably represents chlorine, bromine, methyl, ethyl or methoxy (with emphasis methyl or ethyl), Y and Z independently of one another especially preferably represent hydrogen, chlorine, bromine, methyl or represent the radical

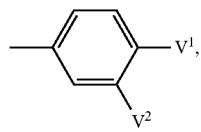

where in this case only one of the radicals Y or Z may represent

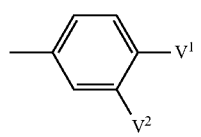

(with emphasis hydrogen, methyl or the radical)

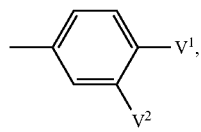

where in this case only one of the radicals Y or Z may represent

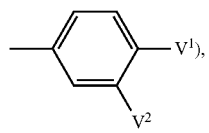

$V^1$ especially preferably represents fluorine or chlorine, $V^2$ especially preferably represents hydrogen, fluorine or chlorine (with emphasis hydrogen), A especially preferably represents

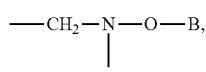

t especially preferably represents the number 1,

B especially preferably represents hydrogen, methyl or ethyl (with emphasis methyl or ethyl), G especially preferably represents hydrogen (a) or represents one of the groups

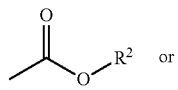

(with emphasis hydrogen (a) or one of the groups (b) or (c)), in which

E represents a metal ion or an ammonium ion, $R^1$ especially preferably represents $C_1$-$C_{10}$-alkyl, $C_1$-$C_4$-alkoxy-$C_1$-$C_2$-alkyl, $C_3$-$C_6$-cycloalkyl, represents phenyl which is optionally monosubstituted by chlorine or represents thienyl (with emphasis $C_1$-$C_{10}$-alkyl), $R^2$ especially preferably represents $C_1$-$C_{10}$-alkyl, $C_2$-$C_{10}$-alkenyl or represents benzyl (with emphasis $C_1$-$C_{10}$-alkyl).

The general or preferred radical definitions or illustrations listed above can be combined with one another as desired, i.e. including combinations between the respective ranges and preferred ranges. They apply both to the end products and, correspondingly, to the precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Special preference according to the invention is given to the compounds of the formula (I) which contain a combination of the meanings listed above as being especially preferred.

Emphasis according to the invention is given to the compounds of the formula (I) which contain a combination of the meanings listed above as emphasized.

Emphasis is also given to compounds of the formula (I) in which G represents hydrogen.

Saturated or unsaturated hydrocarbon radicals, such as alkyl, alkanediyl or alkeryl, can in each case be straight-chain or branched as far as this is possible, including in combination with heteroatoms, such as, for example, in alkoxy.

Optionally substituted radicals may be mono- or polysubstituted unless indicated otherwise, and in the case of multiple substitutions the substituents can be identical or different.

In addition to the compounds mentioned in the examples, specific mention may also be made of

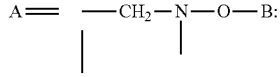

TABLE 1

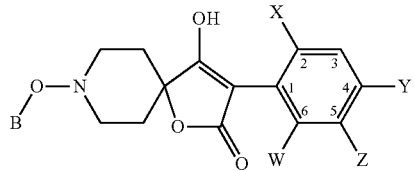

(I-a)

| B | X | W | Y | Z |
|---|---|---|---|---|
| $CH_3$ | $CH_3$ | H | H | H |
| $CH_3$ | Br | H | H | H |
| $CH_3$ | Cl | H | H | H |
| $CH_3$ | $CF_3$ | H | H | H |
| $CH_3$ | $OCH_3$ | H | H | H |
| $CH_3$ | Br | H | Cl | H |
| $CH_3$ | Cl | H | Br | H |
| $CH_3$ | Cl | H | Cl | H |
| $CH_3$ | Cl | H | $CH_3$ | H |
| $CH_3$ | $CH_3$ | H | Cl | H |
| $CH_3$ | Cl | Cl | H | H |
| $CH_3$ | Cl | $OCH_3$ | H | H |
| $CH_3$ | Cl | $CH_3$ | H | H |
| $CH_3$ | Cl | $OC_2H_5$ | H | H |
| $CH_3$ | $OCH_3$ | $OCH_3$ | H | H |
| $CH_3$ | $CH_3$ | $CH_3$ | H | H |
| $CH_3$ | $C_2H_5$ | $CH_3$ | H | H |
| $CH_3$ | $C_2H_5$ | $C_2H_5$ | H | H |
| $CH_3$ | Br | $CH_3$ | Br | H |
| $CH_3$ | Cl | $CH_3$ | Cl | H |
| $CH_3$ | $CH_3$ | Br | $CH_3$ | H |
| $CH_3$ | $CH_3$ | Cl | $CH_3$ | H |
| $CH_3$ | $OCH_3$ | $CH_3$ | $CH_3$ | H |
| $CH_3$ | $OC_2H_5$ | $CH_3$ | $CH_3$ | H |
| $CH_3$ | $OC_3H_7$ | $CH_3$ | $CH_3$ | H |
| $CH_3$ | $CH_3$ | $CH_3$ | $CH_3$ | H |
| $CH_3$ | Br | Br | $CH_3$ | H |
| $CH_3$ | Cl | Cl | $CH_3$ | H |
| $CH_3$ | $CH_3$ | $CH_3$ | Br | H |
| $CH_3$ | $OCH_3$ | $C_2H_5$ | $CH_3$ | H |
| $CH_3$ | $OC_2H_5$ | $C_2H_5$ | $CH_3$ | H |
| $CH_3$ | $CH_3$ | $CH_3$ | $OCH_3$ | H |
| $CH_3$ | Br | Cl | $CH_3$ | H |
| $CH_3$ | Br | $CH_3$ | Cl | H |
| $CH_3$ | Cl | $CH_3$ | Br | H |
| $CH_3$ | $CH_3$ | $CH_3$ | Cl | H |
| $CH_3$ | $C_2H_5$ | $CH_3$ | $CH_3$ | H |
| $CH_3$ | $C_2H_5$ | $C_2H_5$ | $CH_3$ | H |
| $CH_3$ | $C_2H_5$ | $C_2H_5$ | $C_2H_5$ | H |
| $CH_3$ | $C_2H_5$ | $CH_3$ | Cl | H |
| $CH_3$ | $C_2H_5$ | $C_2H_5$ | Cl | H |
| $CH_3$ | $C_2H_5$ | $CH_3$ | Br | H |
| $CH_3$ | $C_2H_5$ | $C_2H_5$ | Br | H |
| $CH_3$ | $C_2H_5$ | Cl | $CH_3$ | H |
| $CH_3$ | $C_2H_5$ | Br | $CH_3$ | H |
| $CH_3$ | $C_2H_5$ | Cl | Cl | H |
| $CH_3$ | $C_2H_5$ | Br | Br | H |
| $CH_3$ | $C_2H_5$ | Cl | Br | H |
| $CH_3$ | $C_2H_5$ | Br | Cl | H |
| $CH_3$ | $OCH_3$ | $CH_3$ | Cl | H |
| $CH_3$ | $OCH_3$ | $C_2H_5$ | Cl | H |
| $CH_3$ | $OC_2H_5$ | $CH_3$ | Cl | H |
| $CH_3$ | $OC_2H_5$ | $C_2H_5$ | Cl | H |
| $CH_3$ | Cl | $OCH_3$ | $CH_3$ | H |
| $CH_3$ | Cl | $OC_2H_5$ | $CH_3$ | H |
| $CH_3$ | $CH_3$ | $CH_3$ | Cl | H |
| $CH_3$ | Cl | H | Cl | Cl |
| $CH_3$ | $CH_3$ | H | $CH_3$ | $CH_3$ |
| $CH_3$ | Br | H | Cl | $CH_3$ |
| $CH_3$ | Br | H | $CH_3$ | $CH_3$ |
| $CH_3$ | Cl | H | Br | $CH_3$ |
| $CH_3$ | $CH_3$ | H | Br | $CH_3$ |
| $CH_3$ | Cl | H | $CH_3$ | Cl |
| $CH_3$ | $CH_3$ | H | H | $CH_3$ |
| $CH_3$ | Cl | H | H | $CH_3$ |

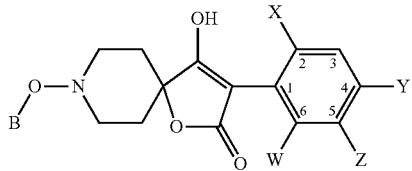

(I-a)

| B | X | W | Y | Z |
|---|---|---|---|---|
| $CH_3$ | Br | H | H | $CH_3$ |
| $CH_3$ | $CH_3$ | H | H | Cl |
| $CH_3$ | $CH_3$ | H | H | Br |
| $CH_3$ | $CH_3$ | $CH_3$ | $CH_3$ | $CH_3$ |
| $CH_3$ | $CH_3$ | $CH_3$ | $CH_3$ | F |
| $CH_3$ | $CH_3$ | $CH_3$ | $CH_3$ | Cl |
| $CH_3$ | $CH_3$ | $CH_3$ | $CH_3$ | Br |
| $CH_3$ | $CH_3$ | $CH_3$ | H | Cl |
| $CH_3$ | $CH_3$ | $CH_3$ | H | Br |
| $CH_3$ | Cl | Cl | H | Br |
| $CH_3$ | $CH_3$ | $CH_3$ | 4-Cl—$C_6H_4$ | H |
| $CH_3$ | $C_2H_5$ | $CH_3$ | 4-Cl—$C_6H_4$ | H |
| $CH_3$ | $C_2H_5$ | $C_2H_5$ | 4-Cl—$C_6H_4$ | H |
| $CH_3$ | Cl | $CH_3$ | 4-Cl—$C_6H_4$ | H |
| $CH_3$ | Cl | $C_2H_5$ | 4-Cl—$C_6H_4$ | H |
| $CH_3$ | $CH_3$ | H | H | 4-Cl—$C_6H_4$ |
| $CH_3$ | $CH_3$ | $CH_3$ | H | 4-Cl—$C_6H_4$ |
| $CH_3$ | $CH_3$ | H | $CH_3$ | 4-Cl—$C_6H_4$ |
| $CH_3$ | $CH_3$ | $CH_3$ | $CH_3$ | 4-Cl—$C_6H_4$ |
| $CH_3$ | Cl | H | H | 4-Cl—$C_6H_4$ |
| $CH_3$ | $CH_3$ | $CH_3$ | 4-$CH_3$—$C_6H_4$ | H |
| $CH_3$ | $C_2H_5$ | $CH_3$ | 4-$CH_3$—$C_6H_4$ | H |
| $CH_3$ | $C_2H_5$ | $C_2H_5$ | 4-$CH_3$—$C_6H_4$ | H |
| $CH_3$ | Cl | $CH_3$ | 4-$CH_3$—$C_6H_4$ | H |
| $CH_3$ | Cl | $C_2H_5$ | 4-$CH_3$—$C_6H_4$ | H |
| $CH_3$ | $CH_3$ | H | H | 4-$CH_3$—$C_6H_4$ |
| $CH_3$ | $CH_3$ | $CH_3$ | H | 4-$CH_3$—$C_6H_4$ |
| $CH_3$ | $CH_3$ | H | $CH_3$ | 4-$CH_3$—$C_6H_4$ |
| $CH_3$ | $CH_3$ | $CH_3$ | $CH_3$ | 4-$CH_3$—$C_6H_4$ |
| $CH_3$ | Cl | H | H | 4-$CH_3$—$C_6H_4$ |
| $CH_3$ | $CH_3$ | $CH_3$ | 4-$CF_3$—$C_6H_4$ | H |
| $CH_3$ | $C_2H_5$ | $CH_3$ | 4-$CF_3$—$C_6H_4$ | H |
| $CH_3$ | $C_2H_5$ | $C_2H_5$ | 4-$CF_3$—$C_6H_4$ | H |
| $CH_3$ | Cl | $CH_3$ | 4-$CF_3$—$C_6H_4$ | H |
| $CH_3$ | Cl | $C_2H_5$ | 4-$CF_3$—$C_6H_4$ | H |
| $CH_3$ | $CH_3$ | H | H | 4-$CF_3$—$C_6H_4$ |
| $CH_3$ | $CH_3$ | $CH_3$ | H | 4-$CF_3$—$C_6H_4$ |
| $CH_3$ | $CH_3$ | H | $CH_3$ | 4-$CF_3$—$C_6H_4$ |
| $CH_3$ | $CH_3$ | $CH_3$ | $CH_3$ | 4-$CF_3$—$C_6H_4$ |
| $CH_3$ | Cl | H | H | 4-$CF_3$—$C_6H_4$ |
| $CH_3$ | $CH_3$ | $CH_3$ | 4-$OCH_3$—$C_6H_4$ | H |
| $CH_3$ | $C_2H_5$ | $CH_3$ | 4-$OCH_3$—$C_6H_4$ | H |
| $CH_3$ | $C_2H_5$ | $C_2H_5$ | 4-$OCH_3$—$C_6H_4$ | H |
| $CH_3$ | Cl | $CH_3$ | 4-$OCH_3$—$C_6H_4$ | H |
| $CH_3$ | Cl | $C_2H_5$ | 4-$OCH_3$—$C_6H_4$ | H |
| $CH_3$ | $CH_3$ | H | H | 4-$OCH_3$—$C_6H_4$ |
| $CH_3$ | $CH_3$ | $CH_3$ | H | 4-$OCH_3$—$C_6H_4$ |
| $CH_3$ | $CH_3$ | H | $CH_3$ | 4-$OCH_3$—$C_6H_4$ |
| $CH_3$ | $CH_3$ | $CH_3$ | $CH_3$ | 4-$OCH_3$—$C_6H_4$ |
| $CH_3$ | Cl | H | H | 4-$OCH_3$—$C_6H_4$ |
| $CH_3$ | I | H | H | H |
| $CH_3$ | I | H | $CH_3$ | H |
| $CH_3$ | I | $CH_3$ | H | H |
| $CH_3$ | I | $C_2H_5$ | H | H |
| $CH_3$ | $CH_3$ | H | H | I |
| $CH_3$ | $CH_3$ | H | $CH_3$ | I |
| $CH_3$ | I | $CH_3$ | H | H |
| $CH_3$ | I | $C_2H_5$ | $CH_3$ | H |
| $CH_3$ | I | $CH_3$ | Cl | H |
| $CH_3$ | I | $C_2H_5$ | Cl | H |
| $CH_3$ | I | Cl | $CH_3$ | H |
| $CH_3$ | I | H | $CH_3$ | $CH_3$ |
| $CH_3$ | $CH_3$ | H | I | H |
| $CH_3$ | $CH_3$ | $C_2H_5$ | I | H |
| $CH_3$ | $CH_3$ | $CH_3$ | I | H |
| $CH_3$ | $C_2H_5$ | $CH_3$ | I | H |
| $CH_3$ | $C_2H_5$ | $C_2H_5$ | I | H |
| $CH_3$ | Cl | $CH_3$ | I | H |

TABLE 1-continued

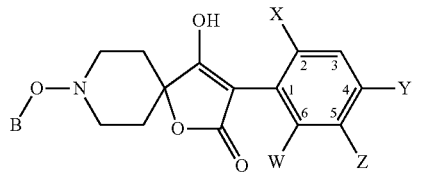

(I-a)

| B | X | W | Y | Z |
|---|---|---|---|---|
| CH3 | Cl | C2H5 | I | H |
| CH3 | CH3 | H | I | CH3 |
| CH3 | CH3 | CH3 | H | I |
| CH3 | I | H | H | CH3 |
| CH3 | C2H5 | H | H | H |
| CH3 | c-Pr | H | H | H |
| CH3 | c-Pr | CH3 | H | H |
| CH3 | c-Pr | H | CH3 | H |
| CH3 | c-Pr | C2H5 | H | H |
| CH3 | c-Pr | CH3 | CH3 | H |
| CH3 | c-Pr | C2H5 | CH3 | H |
| CH3 | c-Pr | CH3 | Cl | H |
| CH3 | c-Pr | C2H5 | Cl | H |
| CH3 | c-Pr | Cl | CH3 | H |
| CH3 | CH3 | H | c-Pr | H |
| CH3 | C2H5 | H | c-Pr | H |
| CH3 | CH3 | CH3 | c-Pr | H |
| CH3 | C2H5 | CH3 | c-Pr | H |
| CH3 | C2H5 | C2H5 | c-Pr | H |
| CH3 | Cl | CH3 | c-Pr | H |
| CH3 | Cl | C2H5 | c-Pr | H |
| CH3 | CH3 | H | O—CH2—CF3 | H |
| CH3 | CH3 | CH3 | O—CH2—CF3 | H |
| CH3 | CH3 | H | H | O—CH2—CF3 |
| CH3 | CH3 | CH3 | H | O—CH2—CF3 |
| CH3 | C2H5 | H | O—CH2—CF3 | H |
| CH3 | C2H5 | CH3 | O—CH2—CF3 | H |
| CH3 | C2H5 | C2H5 | O—CH2—CF3 | H |
| CH3 | C2H5 | H | H | O—CH2—CF3 |
| CH3 | C2H5 | C2H5 | H | O—CH2—CF3 |

In addition to the compounds mentioned in the examples, mention may also be made of the following compounds of the formula (I):

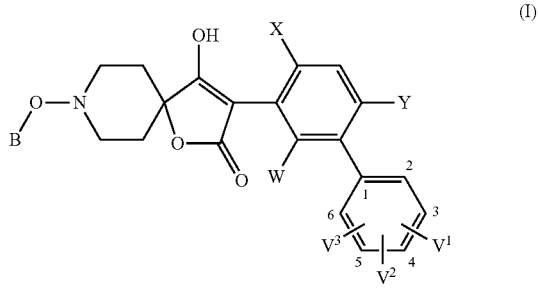

(I)

TABLE 2

| B | W | X | Y | V1 | V2 | V3 |
|---|---|---|---|---|---|---|
| CH3 | H | Cl | H | 2-F | H | H |
| CH3 | H | Cl | H | 3-F | H | H |
| CH3 | H | Cl | H | 4-F | H | H |
| CH3 | H | Cl | H | 2-F | 4-F | H |
| CH3 | H | Cl | H | 2-F | 4-Cl | H |
| CH3 | H | Cl | H | 2-F | 4-CH3 | H |
| CH3 | H | Cl | H | 2-F | 4-OCH3 | H |
| CH3 | H | Cl | H | 3-F | 4-F | H |
| CH3 | H | Cl | H | 3-F | 4-Cl | H |
| CH3 | H | Cl | H | 3-F | 4-CH3 | H |
| CH3 | H | Cl | H | 3-F | 4-OCH3 | H |
| CH3 | H | Cl | H | 4-F | 3-Cl | H |
| CH3 | H | Cl | H | 4-F | 3-CH3 | H |
| CH3 | H | Cl | H | 4-F | 3-OCH3 | H |
| CH3 | H | Cl | H | 2-F | 4-F | 5-F |
| CH3 | H | Cl | H | 2-F | 4-F | 6-F |
| CH3 | H | Cl | H | 2-F | 4-Cl | 5-F |
| CH3 | H | Cl | H | 2-F | 5-Cl | 4-F |
| CH3 | H | Cl | H | 3-F | 4-F | 5-F |
| CH3 | H | Cl | H | 3-Cl | 4-Cl | H |
| CH3 | H | Cl | H | 4-CF3 | 3-F | H |
| CH3 | H | Cl | H | 4-CN | H | H |
| CH3 | H | Cl | H | 3-CF3 | 4-F | H |
| CH3 | H | CH3 | H | 2-F | H | H |
| CH3 | H | CH3 | H | 3-F | H | H |
| CH3 | H | CH3 | H | 4-F | H | H |
| CH3 | H | CH3 | H | 2-F | 4-F | H |
| CH3 | H | CH3 | H | 2-F | 4-Cl | H |
| CH3 | H | CH3 | H | 2-F | 4-CH3 | H |
| CH3 | H | CH3 | H | 2-F | 4-OCH3 | H |
| CH3 | H | CH3 | H | 3-F | 4-F | H |
| CH3 | H | CH3 | H | 3-F | 4-Cl | H |
| CH3 | H | CH3 | H | 3-F | 4-CH3 | H |
| CH3 | H | CH3 | H | 3-F | 4-OCH3 | H |
| CH3 | H | CH3 | H | 4-F | 3-Cl | H |
| CH3 | H | CH3 | H | 4-F | 3-CH3 | H |
| CH3 | H | CH3 | H | 4-F | 3-OCH3 | H |
| CH3 | H | CH3 | H | 2-F | 4-F | 5-F |
| CH3 | H | CH3 | H | 2-F | 4-F | 6-F |
| CH3 | H | CH3 | H | 2-F | 4-Cl | 5-F |
| CH3 | H | CH3 | H | 2-F | 5-Cl | 4-F |
| CH3 | H | CH3 | H | 3-F | 4-F | 5-F |
| CH3 | H | CH3 | H | 3-Cl | 4-Cl | H |
| CH3 | H | CH3 | H | 4-CF3 | 3-F | H |
| CH3 | H | CH3 | H | 4-CN | H | H |
| CH3 | H | CH3 | H | 3-CF3 | 4-F | H |
| CH3 | CH3 | CH3 | H | 2-F | H | H |
| CH3 | CH3 | CH3 | H | 3-F | H | H |
| CH3 | CH3 | CH3 | H | 4-F | H | H |
| CH3 | CH3 | CH3 | H | 2-F | 4-F | H |
| CH3 | CH3 | CH3 | H | 2-F | 4-Cl | H |
| CH3 | CH3 | CH3 | H | 2-F | 4-CH3 | H |
| CH3 | CH3 | CH3 | H | 2-F | 4-OCH3 | H |
| CH3 | CH3 | CH3 | H | 3-F | 4-F | H |
| CH3 | CH3 | CH3 | H | 3-F | 4-Cl | H |

TABLE 2-continued

| B | W | X | Y | V¹ | V² | V³ |
|---|---|---|---|---|---|---|
| CH₃ | CH₃ | CH₃ | H | 3-F | 4-CH₃ | H |
| CH₃ | CH₃ | CH₃ | H | 3-F | 4-OCH₃ | H |
| CH₃ | CH₃ | CH₃ | H | 4-F | 3-Cl | H |
| CH₃ | CH₃ | CH₃ | H | 4-F | 3-CH₃ | H |
| CH₃ | CH₃ | CH₃ | H | 4-F | 3-OCH₃ | H |
| CH₃ | CH₃ | CH₃ | H | 2-F | 4-F | 5-F |
| CH₃ | CH₃ | CH₃ | H | 2-F | 4-F | 6-F |
| CH₃ | CH₃ | CH₃ | H | 2-F | 4-Cl | 5-F |
| CH₃ | CH₃ | CH₃ | H | 2-F | 5-Cl | 4-F |
| CH₃ | CH₃ | CH₃ | H | 3-F | 4-F | 5-F |
| CH₃ | CH₃ | CH₃ | H | 3-CF₃ | 4-F | H |
| CH₃ | CH₃ | CH₃ | H | 3-Cl | 4-Cl | H |
| CH₃ | CH₃ | CH₃ | H | 4-CF₃ | 3-F | H |
| CH₃ | CH₃ | CH₃ | H | 4-CN | H | H |
| CH₃ | H | CH₃ | CH₃ | 2-F | H | H |
| CH₃ | H | CH₃ | CH₃ | 3-F | H | H |
| CH₃ | H | CH₃ | CH₃ | 4-F | H | H |
| CH₃ | H | CH₃ | CH₃ | 2-F | 4-F | H |
| CH₃ | H | CH₃ | CH₃ | 2-F | 4-Cl | H |
| CH₃ | H | CH₃ | CH₃ | 2-F | 4-CH₃ | H |
| CH₃ | H | CH₃ | CH₃ | 2-F | 4-OCH₃ | H |
| CH₃ | H | CH₃ | CH₃ | 3-F | 4-F | H |
| CH₃ | H | CH₃ | CH₃ | 3-F | 4-Cl | H |
| CH₃ | H | CH₃ | CH₃ | 3-F | 4-CH₃ | H |
| CH₃ | H | CH₃ | CH₃ | 3-F | 4-OCH₃ | H |
| CH₃ | H | CH₃ | CH₃ | 4-F | 3-Cl | H |
| CH₃ | H | CH₃ | CH₃ | 4-F | 3-CH₃ | H |
| CH₃ | H | CH₃ | CH₃ | 4-F | 3-OCH₃ | H |
| CH₃ | H | CH₃ | CH₃ | 2-F | 4-F | 5-F |
| CH₃ | H | CH₃ | CH₃ | 2-F | 4-F | 6-F |
| CH₃ | H | CH₃ | CH₃ | 2-F | 4-Cl | 5-F |
| CH₃ | H | CH₃ | CH₃ | 2-F | 5-Cl | 4-F |
| CH₃ | H | CH₃ | CH₃ | 3-F | 4-F | 5-F |
| CH₃ | CH₃ | CH₃ | H | 3-Cl | 4-Cl | H |
| CH₃ | CH₃ | CH₃ | H | 4-CF₃ | 3-F | H |
| CH₃ | CH₃ | CH₃ | H | 4-CN | H | H |
| CH₃ | CH₃ | CH₃ | H | 3-CF₃ | 4-F | H |
| CH₃ | CH₃ | CH₃ | CH₃ | 2-F | H | H |
| CH₃ | CH₃ | CH₃ | CH₃ | 3-F | H | H |
| CH₃ | CH₃ | CH₃ | CH₃ | 4-F | H | H |
| CH₃ | CH₃ | CH₃ | CH₃ | 2-F | 4-F | H |
| CH₃ | CH₃ | CH₃ | CH₃ | 2-F | 4-Cl | H |
| CH₃ | CH₃ | CH₃ | CH₃ | 2-F | 4-CH₃ | H |
| CH₃ | CH₃ | CH₃ | CH₃ | 2-F | 4-OCH₃ | H |
| CH₃ | CH₃ | CH₃ | CH₃ | 3-F | 4-F | H |
| CH₃ | CH₃ | CH₃ | CH₃ | 3-F | 4-Cl | H |
| CH₃ | CH₃ | CH₃ | CH₃ | 3-F | 4-CH₃ | H |
| CH₃ | CH₃ | CH₃ | CH₃ | 3-F | 4-OCH₃ | H |
| CH₃ | CH₃ | CH₃ | CH₃ | 4-F | 3-Cl | H |
| CH₃ | CH₃ | CH₃ | CH₃ | 4-F | 3-CH₃ | H |
| CH₃ | CH₃ | CH₃ | CH₃ | 4-F | 3-OCH₃ | H |
| CH₃ | CH₃ | CH₃ | CH₃ | 2-F | 4-F | 5-F |
| CH₃ | CH₃ | CH₃ | CH₃ | 2-F | 4-F | 6-F |
| CH₃ | CH₃ | CH₃ | CH₃ | 2-F | 4-Cl | 5-F |
| CH₃ | CH₃ | CH₃ | CH₃ | 2-F | 5-Cl | 4-F |
| CH₃ | CH₃ | CH₃ | CH₃ | 3-F | 4-F | 5-F |
| CH₃ | CH₃ | CH₃ | H | 3-Cl | 4-Cl | H |
| CH₃ | CH₃ | CH₃ | H | 4-CF₃ | 3-F | H |
| CH₃ | CH₃ | CH₃ | H | 4-CN | H | H |
| CH₃ | CH₃ | CH₃ | H | 3-CF₃ | 4-F | H |

Table 3 W, X, Y and Z as stated in Table 1 and

B=C₂H₅

Table 4 W, X, Y, V¹, V² and V³ as stated in Table 2 and

B=C₂H₅

In the literature it has already been described how the action of various active compounds can be boosted by addition of ammonium salts. The salts in question, however, are detersive salts (for example WO 95/017817) or salts which have relatively long alkyl substituents and/or aryl substituents and which have a permeabilizing action or which increase the active compound's solubility (for example EP-A 0 453 086, EP-A 0 664 081, FR-A 2 600 494, U.S. Pat. No. 4,844,734, U.S. Pat. No. 5,462,912, U.S. Pat. No. 5,538,937, U.S. application Ser. No. 03/0,224,939, U.S. application Ser. No. 05/0,009,880, U.S. application Ser. No. 05/0,096,386). Moreover, the prior art describes the action only for particular active compounds and/or particular applications of the corresponding compositions. In other cases, in turn, the salts in question are those of sulphonic acids, where the acids themselves have a paralytic action on insects (U.S. Pat. No. 2,842,476). A boost to action by ammonium sulphate, for example, is described by way of example for the herbicides glyphosate, phosphinothricin and for phenyl-substituted cyclic ketoenols (U.S. Pat. No. 6,645,914, EP-A2 0 036 106, WO 07/068,427). A corresponding boost of action in the case of insecticides has already been described in WO 07/068,428.

The use of ammonium sulphate as a formulating assistant has also been described for certain active compounds and applications (WO 92/16108), but its purpose therein is to stabilize the formulation, not to boost the action.

It has now been found, surprisingly, that the action of insecticides and/or acaricides and/or herbicides from the class of the spiroheterocyclic tetronic acid derivatives of the formula (I) can be boosted significantly through the addition of ammonium salts or phosphonium salts to the application solution or through the incorporation of these salts into a formulation comprising spiroheterocyclic tetronic acid derivatives of the formula (I). The present invention therefore provides for the use of ammonium salts or phosphonium salts for boosting the action of crop protection compositions which comprise as their active compound herbicidal and/or insecticidal and/or acaricidal spiroheterocyclic tetronic acid derivatives of the formula (I). The invention likewise provides compositions which comprise herbicidal and/or acaricidal and/or insecticidal spiroheterocyclic tetronic acid derivatives of the formula (I) and action-boosting ammonium salts or phosphonium salts, including not only formulated active compounds but also ready-to-use compositions (spray liquors). The invention further provides, finally, for the use of these compositions for controlling insect pests and/or spider mites and/or unwanted vegetation.

The compounds of the formula (I) have a broad insecticidal and/or acaricidal and/or herbicidal activity; however, in specific cases the activity and/or compatibility with plants is unsatisfactory.

The active compounds can be used in the compositions according to the invention in a broad concentration range. The concentration of the active compounds in the formulation is typically 0.1%-50% by weight.

Formula (III') provides a definition of the ammonium salts and phosphonium salts which, according to the invention, boost the activity of crop protection compositions comprising compounds of the formula (I)

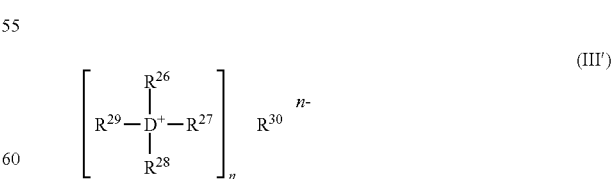

(III')

in which
D represents nitrogen or phosphorus,
D preferably represents nitrogen,
R²⁶, R²⁷, R²⁸ and R²⁹ independently of one another represent hydrogen or in each case optionally substituted $C_1$-$C_8$- alkyl or mono- or polyunsaturated, optionally substituted $C_1$-$C_8$-alkylene, the substituents being selectable from halogen, nitro and cyano, $R_{26}$, $R^{27}$, $R^{28}$ and $R^{29}$ independently of one another preferably represent hydrogen or in each case optionally substituted $C_1$-$C_1$-alkyl, the substituents being selectable from halogen, nitro and cyano, $R^{26}$, $R^{27}$, $R^{28}$ and $R^{29}$ independently of one another particularly preferably represent hydrogen, methyl, ethyl, n-propyl, isopropyl, n-butyl, isobutyl, sec-butyl or tert-butyl, $R^{26}$, $R^{27}$, $R^{28}$ and $R^{29}$ very particularly preferably represent hydrogen, n represents 1, 2, 3 or 4, n preferably represents 1 or 2, $R^{30}$ represents an organic or inorganic anion, $R^{30}$ preferably represents hydrogencarbonate, tetraborate, fluoride, bromide, iodide, chloride, monohydrogenphosphate, dihydrogenphosphate, hydrogensulphate, tartrate, sulphate, nitrate, thiosulphate, thiocyanate, formate, lactate, acetate, propionate, butyrate, pentanoate or oxalate, $R^{30}$ particularly preferably represents lactate, sulphate, nitrate, thiosulphate, thiocyanate, oxalate or formate, $R^{30}$ very particularly preferably represents sulphate.

Inventively emphasized combinations of active compound, salt and penetrant are listed in the table below. Here, "penetrant according to test" means that any compound which acts as penetrant in the cuticle penetration test (Baur et al., 1997, *Pesticide Science* 51, 131-152) is suitable.

The ammonium salts and phosphonium salts of the formula (III') can be used in a broad concentration range to boost the activity of crop protection compositions comprising ketoenoles. In general the ammonium salts or phosphonium salts are used in the ready-to-use crop protection composition in a concentration of 0.5 to 80 mmol/l, preferably 0.75 to 37.5 mmol/l, more preferably 1.5 to 25 mmol/l. In the case of a formulated product the ammonium salt and/or phosphonium salt concentration in the formulation is chosen such that it is within these stated general, preferred or particularly preferred ranges after the formulation has been diluted to the desired active compound concentration. The concentration of the salt in the formulation is typically 1%-50% by weight.

In one preferred embodiment of the invention the activity is boosted by adding to the crop protection compositions not only an ammonium salt and/or phosphonium salt but also, additionally, a penetrant. It is considered entirely surprising that even in these cases an even greater boost to activity is observed. The present invention therefore likewise provides for the use of a combination of penetrant and ammonium salts and/or phosphonium salts to boost the activity of crop protection compositions which comprise insecticidal and/or acaricidal and/or herbicidal spiroheterocyclic tetronic acid derivatives of the formula (I) as active compound. The invention likewise provides compositions which comprise herbicidal and/or acaricidal and/or insecticidal spiroheterocyclic tetronic acid derivatives of the formula (I), penetrants and ammonium salts and/or phosphonium salts, including specifically not only formulated active compounds but also ready-to-use compositions (spray liquors). The invention additionally provides, finally, for the use of these compositions for controlling harmful insects.

In the present context, suitable penetrants are all those substances which are usually employed to improve penetration of agrochemically active compounds into plants. In this context, penetrants are defined in that they penetrate from the aqueous spray liquor and/or the spray coating into the cuticles of the plant, thus increasing the mobility of active compounds in the cuticles. The method described in the literature (Baur et al., 1997, *Pesticide Science* 51, 131-152) can be used for determining this property.

Examples of suitable penetrants include alkanol alkoxylates. Penetrants of the invention are alkanol alkoxylates of the formula (IV')

in which

R represents straight-chain or branched alkyl having 4 to 20 carbon atoms,

R' represents hydrogen, methyl, ethyl, n-propyl, isopropyl, n-butyl, isobutyl, tert-butyl, n-pentyl or n-hexyl, AO represents an ethylene oxide radical, a propylene oxide radical, a butylene oxide radical or represents mixtures of ethylene oxide and propylene oxide radicals or butylene oxide radicals, and v represents a number from 2 to 30.

One preferred group of penetrants are alkanol alkoxylates of the formula

in which

R is as defined above,

R' is as defined above,

EO represents —$CH_2$—$CH_2$—O—, and n represents a number from 2 to 20.

A further preferred group of penetrants are alkanol alkoxylates of the formula

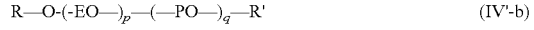

in which

R is as defined above,

R' is as defined above,

EO represents —$CH_2$—$CH_2$—O—,

PO represents

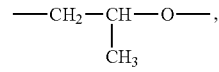

p represents a number from 1 to 10, and q represents a number from 1 to 10,

A further preferred group of penetrants are alkanol alkoxylates of the formula

in which

R is as defined above,

R' is as defined above,

EO represents —$CH_2$—$CH_2$—O—,

PO represents

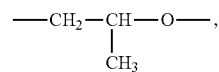

r is a number from 1 to 10, and s is a number from 1 to 10.

A further preferred group of penetrants are alkanol alkoxylates of the formula

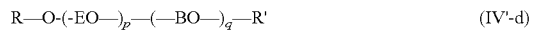

in which
R and R' are as defined above,
EO represents —CH$_2$—CH$_2$—O—,
Bo represents

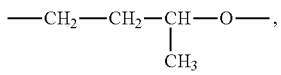

p is a number from 1 to 10 and
q is a number from 1 to 10,

A further preferred group of penetrants are alkanol alkoxylates of the formula $$R—O—(—BO—)_r-(-EO—)_s—R' \quad (IV'-e)$$

in which
R and R' are as defined above.
BO represents

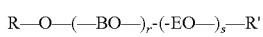

EO represents
r represents a number from 1 to 10 and
s represents a number from 1 to 10, A further preferred group of penetrants are alkanol alkoxylates of the formula $$CH_3—(CH_2)_t—CH_2—O—(—CH_2—CH_2—O—)_u—R' \quad (IV'-f)$$

in which
R' is as defined above,
t represents a number from 6 to 13,
u represents a number from 6 to 17.

In the formulae indicated above,
R preferably represents butyl, isobutyl, n-pentyl, isopentyl, neopentyl, n-hexyl, isohexyl, n-octyl, isooctyl, 2-ethylhexyl, nonyl, isononyl, decyl, n-dodecyl, iododecyl, lauryl, myristyl, isotridecyl, trimethylnonyl, palmityl, stearyl or eicosyl.

As an example of an alkanol alkoxylate of the formula (IV'-c) mention may be made of 2-ethylhexyl alkoxylate of the formula

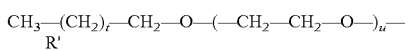

in which
EO represents —CH, —CH$_2$—O—,
PO represents

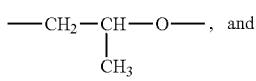

the numbers 8 and 6 represent average values.

As an example of an alkanol alkoxylate of the formula (IV'-d) mention may be made of the formula

in which
EO represents —CH$_2$—CH$_2$—O—,
BO represents

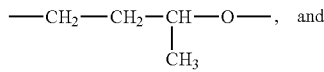

the numbers 10, 6 and 2 represent average values.

Particularly preferred alkanol alkoxylates of the formula (IV'-f) are compounds of this formula in which
t represents a number from 9 to 12 and
u represents a number from 7 to 9.

Mention may be made with very particular preference of alkanol alkoxylate of the formula (IV'-f-1)

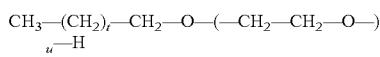

in which
t represents the average value 10.5 and
u represents the average value 8.4.

A general definition of the alkanol alkoxylates is given by the formulae above. These substances are mixtures of compounds of the stated type with different chain lengths. The indices therefore have average values which may also deviate from whole numbers.

The alkanol alkoxylates of the formulae stated are known and in some cases are available commercially or can be prepared by known methods (cf. WO 98/35 553, WO 00/35 278 and EP-A 0 681 865).

Suitable penetrants also include, for example, substances which promote the availability of the compounds of the formula (I) in the spray coating. These include, for example, mineral or vegetable oils. Suitable oils are all mineral or vegetable oils—modified or otherwise—which can typically be used in agrochemical compositions. Mention may be made by way of example of sunflower oil, rapeseed oil, olive oil, castor oil, colza oil, maize seed oil, cotton seed oil and soya bean oil, or the esters of said oils. Preference is given to rapeseed oil, sunflower oil and their methyl or ethyl esters.

The concentration of penetrant in the compositions of the invention can be varied within a wide range. In the case of a formulated crop protection composition it is in general 1% to 95%, preferably 1% to 55%, more preferably 15%-40% by weight. In the ready-to-use compositions (spray liquors) the concentrations are generally between 0.1 and 10 g/l, preferably between 0.5 and 5 g/l.

Crop protection compositions of the invention may also comprise further components, examples being surfactants and/or dispersing assistants or emulsifiers.

Suitable nonionic surfactants and/or dispersing assistants include all substances of this type that can typically be used in agrochemical compositions. Preferably mention may be made of polyethylene oxide-polypropylene oxide block copolymers, polyethylene glycol ethers of linear alcohols, reaction products of fatty acids with ethylene oxide and/or propylene oxide, and also polyvinyl alcohol, polyvinylpyrrolidone, copolymers of polyvinyl alcohol and polyvinylpyrrolidone, and copolymers of (meth)acrylic acid and (meth)acrylic esters, and additionally alkyl ethoxylates and alkylaryl ethoxylates, which optionally may be phosphated and optionally may be neutralized with bases, mention being made, by way of example, of sorbitol ethoxylates, and, as well, polyoxyalkylenamine derivatives.

Suitable anionic surfactants include all substances of this type that can typically be used in agrochemical compositions.

Preference is given to alkali metal salts and alkaline earth metal salts of alkylsulphonic acids or alkylarylsulphonic acids.

A further preferred group of anionic surfactants and/or dispersing assistants are the following salts that are of low solubility in plant oil: salts of polystyrenesulphonic acids, salts of polyvinylsulphonic acids, salts of naphthalenesulphonic acid-formaldehyde condensation products, salts of condensation products of naphthalenesulphonic acid, phenolsulphonic acid and formaldehyde, and salts of lignosulphonic acid.

Suitable additives which may be included in the formulations of the invention are emulsifiers, foam inhibitors, preservatives, antioxidants, colorants and inert filling materials.

Preferred emulsifiers are ethoxylated nonylphenols, reaction products of alkylphenols with ethylene oxide and/or propylene oxide, ethoxylated arylalkylphenols, and also ethoxylated and propoxylated arylalkylphenols, and also sulphated or phosphated arylalkyl ethoxylates and/or arylalkyl ethoxypropoxylates, mention being made by way of example of sorbitan derivatives, such as polyethylene oxide-sorbitan fatty acid esters, and sorbitan fatty acid esters.

Using, for example, according to process (A) ethyl O-[(2,4,6-trimethyl)phenylacetyl]-4-hydroxy-1-methoxypiperidine-4-carboxylate as starting material, the course of the process according to the invention can be represented by the reaction scheme below:

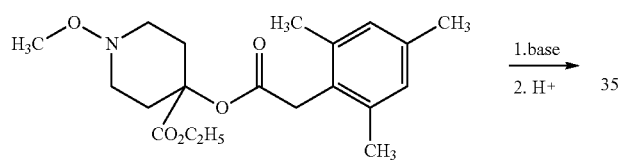

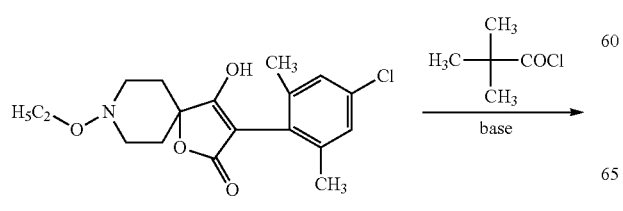

Using, for example, according to process (Bα) 8-ethoxy-3-[(4-chloro-2,6-dimethyl)phenyl]-1-oxa-8-azaspiro[4,5]decane-2,4-dione or its enol and pivaloyl chloride as starting materials, the course of the process according to the invention can be represented by the reaction scheme below:

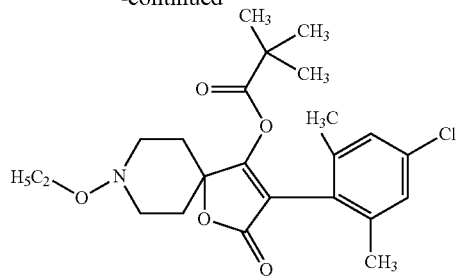

Using, for example, according to process (B) (variant β) 8-methoxy-3-[(2,4-dichloro)phenyl]-1-oxa-8-azaspiro[4,5]decane-2,4-dione or its enol and acetic anhydride as starting materials, the course of the process according to the invention can be represented by the reaction scheme below:

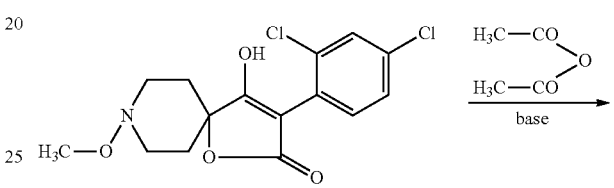

Using, for example, according to process (C) 8-methoxy-3-[(2,4-dichloro-6-methyl)phenyl]-1-oxa-8-azaspiro[4,5]decane-2,4-dione or its enol and ethyl chloroformate as starting materials, the course of the process according to the invention can be represented by the reaction scheme below:

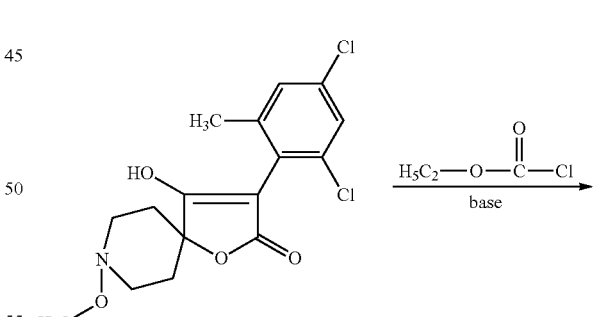

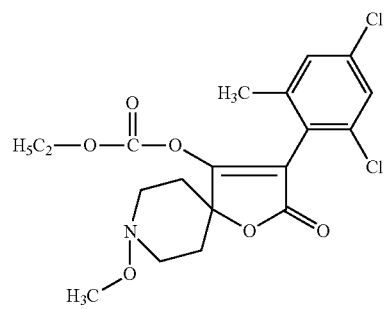

Using, for example, according to process (D) 8-ethoxy-3-[(2,4,6-trimethyl)phenyl]-1-oxa-8-aza-spiro[4,5]decane-2,4-dione or its enol and methyl chloromonothioformate as starting materials, the course of the reaction can be represented as follows:

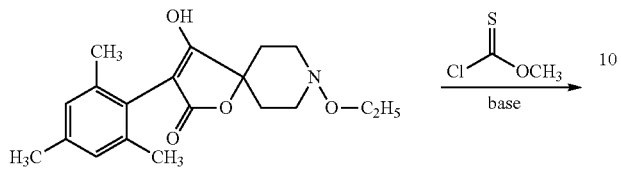

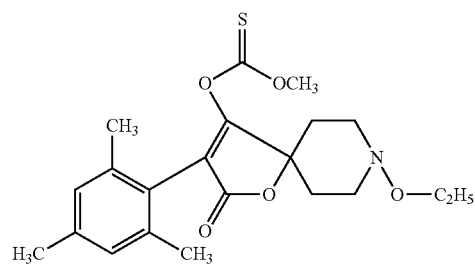

Using, for example, according to process (E) 8-methoxy-3-[(2,4,6-trimethyl)-phenyl]-1-oxa-8-azaspiro[4,5]decane-2,4-dione or its enol and methanesulphonyl chloride as starting materials, the course of the reaction can be represented by the reaction scheme below:

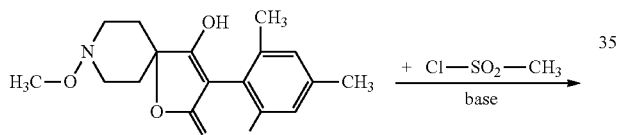

Using, for example, according to process (F) 8-ethoxy-3-[(2,4-dichloro-6-methyl)phenyl]-1-oxa-8-azaspiro[4,5]decane-2,4-dione or its enol and 2,2,2-trifluorethyl methanethiophosphonyl chloride as starting materials, the course of the reaction can be represented by the reaction scheme below:

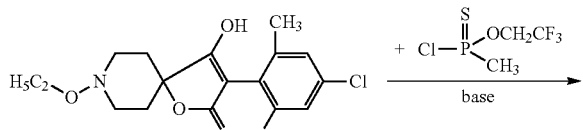

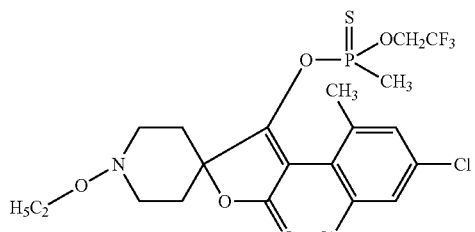

Using, for example, according to process (G) 8-methoxy-3-[(2,3,4,6-tetramethylphenyl]-1-oxo-8-azaspiro[4,5]decane-2,4-dione or its enol and NaOH as components, the course of the process according to the invention can be represented by the scheme below:

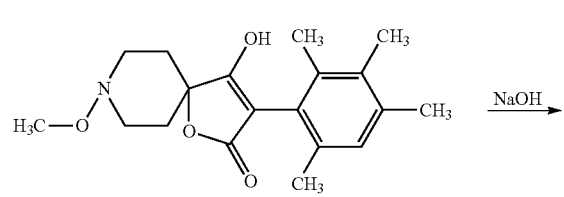

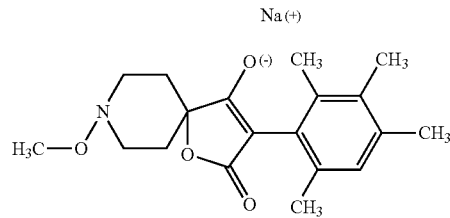

Using, for example, according to process (H) (variant α) 8-methoxy-3-[(2,4,5-trimethyl)phenyl]-1-oxa-8-azaspiro[4,5]decane-2,4-dione or its enol and ethyl isocyanate as starting materials, the course of the reaction can be represented by the scheme below:

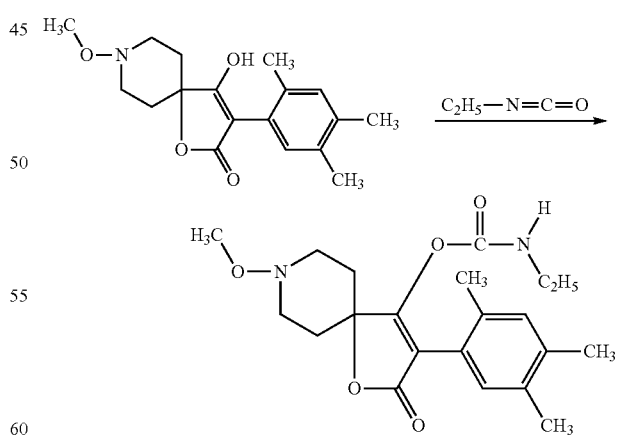

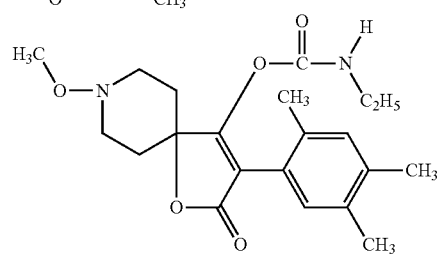

Using, for example, according to process (a) (variant β) 8-methoxy-3-[(2,4,6-trimethyl)phenyl]-1-oxa-8-azaspiro[4,5]decane-2,4-dione or its enol and dimethylcarbamoyl chloride as starting materials, the course of the reaction can be represented by the scheme below:

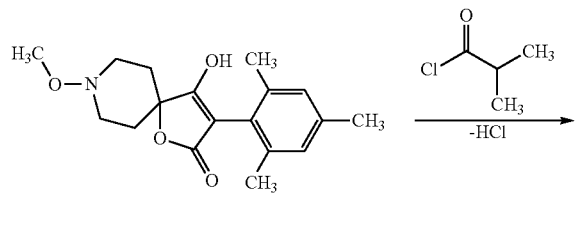
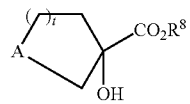

The acylhydroxycarboxylic esters of the formula (II) are obtained, for example, when hydroxycarboxylic acid derivatives of the formula (XIV)

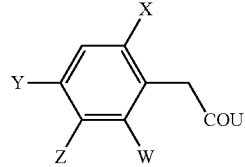

(XIV)

in which
A, t and $R^8$ have the meaning given above,
are acylated with substituted phenylacetic acid derivatives of the formula (XV)

(XV)

in which
W, X, Y and Z have the meanings given above and
U represents a leaving group introduced by carboxylic acid activating reagents such as carbonyldiimidazole, carbonyldiimides (for example dicyclohexylcarbodiimide), phosphorylating reagents (for example $POCl_3$, BOP—Cl), halogenating agents, e.g. thionyl chloride, oxalyl chloride, phosgene or chloroformic esters,
(Chem. Reviews 52, 237-416 (1953).

The compounds of the formula (XIV) are novel. The phenylacetic acid derivatives of the formula (XV) are known from the patent applications cited at the outset or can be prepared by the processes described therein.

The acid halides of the formula (III), carboxylic anhydrides of the formula (IV), chloroformic esters or chloroformic thioesters of the formula (V), chloromonothioformic esters or chlorodithioformic esters of the formula (VI), sulphonyl chlorides of the formula (VII), phosphorus compounds of the formula (VIII) and metal hydroxides, metal alkoxides or amines of the formulae (IX) and (X) and isocyanates of the formula (XI) and carbamoyl chlorides of the formula (XII) and boronic acids of the formula (XIII) furthermore required as starting materials for carrying out the processes (B), (C), (D), (E), (F), (G), (H) and (I) according to the invention are generally known compounds of organic of inorganic chemistry.

The compounds of the formula (I-a'-I-g') and (I-a"-I-g") can be prepared by the processes A to H described.

The compounds of the formulae (XIIIα) and (XIIIβ) are known from the literature.

The process (A) is characterized in that compounds of the formula (II), in which A, t, W, X, V, Z and $R^8$ have the meanings given above, are subjected to an intramolecular condensation in the presence of a base.

Suitable for use as diluents in the process (A) according to the invention are all organic solvents which are inert towards the reaction participants. Preference is given to using hydrocarbons, such as toluene and xylene, furthermore ethers, such as bibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone. It is furthermore possible to use alcohols, such as methanol, ethanol, propanol, isopropanol, butanol, isobutanol, tert-butanol.

Using, for example, according to process (Iβ) 8-methoxy-3-[(4-bromo-2,6-dimethylphenyl)]-1-oxa-8-azaspiro[4,5]decane-2,4-dione or its enol and 4-chlorophenylboronic acid as starting materials, the course of the reaction can be represented by the scheme below:

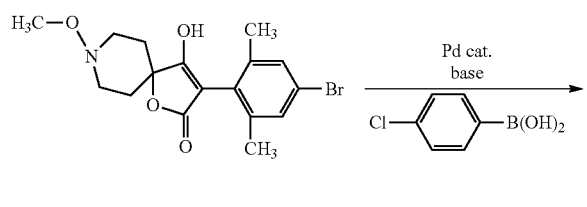

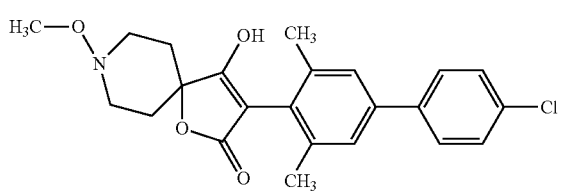

The compounds, required as starting materials for the process (A) according to the invention, of the formula (II)

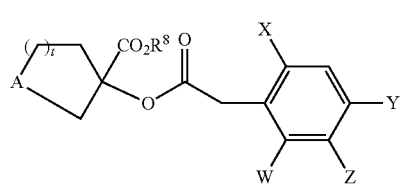

(II)

in which
A, t, W, X, Y, Z and $R^8$ have the meanings given above,
are novel.

Suitable bases (deprotonating agents) for carrying out the process (A) according to the invention are all customary protonic ceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which may also be used in the presence of phase-transfer catalysts, such as, for example, triethylbenzylammonium chloride, tetrabutyl ammonium bromide, Adogen 464 (=methyltrialkyl(C18-C10)ammonium chloride) or TDA 1 (=tris(methoxyethoxyethyl)amine). It is furthermore possible to use alkali metals, such as sodium or potassium. Further, it is possible to employ alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (A) according to the invention, the reaction temperatures may be varied within a relatively wide range. In general, the process is carried out at temperatures between −75° C. and 200° C., preferably between −50° C. and 150° C. The process (A) according to the invention is generally carried out under atmospheric pressure.

When carrying out the process (A) according to the invention, the reaction components of the formula (II) and the deprotonating bases are generally employed in about doubly equimolar amounts. However, it is also possible to use a relatively large excess (up to 3 mol) of one component or the other.

The process ($B_\alpha$) is characterized in that compounds of the formula (I-a) are in each case reacted with carbonyl halides of the formula (III), if appropriate in the presence of a diluent and if appropriate in the presence of an acid binder.

Suitable for use as diluents in the process ($B_\alpha$) according to the invention are all solvents which are inert towards the acid halides. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorbenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholan. If the acid halide is sufficiently stable to hydrolysis, the reaction can also be carried out in the presence of water.

Suitable acid binders for the reaction according to process ($B_\alpha$) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig-Base and N,N-dimethylaniline, furthermore alkaline earth metal oxides, such as magnesium oxide and calcium oxide, moreover alkali metal carbonates and alkaline earth metal carbonates, such as sodium carbonate, potassium carbonate and calcium carbonate, and also alkali metal hydroxides, such as sodium hydroxide and potassium hydroxide.

The reaction temperatures in the process ($B_\alpha$) according to the invention can be varied within a relatively wide range. In general, the process is carried out at temperatures between −20° C. and +150° C., preferably between 0° C. and 100° C.

When carrying out the process ($B_\alpha$) according to the invention, the starting materials of the formula (I-a) and the carbonyl halide of the formula (III) are generally each employed in approximately equivalent amounts. However, it is also possible to use a relatively large excess (up to 5 mol) of the carbonyl halide. Work-up is carried out by customary methods.

The process ($B_\beta$) is characterized in that compounds of the formula (I-a) are reacted with carboxylic anhydrides of the formula (IV), if appropriate in the presence of a diluent and if appropriate in the presence of an acid binder.

Suitable diluents for use in the process ($B_\beta$) according to the invention are, preferably, the diluents which are also preferred when using acid halides. Besides this a carboxylic anhydride used in excess may simultaneously act as diluent.

Suitable acid binders, which are added, if appropriate, for process ($B_\beta$) are, preferably, the acid binders which are also preferred when using acid halides.

The reaction temperatures in the process ($B_\beta$) according to the invention may be varied within a relatively wide range. In general, the process is carried out at temperatures between −20° C. and +150° C., preferably between 0° C. and 100° C.

When carrying out the process ($B_\beta$) according to the invention, the starting materials of the formula (I-a) and the carboxylic anhydride of the formula (IV) are generally each employed in approximately equivalent amounts. However, it is also possible to use a relatively large excess (up to 5 mol) of carboxylic anhydride. Work-up is carried out by customary methods.

In general, diluent and excess carboxylic anhydride and the carboxylic acid formed are removed by distillation or by washing with an organic solvent or with water.

The process (C) is characterized in that compounds of the formula (I-a) are in each case reacted with chloroformic esters or chloroformic thin esters of the formula (V), if appropriate in the presence of a diluent and if appropriate in the presence of an acid binder.

Suitable acid hinders for the reaction according to the process (C) according to the invention are all customary acid acceptors. Preference is given to use tertiary amines, such as triethylamine, pyridine, DABCO, DBU, DBA, Hünig-Base and N,N-dimethylaniline, furthermore, alkaline earth metal oxides, such as magnesium oxide and calcium oxide, moreover alkali metal carbonates and alkaline earth metal carbonates, such as sodium carbonate, potassium carbonate and calcium carbonate, and also alkali metal hydroxides, such as sodium hydroxide and potassium hydroxide.

Suitable diluents for use in the process (C) according to the invention are all solvents which are inert towards the chloroformic esters or chloroformic thin esters. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholane.

When carrying out the process (C) according to the invention, the reaction temperatures can be varied within a relatively wide range. If the process is carried out in the presence of a diluent and an acid binder, the reaction temperatures are generally between −20° C. and +100° C., preferably between 0° C. and 50° C.

The process (C) according to the invention is generally carried out under atmospheric pressure.

When carrying out the process (C) according to the invention, the starting materials of the formula (I-a) and the appropriate chloroformic ester or chloroformic thio ester of the formula (V) are generally each employed in approximately equivalent amounts. However, it is also possible to use a relatively large excess (up to 2 mol) of one component or the other. Work-up is carried out by customary methods. In general, precipitated salts are removed and the reaction mixture that remains is concentrated by removing the diluent under reduced pressure.

The process (D) according to the invention is characterized in that compounds of the formula (I-a) are in each case reacted with compounds of the formula (VI) in the presence of a diluent and, if appropriate, in the presence of an acid binder.

In preparation process (D), about one mol of chloromonothioformic ester or chlorodithioformic ester of the formula (VI) is employed per mole of the starting material of the formula (I-a) at from 0 to 120° C., preferably from 20 to 60° C.

Suitable diluents which are added, if appropriate, are all inert polar organic solvents, such as ethers, amides, sulphones, sulphoxides, and also halogenated alkanes.

Preference is given to using dimethyl sulphoxide, tetrahydrofuran, dimethylformamide or methylene chloride.

If, in a preferred embodiment, the enolate salt of the compounds (I-a) is prepared by addition of strong deprotonating agents, such as, for example, sodium hydride or potassium tert-butoxide, the further addition of acid binders may be dispensed with.

Suitable bases for process (D) are all customary proton acceptors. Preference is given to using alkali metal hydrides, alkali metal alkoxides, alkali metal or alkaline earth metal carbonates or bicarbonates or nitrogen bases. Sodium hydride, sodium methoxide, sodium hydroxide, calcium hydroxide, potassium carbonate, sodium bicarbonate, triethylamine, dibenzylamine, diisopropylamine, pyridine, quinoline, diazabicyclooctane (DABCO), diazabicyclononene (DBN) and diazabicycloundecene (DBU) may be mentioned by way of example.

The reaction can be carried out at atmospheric pressure or under elevated pressure and is preferably carried out at atmospheric pressure. Work-up is carried out by customary methods.

The process (E) according to the invention is characterized in that compounds of the formula (I-a) are in each case reacted with sulphonyl chlorides of the formula (VII), if appropriate in the presence of a diluent and if appropriate in the presence of an acid binder.

In preparation process (E), about one mol of sulphonyl chloride of the formula (VII) is reacted per mole of the starting material of the formula (I-a) at from −20 to 150° C., preferably from 0 to 70° C.

Process (E) is preferably carried out in the presence of a diluent.

Suitable diluents are all inert polar organic solvents, such as ethers, amides, nitrides, sulphones, sulphoxides or halogenated hydrocarbons, such as methylene chloride.

Preference is given to using dimethyl sulphoxide, tetrahydrofuran, dimethylformamide, methylene chloride.

If, in a preferred embodiment, the enolate salt of the compounds (I-a) is prepared by addition of strong deprotonating agents (such as, for example, sodium hydride or potassium tert-butoxide), the further addition of acid binders may be dispensed with.

If acid binders are used, these are customary inorganic or organic bases, for example sodium hydroxide, sodium carbonate, potassium carbonate, pyridine and triethylamine.

The reaction can be carried out at atmospheric pressure or under elevated pressure and is preferably carried out at atmospheric pressure. Work-up is carried out by customary methods.

The process (F) according to the invention is characterized in that compounds of the formula (I-a) are in each case reacted with phosphorus compounds of the formula (VIII), if appropriate in the presence of a diluent and if appropriate in the presence of an acid binder.

In preparation process (F), to obtain compounds of the formula (I-e), from 1 to 2, preferably from 1 to 1.3, mol of the phosphorus compound of the formula (VIII) are reacted per mole of the compounds of the formula (I-a), at temperatures between −40° C. and 150° C., preferably between −10 and 110° C.

Process (F) is preferably carried out in the presence of a diluent.

Suitable diluents are all inert polar organic solvents, such as ethers, carboxylic esters, halogenated hydrocarbons, ketones, amides, nitriles, sulphones, sulphoxides, etc.

Preference is given to using acetonitrile, dimethyl sulphoxide, tetrahydrofuran, dimethylformamide, methylene chloride.

Suitable acid binders which are added, if appropriate, are customary inorganic or organic bases, such as hydroxides, carbonates or amines. Sodium hydroxide, sodium carbonate, potassium carbonate, pyridine and triethylamine may be mentioned by way of example.

The reaction can be carried out at atmospheric pressure or under elevated pressure and is preferably carried out at atmospheric pressure. Work-up is carried out by customary methods of organic chemistry. The arising end products are preferably purified by crystallization, chromatographic purification or "incipient distillation" i.e. removal of the volatile components under reduced pressure.

The process (G) is characterized in that compounds of the formula (I-a) are in each case reacted with metal hydroxides or metal alkoxides of the formula (IX) or amines of the formula (X), if appropriate in the presence of a diluent.

Suitable diluents for use in the process (G) according to the invention are, preferably, ethers, such as tetrahydrofuran, dioxane, diethyl ether, or else alcohols, such as methanol, ethanol, isopropanol, and also water. The process (G) according to the invention is generally carried out under atmospheric pressure. The reaction temperatures are generally between −20° C. and 100° C., preferably between 0° C. and 50° C.

The process (H) according to the invention is characterized in that compounds of the formula (I-a) are in each case reacted with (Hα) compounds of the formula (XI), if appropriate in the presence of a diluent and if appropriate in the presence of a catalyst, or (Hβ) with compounds of the formula (XII), if appropriate in the presence of a diluent and if appropriate in the presence of an acid binder.

In preparation process (Hα), about 1 mol of isocyanate of the formula (XI) is reacted per mole of starting material of the formula (I-a), at from 0 to 100° C., preferably from 20 to 50° C.

Process (Hα) is preferably carried out in the presence of a diluent.

Suitable diluents are all inert organic solvents, such as aromatic hydrocarbons, halogenated hydrocarbons, ethers, amides, nitrides, sulphones or sulphoxides.

If appropriate, catalysts may be added to accelerate the reaction. Suitable for use as catalysts are, very advantageously, organotin compounds, such as, for example dibutyl tin dilaurate.

The reaction is preferably carried out at atmospheric pressure.

In preparation process (H-β), about 1 mol of carbamoyl chloride of the formula (XII) is reacted per mole of starting material of the formula (I-a), at from 0 to 150° C., preferably at from 20 to 70° C.

Suitable diluents which are added, if appropriate, are all inert polar organic solvents, such as ethers, carboxylic esters, nitriles, ketones, amides, sulphones, sulphoxides or halogenated hydrocarbons.

Preference is given to using dimethyl sulphoxide, tetrahydrofuran, dimethylformamide or methylene chloride.

If, in a preferred embodiment, the enolate salt of the compound of the formula (I-a) is prepared by addition of strong deprotonating agents (such as, for example, sodium hydride or potassium tert-butoxide), the further addition of acid binders may be dispensed with.

If acid binders are used, then customary inorganic or organic bases are suitable, for example sodium hydroxide, sodium carbonate, potassium carbonate, triethylamine or pyridine.

The reaction can be carried at an atmospheric pressure or under elevated pressure and is preferably carried out at atmospheric pressure. Work-up is carried out by customary methods.

Suitable catalysts for carrying out the processes (Iα) and (Iβ) according to the invention are palladium(0) complexes. Preference is given, for example, to tetrakis(triphenylphosphine)-palladium, if appropriate, it is also possible to use palladium(III) compounds, for example $PdCl_2$, $Pd(OAc)_2$. If palladium(II) compounds are used, phosphines, such as, for example, tricyclehexyl-phosphine, are generally employed as complex formers.

Suitable acid acceptors for carrying out the processes (Iα) and (Iβ) according to the invention are inorganic or organic bases. These preferably include alkaline earth metal or alkali metal hydroxides, acetates, carbonates or bicarbonates, such as, for example, sodium hydroxidem, potassium hydroxide, barium hydroxide or ammonium hydroxide, sodium acetate, potassium acetate, calcium acetate or ammonium acetate, sodium carbonate, potassium carbonate, caesium carbonate or ammonium carbonate, sodium bicarbonate or potassium bicarbonate, alkali metal fluorides, such as, for example, caesium fluoride, alkali metal phosphates, such as, for example, potassium dihydrogen phosphate, potassium phosphate and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Suitable diluents for carrying out the processes (Iα) and (Iβ) according to the invention are water, organic solvents and any mixtures thereof. There may be mentioned by way of example: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloroethane, trichloroethane or tetrachloroethylene; ethers, such as diethyl ether, diisopropyl ether, methyl t-butyl ether, methyl t-amyl ether, dioxane, tetrahydrofuran, 1,2-dimethoxyethane, 1,2-diethoxyethane, diethylene glycol dimethyl ether or anisole; alcohols, such as methanol, ethanol, n- or isopropanol, n-, iso-, sec- or tert-butanol, ethanediol, propane-1,2-diol, ethoxyethanol, methoxyethanol, diethylene glycol monomethyl ether, diethylene glycol monomethyl ether, water.

In the processes (Iα) and (Iβ) according to the invention, the reaction temperature can be varied within a relatively wide range. In general, the process is carried out at temperatures between 0° C. and +140° C., preferably between 50° C. and +100° C.

When carrying out the processes (Iα) and (Iβ) according to the invention, the boronic acids of the formulae (XIIIα) and (XIIIβ) in which Y and Z have the meaning given above and compounds of the formulae (I-a') to (I-g') in which A, t, G, W, X, Y and Z' have the meaning given above and the compounds of the formulae (I-a") to (I-g") in which A, t, G, W, X, Z and Y' have the meaning given above are employed in a molar ratio of from 1:1 to 3:1, preferably of from 1:1 to 2:1. In general, from 0.005 to 0.5 mol, preferably from 0.01 mol to 0.1 mol, of catalyst are employed per mole of the compounds of the formulae (I-a') to (I-g') or (I-a") to (I-g"). The base is generally employed in excess. Work-up is carried out by customary methods The active compounds of the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluses, which are encountered in agriculture, in horticulture, in animal husbandry, in forests, in gardens and leisure facilities, in the protection of stored products and of materials, and in the hygiene sector. They may be preferably employed as crop protection agents. They are active against normally sensitive and resistant species and against all or some stages of development. The abovementioned pests include:

From the phylum Mollusca, for example from the class of the Lamellibranchiata, for example *Dreissena* spp.

From the class of the Gastropoda, for example *Anion* spp., *Biomphalaria* spp., *Bulinus* spp., *Deroceras* spp., *Galba* spp., *Lymnaea* spp., *Oncomelania* spp., *Pomacea* spp., *Succinea* spp.

From the phylum Arthropoda, for example from the order of the Isopoda, for example Armadillidium vulgare, Oniscus asellus, Porcellio scaber.

From the class of the Arachnida, for example *Acarus* spp., *Aceria sheldoni, Aculops* spp., *Aculus* spp., *Amblyomma* spp., *Amphitetranychus viennensis, Argas* spp., *Boophilus* spp., *Brevipalpus* spp., *Bryobia praetiosa, Centruroides* spp., *Chorioptes* spp., *Dermanyssus gallinae, Dermatophagoides pteronyssius, Dermatophagoides farinae, Dermacentor* spp., *Eotetranychus* spp., *Epitrimerus pyri, Eutetranychus* spp., *Eriophyes* spp., *Halotydeus destructor, Hemitarsonemus* spp., *Hyalomma* spp., *Ixodes* spp., *Latrodectus* spp., *Loxosceles* spp., *Metatetranychus* spp., *Nuphersa* spp., *Oligonychus* spp., *Ornithodoros* spp., *Ornithonyssus* spp., *Panonychus* spp., *Phyllocoptruta oleivora, Polyphagotarsonemus latas, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vaejovis* spp., *Vasates lycopersici*.

From the order of the Symphyla, for example *Scutigerella* spp.

From the order of the Chilopoda, for example *Geophilus* spp., *Scutigera* spp.

From the order of the Collembola, for example *Onychiurus armatus*.

From the order of the Diplopoda, for example *Blaniulus guttulatus*.

From the order of the Zygentoma, for example *Lepisma saccharina, Thermobia domestica*.

From the order of the Orthoptera, for example *Acheta domesticus, Blatta orientalis, Blattella germanica, Dichroplus* spp., *Gryllotalpa* spp., *Leucophaea maderae, Locusta* spp., *Melanoplus* spp., *Periplaneta* spp., *Pulex irritans, Schistocerca gregaria, Supella longipalpa.*

From the order of the Isoptera, for example *Coptotermes* spp., *Cornitermes cumulans, Cryptoteimes* spp., *Incisitermes* spp., *Microtermes obesi, Odontotermes* spp., *Reticulitermes* spp., From the order of the Heteroptera, for example *Anasa tristis, Antestiopsis* spp., *Boisea* spp., *Blissus* spp., *Calocoris* spp., *Campylomma livida, Cavelerius* spp., *Cimex lectularius, Collaria* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Monalonion atratum, Nezara* spp., *Oebalus* spp., *Pentomidae, Piesma quadrata, Piezodorus* spp., *Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.

From the order of the Anoplura (Phthiraptera), for example *Damalinia* spp., *Haematopinus* spp., *Linognathus* spp., *Pediculus* spp., *Ptirus pubis, Trichodectes* spp.

From the order of the Homoptera, for example *Acyrthosipon* spp., *Acrogonia* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus, Ferrisia* spp., *Geococcus coffeae, Hieroglyphus* spp., *Homalodisca coagulata, Hyalopterus arundinis, Icerya* spp., *Idiocerus* spp., idioscopus spp., Lao-delphax striatellus, *Lecanium* spp., *Lepidosaphes* spp., *Lipaphis erysimi, Macrosiphum* spp., *Mahanarva* spp., *Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes* spp., *Trioza* spp., *Typhlocyba* spp., *Unaspis* spp., *Viteus vitifolii, Zygina* spp.

From the order of the Coleoptera, for example *Acalymma vittatum, Acanthoscelides obtectus, Adoretus* spp., *Agelastica alni, Agriotes* spp., *Alphitobius diaperinus, Amphimallon solstitialis, Anobium punctatum, Anoplophora* spp., *Anthonomus* spp., *Anthrenus* spp., *Apion* spp., *Apogonia* spp., *Atomaria* spp., *Attagenus* spp., *Bruchidius obtectus, Bruchus* spp., *Cassida* spp., *Cerotoma trifurcata, Ceutorrhynchus* spp., *Chaetocnema* spp., *Cleonus mendicus, Conoderus* spp., *Cosmopolites* spp., *Costelytra zealandica, Ctenicera* spp., *Curculio* spp., *Cryptorhynchus lapathi, Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides, Hellula undalis, Heteronychus arator, Heteronyx* spp., *Hylamorpha elegans, Hylotrupes bajulus, Hypera postica, Hypothenemus* spp., *Lachnosterna consanguinea, Lema* spp., *Leptinotarsa decemlineata, Leucoptera* spp., *Lisso-rhoptrus oryzophilus, Lixus* spp., *Luperodes* spp., *Lyctus* spp., *Megascelis* spp., *Melanotus* spp., *Meligethes aeneus, Melolontha* spp., *Migdolus* spp., *Monochamus* spp., *Naupactus xanthographus, Niptus hololeucus, Oryctes rhinoceros, Oryzaephilus surinamensis, Oryzaphagus oryzae, Otiorrhynchus* spp., *Oxycetonia jucunda, Phaedon cochleariae, Phyllophaga* spp., *Phyllotreta* spp., *Popillia japonica, Premnotrypes* spp., *Prostephanus truncatus, Psylliodes* spp., *Ptinus* spp., *Rhizobius ventralis, Rhizopertha dominica, Sitophilus* spp., *Sphenophorus* spp., *Stegobium paniceum, Sternechus* spp., *Symphyletes* spp., *Tanymecus* spp., *Tenebrio molitor, Tribolium* spp., *Trogoderma* spp., *Tychius* spp., *Xylotrechus* spp., *Zabrus* spp.

From the order of the Hymenoptera, for example *Acromyrmex* spp., *Athalia* spp., *Atta* spp., *Diprion* spp., *Hoplocampa* spp., *Lasius* spp., *Monomorium pharaonis, Solenopsis invicta, Tapinoma* spp., *Vespa* spp.

From the order of the Lepidoptera, for example *Acronicta major, Adoxophyes* spp., *Aedia leucomelas, Agrotis* spp., *Alabama* spp., *Amyelois transitella, Anarsia* spp., *Anticarsia* spp., *Argyroploce* spp., *Barathra brassicae, Borbo cinnara, Bucculatrix thurberiella, Bupalus piniarius, Eiusseola* spp., *Cacoecia* spp., *Caloptilia theivora, Capua reticulana, Carpocapsa pomonella, Carposina niponensis, Chematobia brumata, Chilo* spp., *Choristoneura* spp., *Clysia ambiguella, Cnaphalocerus* spp., *Cnephasia* spp., *Conopomorpha* spp., *Conotrachelus* spp., *Copitarsia* spp., *Cydia* spp., *Dalaca noctuides, Diaphania* spp., *Diatraea saccharalis, Earias* spp., *Ecdytolopha aurantium, Elasmopalpus lignosellus, Eldana saccharina, Ephestia* spp., *Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Heliothis* spp., *Hofmannophila pseudospretella, Homoeosoma* spp., *Homona* spp., *Hyponomeuta padella, Kakivoria flavofasciata, Laphygma* spp., *Laspeyresia molesta, Leucinodes orbonalis, Leucoptera* spp., *Lithocolletis* spp., *Lithophane antennata, Lobesia* spp., *Loxagrotis albicosta, Lymantria* spp., *Lyonetia* spp., *Malacosoma neustria, Maruca testulalis, Mamestra brassicae, Mocis* spp., *Mythimna separata, Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., Pier's spp., *Platynota stultana, Plodia interpunctella, Plusia* spp., *Plutella xylostella, Prays* spp., *Prodenia* spp., *Protoparce* spp., *Pseudaletia* spp., *Pseudoplusia includens, Pyrausta nubilalis, Rachiplusia nu, Schoenobius* spp., *Scirpophaga* spp., *Scotia segetum, Sesamia* spp., *Sparganothis* spp., *Spodoptera* spp., *Stathmopoda* spp., *Stomopteryx subsecivella, Synanthedon* spp., *Tecia solanivora, Thermesia gemmatalis, Tinea pellionella, Tineola bisselliella, Tortrix* spp., *Trichophaga tapetzella, Trichoplusia* spp., *Tuta absoluta, Virachola* spp.

From the order of the Diptera, for example *Aedes* spp., *Agromyza* spp., *Anastrepha* spp., *Anopheles* spp., *Asphondylia* spp., *Bactrocera* spp., *Bibio hortulanus, Calli*-

*phora erythrocephala, Ceratitis capitata, Chironomus* spp., *Chrysomyia* spp., *Chrysops* spp., *Cochliomyia* spp., *Contarinia* spp., *Cordylobia anthropophaga, Culex* spp., *Culicoides* spp., *Culiseta* spp., *Cuterebra* spp., *Dacus oleae, Dasyneura* spp., *Delia* spp., *Dermatobia hominis, Drosophila* spp., *Echinocnemus* spp., *Fannia* spp., *Gasterophilus* spp., *Glossina* spp., *Haematopota* spp., *Hydrellia* spp., *Hylemyia* spp., *Hyppobosca* spp., *Hypoderma* spp., *Lirlomyza* spp. *Lucilia* spp., *Lutzomia* spp., *Mansonia* spp., *Musca* spp., *Nezara* spp., *Oestrus* spp., *Oscinella frit, Pegomyia* spp., *Phlebotomus* spp., *Phorbia* spp., *Phormia* spp., *Prodiplosis* spp., *Psila rosae, Rhagoletis* spp., *Sarcophaga* spp., *Simulium spp, Stomoxys* spp., *Tabanus* spp., *Tannia* spp., *Tetanops* spp., *Tipula* spp.

From the order of the Thysanoptera, for example *Anaphothrips obscurus, Baliothrips biformis, Drepanothris reuteri, Enneothrips flavens, Frankliniella* spp., *Heliothrips* spp., *Hercinothrips femoralis, Rhipiphorothrips cruentatus, Scirtothrips* spp., *Taeniothrips cardamoni, Thrips* spp.

From the order of the Siphonaptera, for example *Ceratophyllus* spp., *Ctenocephalides* spp., *Tunga penetrans, Xenopsylla cheopis*.

From the phyla of the Plathelminthes and Nematodes as animal parasites, for example from the class of the Helminthes, for example *Ancylostoma duodenale, Ancylostoma ceylanicum, Acylostoma braziliensis, Ancylostoma* spp., *Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp, *Strongyloides fuellebomi, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti*.

From the phylum of the Nematodes as plant pests, for example *Aphelenchoides* spp., *Bursa-phelenchus* spp., *Ditylenchus* spp., *Globodera* spp., *Heterodera* spp., *Longidorus* spp., *Meloidogyne* spp., *Pratylenchus* spp., *Radopholus similis, Trichodorus* spp., *Tylenchulus semipenetrans, Xiphinema* spp.

From the subphylum of the Protozoa, for example *Eimeria*.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organism) and RLO (Rickettsia-like organism). If appropriate, they can also be employed as intermediates or precursors for the synthesis of other active compounds.

All plants and plant parts can be treated in accordance with the invention. Plants are to be understood as meaning in the present context all plants and Plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights.

Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on their surroundings, habitat or storage space by the customary treatment methods, for example by immersion, spraying, evaporation, fogging, scattering, painting on, injection and, in the case of propagation material, in particular in the case of seeds, also by applying one or more coats.

The active compounds can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkypyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable solid carriers are:
for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphoriates, alkyl sulphates, arylsulphonates and also protein hydrolysates; suitable dispersants are nonionic and/or ionic substances, for example from the classes of the alcohol-POE and/or -POP ethers, acid and/or POP-POE esters, alkylaryl and/or POP-POE ethers, fat- and/or POP-POE adducts, POE- and/or POP-polyol derivatives, POE- and/or POP-sorbitan or sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose and natural and synthetic polymers in the form of powders, granules or lattices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active compound, preferably between 0.5 and 90%.

The active compound according to the invention can be used in its commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners fertilizers or semiochemicals.

A mixture with other known active compounds, such as herbicides, fertilizers, growth regulators, safeners, semiochemicals, or else with agents for improving the plant properties, is also possible.

When used as insecticides, the active compounds according to the invention can furthermore be present in their commercially available formulations and in the use forms, prepared from these formulations, as a mixture with synergists. Synergists are compounds which increase the action of the active compounds, without it being necessary for the synergist added to be active itself.

When used as insecticides, the active compounds according to the invention can furthermore be present in their commercially available formulations and in the use forms, prepared from these formulations, as a mixture with inhibitors which reduce degradation of the active compound after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

Application is carried out in a customary manner appropriate for the use forms.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* ssp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattela germanica, Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the compounds according to the invention also have a strong insecticidal action against insects which destroy industrial materials.

The following insects may be mentioned as examples and as preferred—but without any limitation:

Beetles, such as *Hylotrupes bajulus, Chlorophorus pilosis, Anobium punctatum, Xestobium rufavillosom, Ptilinus oecticornis, Dendrohium pertinex, Ernobius moliis, Priohium carpini, Lyetus brunneus, Lyctus athicanus, Lyctus plaiticollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychos brunneus, Sinoxylort* spec., *Dinocierus minutus;*

Hymenopterons, such as *Sirex juvencus, Urocerus gigas, Urocerus gigas taignus, Urocerus augur;*

Termites, such as *Kalotermes flavicollis, Cryptotennes brevis, Heterotermes indicola, Reticulitermes flavipes, Reticulitermes santonensis, Reticulitermes lucifugus, Mastotermes darwiniensis, Zootermopsis nevadensis, Coptotermes formosarius;*

Bristletails, such as *Lepisma saccharine.*

Industrial materials in the present connection are to be understood as meaning non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

With respect to possible additional additives, reference may be made to the insecticides and fungicides mentioned above.

The compounds according to the invention can likewise be employed for protecting objects which come into contact with saltwater or brackish water, such as hulls, screens, nets, buildings, moorings and signalling systems, against fouling.

Furthermore, the compounds according to the invention, alone or in combination with other active compounds, may be employed as antifouling agents.

In domestic, hygiene and stored-product protection, the active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus, Bryohia* ssp., *Derrnanyasus gallinee, Olyeiphagus domesticus, Ornithodorus moubat, Rhipicephalus sanguinous, Trombicula alfreddugesi, Neutrombicula autumnalis, Dermatophagoides pteroutssimus, Dermatophagoides forinae.*

From the order of the Araneae, for example, Aviculariidae, Araneidae,

From the order of the Opiliones, for example, Pseudoscorpiones chelifer, Pseudoscorpiones cheiridiurn, Opiliones phalangiurn.

From the order of the isopoda, for example, Oniscus aseilus, Porcellio amber.

From the order of the Diplopoda, for example, *Bianiulus guttulatus, Polydesmus* spp.

From the order of the Chilopoda, for example, *Geoplailus* spp.

From the order of the Zygentoma, for example, *Ctenolepisma* spp., *Lepisrna saceharina, Lepismodes inquilinus.*

From the order of the Blattaria, for example, *Blatta orientalies, Blattella gecmaniea, Blattella asahinai,* Leucophaea tnaderae, *Panchlora* spp., *Parcoblatta* spp., *Periplaneta australasiae, Periplaneta americana, Periplaneta brunnea, Periplaneta fuliginasa, Supella longipaipa.*

From the order of the Saltatoria, for example, *Acheta domesticus.*

From the order of the Dertnaptera, for example, *Forficula auricularia,*

From the order of the Isoptera, for example, *Kalotermes* spp., *Retieulitermes* spp.

From the order of the Psocoptera, for example, *Lepinatus* spp., *Liposcelis* spp.

From the order of the Coleoptera, for example *Anthrenus* spp., *Attagenus* spp., *Dermestes* spp., *Lathetietts oryzae, Necrobia* spp., *Ptinus* spp., *Rhizopertha, dominica, Sitophilus gran arias, Sitophilus oryzae, Sitophilus zeamais, Stegobium paniceum.*

From the order of the Diptera, for example, *Aedes aegypti, Aedes albopictus, Aedes taeniorhynehus, Anopheles* spp., *Calliphora etythrocephala, Chrysozona pluvialis, Culex quinquefasciatus, Culex pipiens, Culex tarsalis, Drosophila* spp., *Fannia canieularia, Musca domestica, Phlehotomus* spp., *Sarcophaga carnaria, Simulium* spp., *Stomoxys calcitrans, Tipula paludosa.*

From the order of the Lepidoptera, for example, *Achroia grisella, Galleria melonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginostis, Lasius niger, Lasius urobratus, Moriornotium pharaonis, Paravespula* spp., *Tetramorium caespitum.*

From the Order of the Anoplura, for example, *Pediculus humanus capitis, Pediculus humanus corporis, Pemphigus* spp., *Phylloera vastatrix, Phthirus pubis.*

From the order of the Heteroptera, for example, *Cimex hemiptenis, Cimex lectularius, Rhodirras prolixus, Triatoma infestans.*

In the field of household insecticides, they are used alone or in combination with other suitable active compounds, such as phosphoric esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The compounds of the formula (I) according to the invention (active compounds) have excellent herbicidal activity against a broad spectrum of economically important monocotylidonous and dicotylidonous annual harmful plants. The active compounds also act efficiently on perennial harmful plants which produce shoots from rhizomes, root stocks or other perennial organs and which are difficult to control.

The amount of active compound used may vary within a relatively wide range. It depends essentially on the nature of the desired effect. In general, the application rates are between 1 g and 10 kg of active compound per hectare of soil area, preferably between 5 g and 5 kg per ha.

The advantageous effect of the compatibility with crop plants of the active compound combinations according to the invention is particularly pronounced at certain concentration ratios. However, the weight ratios of the active compounds in the active compound combinations can be varied within relatively wide ranges. In general, from 0.001 to 1000 parts by weight, preferably from 0.01 to 100 parts by weight, particularly preferably from 0.05 to 20 parts by weight, of one of the crop plant compatibility-improving compounds (antidotes/safeners) mentioned above under (b') are present per part by weight of active compound of the formula (I).

The active compound combinations according to the invention are generally applied in the form of finished formulations. However, the active compounds present in the active compound combinations can, as individual formulations, also be mixed during use, i.e. be applied in the form of tank mixtures.

For certain applications, in particular in the post-emergence method, it may furthermore be advantageous to include in the formulations, as further additives, mineral or vegetable oils which are tolerated by plants (for example the commercial preparation "Rako Binol"), or ammonium salts, such as, for example, ammonium sulphate or ammonium thiocyanate.

The novel active compound combinations can be used as such, in the form of their formulations or the use forms prepared therefrom by further dilution, such as ready-to-use solutions, suspensions, emulsions, powders, pastes and granules. The application is in the customary manner, for example by watering, spraying, atomizing, dusting or broadcasting.

The application rates of the active compound combinations according to the invention can be varied within a certain range; they depend, inter alia, on the weather and on soil factors. In general, the application rates are from 0.001 to 5 kg per ha, preferably from 0.005 to 2 kg per ha, particularly preferably from 0.01 to 0.5 kg per ha.

Depending on their properties, the safeners to be used according to the invention can be used for pretreating the seed of the crop plant (seed dressing) or can be introduced into the seed ferrules prior to the seed or be used separately prior to the herbicide or together with the herbicide, before or after emergence of the plants.

Examples of plants which may be mentioned are important crop plants, such as cereals (wheat, barley, rice), maize, soya beans, potatoes, cotton, oilseed rape, beet, sugar cane and also fruit plants (with the fruits apples, pears, citrus fruits and grapevines), greater emphasis being given to cereals, maize, soya beans, potatoes, cotton and oilseed rape.

All plants and plant parts can be treated with the active compounds according to the invention. Here, plants are to be understood as meaning all plants and plant populations such as wanted and unwanted wild plants or crop plants (including naturally occurring crop plants). Crop plants can be plants which can be obtained by conventional plant breeding and optimization methods or by biotechnological and recombinant methods or by combinations of these methods, including the transgenic plants and inclusive of the plant cultivars protectable or not protectable by: plant breeders rights. Plant parts are to be understood as meaning all parts and organs of plants above and below the ground, such as shoot, leaf, flower and root, examples which may be mentioned being leaves, needles, stalks, stems, flowers, fruit bodies, fruits and seed and also roots, tubers and rhizomes. The plant parts also include harvested material, and also vegetative and generative propagation material, for example cuttings, tubers, rhizomes, offshoots and seeds.

Treatment according to the invention of the plants and plant parts with the active compounds is carried out directly or by allowing the compounds to act on their surroundings, habitat or storage space by the customary treatment methods, for example by immersion, spraying, evaporation, fogging, broadcasting, painting on or injection and, in the case of propagation material, in particular in the case of seed, also by applying one or more coats.

The present invention therefore also relates to a method of controlling unwanted plants or for regulating the growth of plants, preferably in crops of plants, where one or more compound(s) according to the invention is/are applied to the plants (for example harmful plants such as monocotyledonous or dicotyledonous weeds or unwanted crop plants), to the seed (for example grains, seeds or vegetative propagules such as tubers or shoot parts with buds) or to the area on which the plants grow (for example the area under cultivation), In this context, the compounds according to the invention can be applied far example pre-planting (if appropriate also by incorporation into the soil), pre-emergence or post-emergence. Examples of individual representatives of the monocotyledonous and dicotyledonous weed flora which can be controlled by the compounds according to the invention shall be mentioned, without the mention being intended as a limitation to certain species.

Monocotyledonous harmful plants of the genera: *Aegilops, Agropyron, Agrostis, Alopecurus, Apera, Avetra, Brachiaria, Bromus, Cenchrus, Commelina, Cynodon, Cyperus, Dactylocteniutn, Digitaria, Echinochloa, Eleocharis, Elettsine, Eragrostis, Eriochloa, Fesnica, Firnbristylis, Heteranthera, Imperata, Ischaemum, Leptochloa, Monochoria, Panicum, Paspalum, Phalaris, Phieum, Poa, Rottboellia, Sagittaria, Scirpus, Setaria, Sorghum.*

Dicotyledonous weeds of the genera: *Abutilori, Amaranthus, Ambrosia, Anode, Anthernis, Aphanes, Artemisia, Atriplex, Bellis, Bidens, Capsella, Carduus, Cassia, Centaurea, Chenopodium, Cirsium, Convolvulus, Datura, Desrnodium, Emex, Erysiinum, Euphorhia, Galeopsis, Galinsoga, Galium, Hibiscus, Ipomoea, Kochia, Lamium, Lepidium, Lindernia, Matricaria, Mentha, Mercurialis, Mullugo, Myosotis,*

*Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or mixtures specifically mentioned in the present text.

If the compounds according to the invention are applied to the soil surface before germination, either the emergence of the weed seedlings is prevented completely or the weeds grow until they have reached the cotyledon stage, but then stop their growth and, finally, die completely after three to four weeks have elapsed.

When the active compounds are applied post-emergence to the green plant parts, growth stops after the treatment, and the harmful plants remain in the growth stage of the time of application or die fully after a certain period of time, so that competition by weeds, which is harmful to the crop plants, is thus eliminated at an early point in time and in a sustained manner.

Although the compounds according to the invention display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Lintnn, Lycopersicon, Miscanthus, Nicotiana, Phaseolus, Pisum, Solanum, Vicia,* or monocotyledonous crops of the genera *Allium, Ananas, Asparagus, Averia, Hordeum, Oryza, Panicum, Saccharum, Sorghum, Triticale, Triticum, Zea,* are damaged only to an insignificant extent, or not at all, depending on the structure of the respective compound according to the invention and its application rate. This is why the present compounds are highly suitable for, the selective control of unwanted vegetation in plant crops such as agriculturally useful plants or ornamentals.

Moreover, the compounds according to the invention (depending on their respective structure and the application rate applied) have outstanding growth-regulatory properties in crop plants. They engage in the plant metabolism in a regulatory fashion and can therefore be employed for the influencing, in a targeted manner, of plant constituents and for facilitating harvesting, such as, for example, by triggering desiccation and stunted growth. Moreover, they are also suitable for generally controlling and inhibiting unwanted vegetative growth without destroying the plants in the process. Inhibiting the vegetative growth plays an important role in many monocotyledonous and dicotyledonous crops since for example lodging can be reduced, or prevented completely, hereby.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

Owing to their herbicidal and plant-growth-regulatory properties, the active compounds can also be employed for controlling harmful plants in crops of known genetically modified plants or genetically modified plants which are still to be developed. As a rule, the transgenic plants are distinguished by especially advantageous properties, for example by resistances to certain pesticides, mainly certain herbicides, resistances to plant diseases or causative organisms of plant diseases, such as certain insects or microorganisms such as fungi, bacteria or viruses. Other special properties relate for example to the harvested material with regard to quantity, quality, storability, composition and specific constituents. Thus, transgenic plants with an increased starch content or a modified starch quality or those with a different fatty acid composition of the harvested material are known. Further particular properties may be tolerance or resistance to abiotic stresses, for example heat, cold, drought, salt and ultraviolet radiation.

It is preferred to use the compounds of the formula (I) according to the invention in economically important transgenic crops of useful plants and ornamentals, for example of cereals such as wheat, barley, rye, oats, sorghum and millet, rice, cassava and maize or else crops of sugar beet, cotton, soya bean, oilseed rape, potato, tomato, peas and other vegetables.

It is preferred to employ the compounds of the formula (I) as herbicides in crops of useful plants which are resistant, or have been made resistant by recombinant means, to the phytotoxic effects of the herbicides.

Conventional ways of generating novel plants which, in comparison with existing plants, have modified properties are, for example, traditional breeding methods and the generation of mutants. Alternatively, novel plants with modified properties can be generated with the aid of recombinant methods (see, for example, EP-A-0221044, EP-A-0131624). For example, the following have been described in several cases:

recombinant modifications of crop plants for the purposes of modifying the starch synthesized in the plants (for example WO 92/11376 A1, WO 92/14827 A1, WO 91/19806 A1), transgenic crop plants which are resistant to certain herbicides of the glufosinate type (cf., for example, EP-A-0242236, EP-A-242246) or of the glyphosate type (WO 92/00377) or of the sulphonylurea type (EP-A-0257993, U.S. Pat. No. 5,013,659), or against combinations or mixtures of these herbicides by "gene stacking," such as transgenic crop plants, for example maize or soybeans having the trade name or designation Optimum™ GAT™ (GLYphosphate ALS Tolerant). Furthermore, transgenic plants resistant to synthetic auxins (for example 2, 4 D) HRAC mode of action Class O and aryloxyphenoxy proprionate (fops, HRAC, Class A) have been described (DHT, Dow Agroscience Herbicide Tolerance Trait), transgenic crop plants, for example cotton, which is capable of producing *Bacillus thuringiensis* toxins (Bt toxins), which make the plants resistant to certain pests (EP-A-0142924, EP-A-0193259), transgenic crop plants with a modified fatty acid composition (WO 91/13972 A1), genetically modified plants having novel resistances to insects, for example based on the expression of toxins from Photorhabdus, Xenorhabdus symbionts from entomopathogenic nematodes and toxins from spiders, scorpions, ants, parasitic wasps, genetically modified plants with reduced photorespiration which feature higher yields and higher stress tolerance (EPA 0305398), transgenic crop plants which produce pharmaceutically or diagnostically important proteins ("molecular pharming"), transgenic crop plants which are distinguished by higher yields or better quality, transgenic crop plants which are distinguished by increased tolerance to abiotic and biotic stress factors.

A large number of molecular-biological techniques by means of which novel transgenic plants with modified properties can be generated are known in principle; see, for example, I. Potrykus and G. Spangeriberg (eds.) Gene Transfer to Plants, Springer Lab Manual (1995), Springer Verlag Berlin, Heidelberg, or Christou, "Trends in Plant Science" 1 (1996) 423-431.

To carry out such recombinant manipulations, it is possible to introduce nucleic acid molecules into plasmids, which permit a mutagenesis or sequence modification by recombination of DNA sequences. For example, base substitutions can be carried out, part-sequences can be removed, or natural or synthetic sequences may be added with the aid of standard methods. To link the DNA fragments with one another, it is possible to add adapters or linkers to the fragments; see, for example, Sambrook et al., 1989, Molecular Cloning, A Laboratory Manual, 2nd ed., Cold Spring Harbor Laboratory Press, Cold Spring Harbor, Winnacker "Gene und Klone" VCH Weinheim 2nd ed., 1996

The generation of plant cells with a reduced activity for a gene product can be achieved for example by the expression of at least one corresponding antisense RNA, a sense RNA for achieving a cosuppression effect or by the expression of at least one correspondingly constructed ribozyme, which specifically cleaves transcripts of the abovementioned gene product.

To this end, it is possible firstly to use DNA molecules which comprise all of the coding sequence of a gene product, including any flanking sequences which may be present, or else DNA molecules which only comprise parts of the coding sequence, it being necessary for these parts to be long enough to bring about an antisense effect in the cells. It is also possible to use DNA sequences which have a high degree of homology with the coding sequences of a gene product, but which are not entirely identical.

When expressing nucleic acid molecules in plants, the protein synthesized may be localized in any compartment of the plant cell. In order to achieve localization in a particular compartment, however, it is possible for example to link the coding region to DNA sequences which ensure the localization in a specific compartment. Such sequences are known to the skilled worker (see, for example, Braun et al., EMBO J. 11 (1992), 3219-3227; Wolter et al., Proc. Natl. Acad. Sri, USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give intact plants. In principle, the transgenic plants may be plants of any plant species, that is to say both monocotyledonous and dicotyledonous plants.

Thus, transgenic plants can be obtained which feature modified properties as the result of overexpression, suppression or inhibition of homologous natural) genes or gene sequences or expression of heterologous (=foreign) genes or gene sequences.

It is preferred to employ the compounds (I) according to the invention in transgenic crops which are resistant to growth regulators such as, for example, 2,4 D, dicamba, or to herbicides which inhibit essential plant enzymes, the example acetyl CoA carboxylases, acetolactate synthases (ALS), EPSP synthases, glutamine syntheses (GS) or hydroxyphenylpyruvate, dioxygenases (HPPD), or to herbicides from the group of the FOPS, sulphonylureas, glyphosates, glufosinates or benzoylisoxazoles and analogous active compounds, or to any combinations of these active compounds.

It is particularly preferred to employ the compounds according to the invention in transgenic crop plants which are resistant to a combination of glyphosates and glufosinates, glyphosates and sulphonylureas or imidazolinones. It is very particularly preferred to employ the compounds according to the invention in transgenic crop plants, the example maize or soya, With the trade name or the designation Optimum™ GAT™ (Glyphosate ALS Tolerant). In addition, it is particularly preferred to employ the compounds according to the invention in transgenic plants which are resistant to synthetic auxins (e.g. 2,4 D) with "HRAC mode of action Class O" and aryloxy-phenoxy propionate (fops) with "HRAC mode of action Class A" (e.g. DHT, Dow Agroscience Herbicide Tolerance Trait).

When the active compounds according to the invention are used in transgenic crops, effects are frequently Observed—in addition to the effects on harmful plants which can be observed in other crops—which are specific for the application in the transgenic crop in question, for example a modified or specifically widened spectrum of weeds which can be controlled, modified application rates which may be employed for application, preferably good combinability with the herbicides to which the transgenic crop is resistant, and an effect on growth and yield of the transgenic crop plants.

The invention therefore also relates to the use of the compounds of the formula (I) according to the invention as herbicides for controlling harmful plants in transgenic crop plants.

The compounds according to the invention can be used in the form of wettable powders, emulsifiable concentrates, sprayable solutions, dusting products or granules in the customary formulations. The invention therefore also provides herbicidal and plant growth-regulating compositions which comprise the compounds according to the invention.

The compounds according to the invention can be formulated in various ways according to which biological and/or physicochemical parameters are required. Possible formulations include, for example: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), LTV formulations, microcapsules and waxes.

These individual formulation types are known in principle and are described, for example, in: Winnaoker-Küchler, "Chemische Technologie" [Chemical technology], Volume 7, C. Hanser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd, London.

The necessary formulation assistants, such as inert materials, surfactants, solvents and further additives, are likewise known and are described, for example, in: Watkins, "Handbook of insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem, Publ. Co. Inc., N.Y. 1964; Schönfeldt, "Grenzflächenaktive Äthylenoxidaddukte" [Interface-active ethylene oxide adducts], Wiss. Verlagsgesell., Stuttgart 1976; Wirmacker-Küchler, "Chemische Technologic", Volume 7, C. Hanser Verlag Munich; 4th Ed. 1986.

Based on these formulations, it is also possible to prepare combinations with other pesticidally active compounds, such as, for example, insecticides, acaracides, herbicides, fungicides, and also with safeners, fertilizers and/or growth regulators, for example in the form of a finished formulation or as a tank mix.

Wettable powders are preparations which can be dispersed uniformly in water and, as well as the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulphates, alkanesulphonates, alkylhenzenesulphonates, sodium lignosulphonate, sodium 2,2'-dinaphthylmethane-6,6'-disulphonate, sodium dibutylnaphthalenesulphonate or else sodium oleylmethyltauride. To prepare the wettable powders, the active herbicidal compounds are ground finely, for example in customary apparatus such as hammer mills, blower mills and air jet mills and simultaneously or subsequently mixed with the formulation assistants.

Emulsifiable concentrates are prepared by dissolving the active compound in an organic solvent, for example butanol, cyclohexanone, dimethylformamide, xylene or else relatively high-boiling aromatics or hydrocarbons or mixtures of the organic solvents with addition of one or more surfactants of the ionic and/or nonionic type (emulsifiers). The emulsifiers used may, for example, be: calcium alkylarylsulphonates such as calcium dodecylbenzensulphonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active compound with finely divided solid substances, for example talc, natural clays such as kaolin, bentonite and pyrophyllite, or diatomaceous earth.

Suspension concentrates may be water- or oil-based. They may be prepared, for example, by wet grinding by means of commercial bead mills and optional addition of surfactants as have, for example, already been listed above for the other formulation types.

Emulsions, for example oil-in-water emulsions (EW), can be prepared, for example, by means of stirrers, colloid mills and/or static mixers using aqueous organic solvents and optionally surfactants, as have, for example, already been listed above for the other formulation types.

Granules can be produced either by spraying the active compound onto adsorptive granulated inert material or by applying active compound concentrates by means of adhesives, for example polyvinyl alcohol, sodium poly-acrylate or else mineral oils, onto the surface of carriers such as sand, kaolinites or of granulated inert material. It is also possible to granulate suitable active compounds in the manner customary for the production of fertilizer granules—if desired in a mixture with fertilizers.

Water-dispersible granules are prepared generally by the customary processes such as spray-drying, fluidized bed granulation, pan granulation, mixing with high-speed mixers and extrusion without solid inert material.

For the preparation of pan, fluidized bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 ff; "Perry's Chemical Engineer's Handbook", 5th Ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Prayer, S. A. Evans, "Weed Control Handbook", 5th Ed., Blackwell Scientific Publications, Oxford, 1968, pages 101-103.

The agrochemical formulations contain generally from 0.1 to 99% by weight, in particular from 0.1 to 95% by weight, of compounds according to the invention.

In wettable powders, the active compound concentration is, for example, from about 10 to 90% by weight; the remainder to 100% by weight consists of customary formulation constituents. In the case of emulsifiable concentrates, the active compound concentration may be from about 1 to 90% by weight, preferably from 5 to 80% by weight. Dust-type formulations contain from 1 to 30% by weight of active compound, preferably usually from 5 to 20% by weight of active compound; sprayable solutions contain from about 0.05 to 80% by weight, preferably from 2 to 50% by weight of active compound, in water-dispersible granules, the active compound content depends partly on whether the active compound is present in solid or liquid form and which granulation assistants, fillers, etc. are used. In the granules dispersible in water, the content of active compound is, for example, between 1 and 95% by weight, preferably between 10 and 80% by weight.

In addition, the active compound formulations mentioned optionally comprise the respective customary adhesives, wetting agents, dispersants, emulsifiers, penetrants, preservatives, antifreeze agents and solvents, fillers, carriers and dyes, defoamers, evaporation inhibitors and agents which influence the pH and the viscosity.

The method of treatment according to the invention is preferably applied to genetically modified organisms, such as, for example, plants or parts of plants.

Genetically modified plants (or transgenic plants) are plants in which a heterologous gene has been stably integrated into the genome.

The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example antisense technology, cosuppression technology or RNA interference RNAi technology). A heterologous gene that is located in the genome is also called a transgene. A transgene that is defined by its particular location in the plant genome is called a transformation or transgenic, event.

Depending on the plant species or plant varieties, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf colour, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to formula (I) may also have a strengthening effect in plants. Accordingly, they are suitable for mobilizing the defence system of the plant against attack by unwanted phytopathogenic fungi and/or microorganisms and/or viruses. This may, if appropriate, be one of the reasons for the enhanced activity of the combinations according to the invention, for example against fungi. Plant-strengthening (resistance-inducing) substances are understood as meaning, in the present context, also those substances or combinations of substances which are capable of stimulating the defence system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are understood to mean phytopathogenic fungi bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants which are also preferably treated in accordance with the invention are resistant to one or more biotic stress factors, i.e. said plants have an improved defence against animal and microbial pests, such as nematodes, insects, mites, phytopathogenic fungi, bacteria, viruses and/or viroids.

In addition to the aforementioned plants and plant varieties, it is also possible in accordance with the invention to treat those which are resistant to one or more abiotic stress factors.

Abiotic stress conditions may include, for example, drought, cold exposure, heat exposure, osmotic stress, waterlogging, increased soil salinity, increased exposure to minerals, ozone conditions, strong light conditions, limited availability of nitrogen nutrients, limited availability of phosphorus nutrients or shade avoidance.

Plants and plant varieties which may also be treated in accordance with the invention are those plants characterized by enhanced yield characteristics. Enhanced yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or eat, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated in accordance with the invention are hybrid plants that already express the characteristics of heterosis, or hybrid vigour, which results in generally higher yield, vigour, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in the hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm, Examples of cytoplasmic male sterility (CMS) were for instance described for *Brassica* species. However, genetic determinants for male sterility can also be located in the nuclear genome. Male sterile plants can also be obtained by plant biotechnology methods such as genetic engineering. A particularly useful means of obtaining male sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated in accordance with the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp., the genes encoding a petunia EPSPS, a tomato EPSPS, or an *Eleusine* EPSPS. It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyltransferase enzyme. Glyphosate-tolerant plants can also be obtained by selecting plants containing naturally occurring mutations of the above-mentioned genes.

Other herbicide-resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species). Plants expressing an exogenous phosphinothricin acetyltransferase are described.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD inhibitors can be transformed with a gene encoding a naturally occurring resistant HPPD enzyme, or a gene encoding a mutated HPPD enzyme.

Tolerance to HPPD inhibitors can also be obtained by transforming plants with genes encoding certain enzymes enabling the formation of homogentisate despite the inhibition of the native HPPD enzyme by the HPPD inhibitor. Tolerance of plants to HPPD inhibitors can also be improved by transforming plants with a gene encoding an enzyme of prephenate dehydrogenase in addition to a gene encoding an HPPD-tolerant enzyme.

Further herbicide-resistant plants are plants that are made tolerant to acetolactate synthase (ALS) inhibitors. Known ALS inhibitors include, for example, sulphonylurea, imidazolinone, triazolopy pyrimidinyloxy(thio)benzoates, and/or sulphonylaminocarbonyltriazolinone herbicides. Different mutations in the ALS enzyme (also known as acetohydroxyacid synthase, AHAS) are known to confer tolerance to different herbicides and groups of herbicides. The production of sulphonylurea-tolerant plants and imidazolinone-tolerant plants has been described in the international publication WO 1996/033270. Further sulphonylurea- and imidazolinone-tolerant plants have also been described, for example in WO 2007/024782.

Further herbicide-resistant plants are plants which have been rendered tolerant to ACCase inhibitors.

Further plants tolerant to imidazolinone and/or sulphonylurea can be obtained by induced mutagenesis, selection in cell cultures in the presence of the herbicide or mutation breeding.

Plants or plant varieties (obtained by plant biotechnology methods such as genetic engineering) which may also be treated in accordance with the invention are insect-resistant transgenic plants, i.e. plants made resistant to attack by certain target insects. Such plants can be obtained by genetic transformation, or by selection of plants containing a mutation imparting such insect resistance.

The term "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed online at: http://www.lifesci.sussex.ac.uk/Home/Neil_Crickmore/Bt/, or insecticidal portions thereof, e.g. proteins of the Cry protein classes Cry1Ab, Cry1Ac, Cry1F, Cry2Ab, Cry3Ae, or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins; or 3) a hybrid insecticidal protein comprising parts of two different insecticidal crystal proteins from *Bacillus thuringiensis*, such as a hybrid of the proteins of 1) above or a hybrid of the proteins of 2) above, e.g. the Cry1A.105 protein produced by corn event MON98034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes induced into the encoding DNA during cloning or transformation, such as the Cry3Bb1 protein in corn events MON863 or MON88017, or the Cry3A protein in corn event MIR 604;

5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/Home/Neil_Crickmore/Bt/vip.html, e.g. proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins; or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes induced into the encoding DNA during cloning or transformation (while still encoding an insecticidal protein), such as the VIP3Aa protein in cotton event COT 102.

Of course, insect-resistant transgenic plants, as used herein, also include any plant comprising a combination of genes encoding the proteins of any one of the above classes 1 to 8, in one embodiment, an insect-resistant plant contains more than one transgene encoding a protein of any one of the above classes 1 to 8, to expand the range of target insect species affected or to delay insect resistance development to the plants, by using different proteins insecticidal to the same target insect species but having a different mode of action, such as binding to different receptor binding sites in the insect.

Plants or plant varieties (Obtained by plant biotechnology methods such as genetic engineering) which may also be treated in accordance with the invention are tolerant to abiotic stresses. Such plants can be Obtained by genetic transformation, or by selection of plants containing a mutation imparting such stress resistance. Particularly useful stress tolerance plants include:
- a. plants which contain a transgene capable of reducing the expression and/or the activity of the poly(ADP-ribose) polymerase (PARP) gene in the plant cells or plants.
- b. plants which contain a stress tolerance-enhancing transgene capable of reducing the expression and/or the activity of the PARG-encoding genes of the plants or plant cells;
- c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant cultivars (obtained by plant biotechnology methods such as genetic engineering) which may likewise be treated in accordance with the invention have an altered quantity, quality and/or storage stability of the harvested product and/or altered properties of specific ingredients of the harvested product, for example:
1) transgenic plants which synthesize a modified starch whose physicochemical characteristics, in particular the amylose content or the amylose/amylopectin ratio, the degree of branching, the average chain length, the side chain distribution, the viscosity behaviour, the gelling strength, the starch grain size and/or the starch grain morphology, is altered compared to the synthesized starch in wild type plant cells or plants, such that this modified starch is better suited for certain applications.
2) transgenic plants which synthesize non-starch carbohydrate polymers or which synthesize non-starch carbohydrate polymers with altered properties in comparison to wild type plants without genetic modification. Examples are plants which produce polyfructose, especially of the inulin and levan type, plants which produce alpha-1,4-glucans, plants which produce alpha-1,6 branched alpha-1,4-glucans, and plants producing alternan.
3) transgenic plants which produce hyaluronan.

Plants or plant cultivars (which can be obtained by plant biotechnology methods such as genetic engineering) which may likewise be treated in accordance with the invention are plants, such as cotton plants, with altered fibre characteristics. Such plants can be obtained by genetic transformation, or by selection of plants containing a mutation imparting such altered fibre characteristics and include:
- a) plants, such as cotton plants, which contain an altered form of cellulose synthase genes;
- b) plants, such as cotton plants, which contain an altered form of rsw2 or rsw3 homologous nucleic acids;
- c) plants, such as cotton plants, with an increased expression of sucrose phosphate synthase;
- d) plants, such as cotton plants, with an increased expression of sucrose synthase;
- e) plants, such as cotton plants, Wherein the timing of the plasmodesmatal gating at the basis of the fibre cell is altered, for example through downregulation of fibre-selective β-1,3-glucanase;
- f) plants, such as cotton plants, which have fibres with altered reactivity, for example through the expression of the N-acetylglucosaminetransferase gene including nodC and chitin synthase genes.

Plants or plant cultivars (that can be obtained by plant biotechnology methods such as genetic engineering) which may also be treated in accordance with the invention are plants, such as oilseed rape or related *Brassica* plants, with altered oil profile characteristics. Such plants can be obtained by genetic transformation or by selection of plants containing a mutation imparting such altered oil characteristics and include:
- a) plants, such as oilseed rape plants, which produce oil having a high oleic acid content;
- b) plants, such as oilseed rape plants, which produce oil having it low linolenic acid content;
- c) plants, such as oilseed rape plants, which produce oil having a low level of saturated fatty acids.

Particularly useful transgenic plants which may be treated in accordance with the invention are plants which comprise one or more genes which encode one or more toxins, are the following which are sold under the trade names: YIELD GARD® (for example maize, cotton, soya beans), KnockOut® (for example maize), BiteGard® (for example maize), Bt-Xtra® (for example maize), StartLink® (for example maize), Bollgard® (cotton), Nueotn® (cotton), Nucotn 33B® (cotton), NatureGard® (for example maize), Protecta® and NewLeaf® (potato). Examples of herbicide-tolerant plants which may be mentioned are maize varieties, cotton varieties and soya bean varieties which are sold under the trade names: Roundup Ready® (tolerance to glyphosate, for example maize, cotton, soya beans), Liberty Link® (tolerance to phosphinothricin, for example oilseed rape), IMI® (tolerance to imidazolinone) and SCS® (tolerance to sulphonylurea, for example maize). Herbicide-resistant plants (plants bred in a conventional manner for herbicide tolerance) which may be mentioned include the varieties sold under the name Clearfield® (for example maize).

Particularly useful transgenic plants which may be treated in accordance with the invention are plants containing transformation events, or a combination of transformation events, that are listed for example in the databases for various national or regional regulatory agencies (see for example http://gmoinfo.jrc.it/gmp_browse.aspx and http://www.agbios.com/dbase.php).

The term "active compounds" or "compounds" always also includes the active ingredient combinations mentioned here too.

PREPARATION EXAMPLES

Example II-1

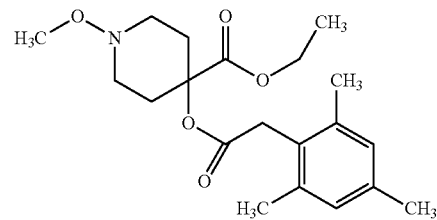

610 mg (3 mmol) of ethyl 1-methoxy-4-hydroxypiperidinecarboxylate and 590 mg (3 mmol) of mesitylacetyl chloride in 20 ml of tuloene are boiled at reflux for 12 h, the mixture is concentrated on a rotary evaporator and the residue is partitioned between 5% strength aqueous sodium hydroxide solution and dichloromethane. The organic phase is dried, concentrated and purified by chromatography on silica gel (mobile phase dichloromethane/methanol 100:10).

Yield:

440 mg (28% of theory)

log P (HCOOH)=4.28

M+1 (LC/MS)=364.1

$^1$H-NMR (400 MHz, d6-DMSO)=1.1 (t, 3H), 1.95 (m, 4H), 2.2 (s, 3H), 2.23 (s, 6H), 3.10 (m, 4H), 3.40 (s, 3H), 3.68 (s, 2H), 4.05 (q, 2H), 6.85 (s, 2H) ppm.

The following compounds of the formula (II) are obtained analogously to Example (II-1) and in accordance with the general statements about the preparation:

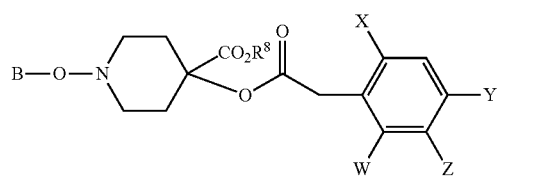

(II)

| Ex. No. | W | X | Y | Z | B | R$^8$ | LC/MS+ NMR |
|---|---|---|---|---|---|---|---|
| II-2 | H | CH$_3$ | CH$_3$ | CH$_3$ | CH$_3$ | C$_2$H$_5$ | 2) |
| II-3 | CH$_3$ | C$_2$H$_5$ | CH$_3$ | H | CH$_3$ | C$_2$H$_5$ | 3) |
| II-4 | H | CH$_3$ | H | 4-Cl-Ph | CH$_3$ | C$_2$H$_5$ | 4) |
| II-5 | CH$_3$ | CH$_3$ | H | 4-Cl-Ph | CH$_3$ | C$_2$H$_5$ | 5) |
| II-6 | CH$_3$ | C$_2$H$_5$ | 4-Cl-Ph | H | CH$_3$ | C$_2$H$_5$ | 6) |
| II-7 | CH$_3$ | CH$_3$ | CH$_3$ | H | C$_2$H$_5$ | C$_2$H$_5$ | M + 1: 378.2 |
| II-8 | CH$_3$ | CH$_3$ | H | 4-F-Ph | C$_2$H$_5$ | C$_2$H$_5$ | M + 1: 458.3 |
| II-9 | CH$_3$ | CH$_3$ | H | 4-F-Ph | CH$_3$ | C$_2$H$_5$ | M + 1: 444.2 |
| II-10 | C$_2$H$_5$ | C$_2$H$_5$ | CH$_3$ | H | CH$_3$ | C$_2$H$_5$ | M + 1: 392.3 |
| II-11 | C$_2$H$_5$ | C$_2$H$_5$ | CH$_3$ | H | C$_2$H$_5$ | C$_2$H$_5$ | M + 1: 406.2 |
| II-12 | CH$_3$ | CH$_3$ | H | 4-Cl-Ph | C$_2$H$_5$ | C$_2$H$_5$ | M + 1: 474.2 |
| II-13 | H | CH$_3$ | H | 4-Cl-Ph | C$_2$H$_5$ | C$_2$H$_5$ | M + 1: 460.2 |

Ph = phenyl

Examples II-7 to II-13 were used without further purification and characterization of the structure for preparing the compounds I-a-7 to I-a-13.

2) $^1$H-NMR (400 MHz, d6-DMSO): 1.11 (t, 3H, C$_2$H$_5$), 4.07 (q, 2H, C$_2$H$_5$), 6.93 (m, 2H, ArH) ppm

LC/MS M+1: 364.2

3) $^1$H-NMR (400 MHz, d6-DMSO): 1.12 (t, 3H, C$_2$H$_5$), 4.05 (q, 2H, C$_2$H$_5$), 6.84 (m, 2H, ArH) ppm

LC/MS M+1: 378.2

4) $^1$H-NMR (400 MHz, CDCl$_3$): 1.15 (t, 3H, C$_2$H$_5$), 2.32 (s, 3H, ArCH$_3$), 4.20 (q, 2H, C$_2$H$_5$) ppm

LC/MS M+1: 446.1

5) $^1$H-NMR (400 MHz, d6-DMSO): 1.10 (t, 3H, C$_2$H$_5$), 3.43 (s, 3H, N—OCH$_3$), 4.05 (q, 3H, C$_2$H$_5$) ppm

LC/MS M+1: 430.2

6) $^1$H-NMR (400 MHz, d6-DMSO): 1.12 (m, 3H, C$_2$H$_5$), 4.08 (m, 2H, C$_2$H$_5$) 7.2-7.8 (m, 6H, ArH) ppm

LC/MS M+1: 474.2

Example I-a-1

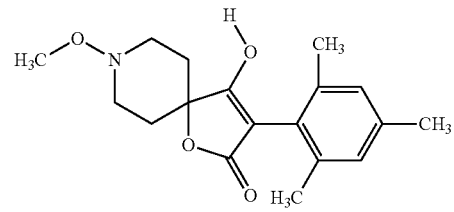

204 mg (1.81 mmol) of potassium tert-butoxide are initially charged in 5 ml of N,N-dimethylformamide, a solution of 440 mg (1.21 mmol) of the compound according to Example (II-1) in 5 ml of N,N-dimethylformamide is added dropwise and the mixture is stirred at room temperature for 12 h. For work-up, the solvent is removed using a rotary evaporator, the residue is partitioned between water and methyl tert-butyl ether and the aqueous phase is acidified with 1N hydrochloric acid and extracted with dichloromethane. The organic phase is dried and concentrated using a rotary evaporator. Further purification is by preparative HPLC (RP 18 phase, acetonitrile/water).

Yield: 176 mg (45% of theory)

log P (HCOOH)=2.15

M+1 (LC/MS)=318.1

$^1$H-NMR (400 MHz, d6-DMSO)=1.58 (m, 2H), 2.05 (s, 6H), 2.22 (s, 3H), 2.25 (m, 2H), 2.75 (m, 2H), 3.34 (m, 2H), 3.48 (s, 3H), 6.88 (s, 2H) ppm.

The following compounds of the formula (I-a) are obtained analogously to Example (I-a-1) and in accordance with the general statements about the preparation:

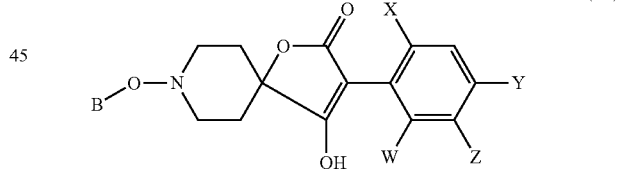

(I-a)

| Ex. No. | W | X | Y | Z | B | LC/MS+ NMR |
|---|---|---|---|---|---|---|
| I-a-2 | H | CH$_3$ | CH$_3$ | CH$_3$ | CH$_3$ | 2) |
| I-a-3 | CH$_3$ | C$_2$H$_5$ | CH$_3$ | H | CH$_3$ | 3) |
| I-a-4 | H | CH$_3$ | H | 4-Cl-Ph | CH$_3$ | 4) |
| I-a-5 | CH$_3$ | CH$_3$ | H | 4-Cl-Ph | CH$_3$ | 5) |
| I-a-6 | CH$_3$ | C$_2$H$_5$ | 4-Cl-Ph | H | CH$_3$ | 6) |
| I-a-7 | CH$_3$ | CH$_3$ | CH$_3$ | H | C$_2$H$_5$ | 7) |
| I-a-8 | CH$_3$ | CH$_3$ | H | 4-F-Ph | C$_2$H$_5$ | 8) |
| I-a-9 | CH$_3$ | CH$_3$ | H | 4-F-Ph | CH$_3$ | 9) |
| I-a-10 | C$_2$H$_5$ | C$_2$H$_5$ | CH$_3$ | H | CH$_3$ | 10) |
| I-a-11 | C$_2$H$_5$ | C$_2$H$_5$ | CH$_3$ | H | C2H$_5$ | 11) |
| I-a-12 | CH$_3$ | CH$_3$ | H | 4-Cl-Ph | C2H$_5$ | 12) |
| I-a-13 | H | CH$_3$ | H | 4-Cl-Ph | C2H$_5$ | 13) |

2) LC/MS M+1: 318.1
¹H-NMR (400 MHz, d6-DMSO): 3.46 (s, 3H, N—OCH₃), 6.86 (m, 1H, ArH), 6.98 (m, 1H, ArH) ppm 3) LC/MS M+1: 332.2
¹H-NMR (400 MHz, d6-DMSO): 3.47 (s, 3H, N—OCH₃), 6.88 (m, 2H, ArH) ppm 4) LC/MS M+1: 400.1
¹H-NMR (400 MHz, d6-DMSO): 2.19 (s, 3H, ArCH₃), 3.47 (s, 3H, N—OCH₃) ppm 5) LC/MS M+1: 414.1
¹H-NMR (400 MHz, d6-DMSO): 1.98 (s, 3H, ArCH₃), 2.14 (s, 3H, ArCH₃), 3.47 (s, 3H, N—O CH₃) ppm 6) LC/MS M+1: 428.2
¹H-NMR (400 MHz, d6-DMSO): 2.16 (s, 3H, ArCH₃), 3.48 (s, 3H, N—OCH₃), 7.47 (m, 2H, ArH), 7.50 (m, 2H, ArH), 7.69 (m, 2H, ArH) ppm 7) LC-MS: M+1=332.3
¹H-NMR (DMSO)=1.10 (t, 3H), 1.65-2.25 (m, 4H), 2.05 (s, 6H), 2.28 (s, 3H), 2.60 (m, 2H), 3.28 (m, 2H), 3.70 (q, 2H), 6.88 (s, 2H) ppm 8) LC-MS: M+1=412.1
¹H-NMR (DMSO)=1.12 (t, 3H), 1.70 (m, 2H), 1.97 (s, 3H), 2.13 (s, 3H), 2.20 (m, 2H), 2.62 (m, 2H), 3.27 (m, 2H), 3.69 (q, 2H), 7.10-7.35 (m, 6H) ppm 9) LC-MS: M+1=398.2
¹H-NMR (DMSO)=1.70 (m, 2H), 1.98 (s, 3H), 2.15 (s, 3H), 2.18 (m, 2H), 2.58 (m, 2H), 3.35 (m, 2H), 3.49 (s, 3H), 7.10-7.35 (m, 61-1) ppm 10) LC-MS: M+1=346.2
¹H-NMR (DMSO)=1.01 (t, 6H), 1.65 (m, 2H), 2.20 (m, 2H), 2.28 (s, 3H), 2.38 (m, 4H), 2.59 (m, 2H), 3.30 (m, 2H), 3.48 (s, 3H), 6.90 (s, 2H) ppm 11) LC-MS: M+1=360.2
¹H-NMR (DMSO)=1.02 (t, 6H), 1.12 (t, 3H), 1.63 (m, 2H), 2.20 (m, 2H), 2.28 (s, 3H), 2.34 (q, 4H), 2.63 (m, 2H), 3.28 (m, 2H), 3.69 (q, 2H), 6.90 (s, 2H ppm.

12) LC-MS: M+1=428.2
¹H-NMR (DMSO)=1.11 (t, 3H), 1.70 (m, 2H), 1.98 (s, 3H), 2.14 (s, 3H), 2.20 (m, 2H), 2.63 (m, 2H), 3.27 (m, 2H), 3.70 (q, 2H), 7.10-7.50 (m, 6H) ppm 13) LC-MS: M+1=414.2
¹H-NMR (CDCl₃)=1.15 (t, 3H), 1.20-3.70 (m, 8H), 2.15 (s, 3H), 3.72 (m, 2H), 7.20-7.50 (m, 7H) ppm Example I-b-1

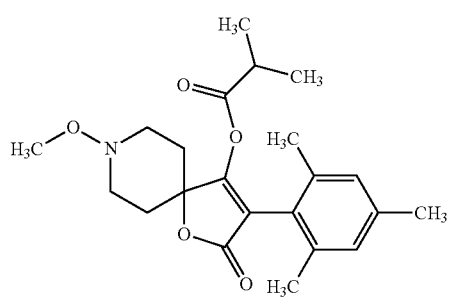

70 mg (0.22 mmol) of the compound according to Example I-a-1 and 27 mg (0.26 mmol) of triethylamine are initially charged in 5 ml of tetrahydrofuran, 28 mg (0.26 mmol) of isobutyryl chloride are added and the mixture is stirred overnight. For work-up, the solvent is removed and the residue is purified by preparative HPLC (RP18, acetonitrile/water).

Yield: 53 mg (62% of theory)
M+1 (LC/MS)=388.2
¹H-NMR (400 MHz, CDCl₃)=1.02 (d, 6H), 1.85 (m, 2H), 2.12 (s, 6H), 2.24 (s, 3H), 2.60 (m, 1H), 2.85 (m, 2H), 3.38 (m, 2H), 3.57 (s, 3H), 6.85 (s, 2H) ppm.

The compound of the formula (I-b-2) is obtained analogously to Example (I-b-1) and in accordance with the general statements about the preparation:

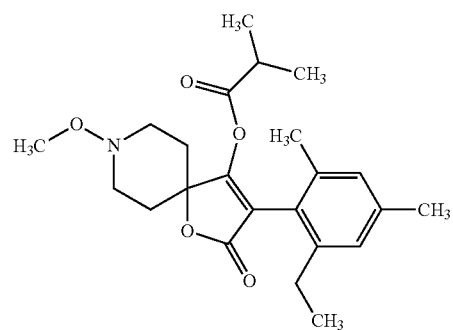

M+1 (LC/MS)=402.2
¹H-NMR (400 MHz, CDCl₃)=0.95-1.15 (m, 9H, 3 CH₃CH₂CH₃/CH(CH₃)₂), 2.88 (m, 1H, CH(CH₃)₂), 6.87 (s, 2H, ArH) ppm.

Example I-c-1

Example I-c-1 is obtained analogously to Example (I-b-1),

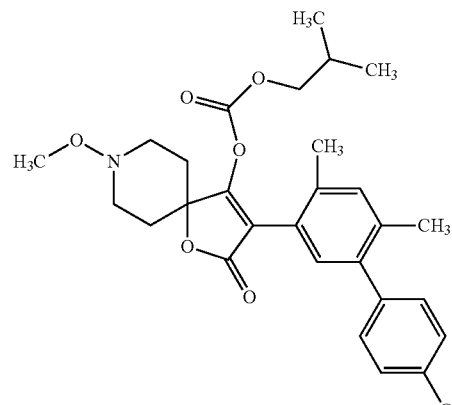

M+1 (LC/MS)=500.2
¹H-NMR (400 MHz, CDCl₃)=0.74 (d, 6H, CH(CH₃)₂), 3.57 (s, 3H, OCH₃), 3.76 (d, 2H, OCH₂—CH(CH₃)₂) ppm.

Preparation of Example XIV-1

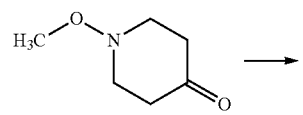

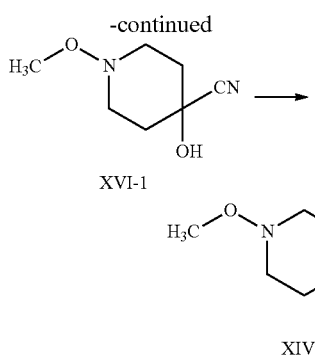

XVI-1

XIV-1

At 0° C., 5.4 g (0.11 mol) of sodium cyanide and 12.9 g (0.1 mol) of N-methoxypiperidin-4-one (known from Major & Düsch, Journal of Organic Chemistry, 1961, 26, 1867-74) are initially charged with stirring in 14 ml of water, and dilute sulphuric acid (20 ml of water and 9.8 g of $H_2SO_4$) is added dropwise, the temperature being kept below 5° C. The reaction is allowed to warm to room temperature overnight and carefully poured into a potassium carbonate solution (21 g of potassium carbonate in 150 ml of water). The aqueous alkaline solution is saturated with sodium chloride and extracted twice with ethyl acetate and twice with chloroform. The combined organic phases are dried over sodium sulphate and concentrated on a rotary evaporator.

The crude cyanohydrin of the formula (XVI-1) (15.6 g) is boiled at reflux in a mixture of 50 ml of conc. hydrochloric acid and 25 ml of water for 3 h, the solvent is removed on a rotary evaporator and the residue is triturated with 16.6 g (0.12 mol) of potassium carbonate in ethanol for 1 h. The suspension is acidified with conc. sulphuric acid and refluxed overnight. Most of the ethanol is distilled off, and ethyl acetate and ice-cold potassium carbonate solution are added to the residue, the pH being kept between 8 and 9. The org. phase is separated off and dried, the solvent is removed on a rotary evaporator and the residue is distilled under oil pump vacuum (boiling point 50-53° C.).

Yield:

4.86 g (24% of theory over all steps)

log P (HCOOH): 0.94

LC/MS (M+1): 204.2

$^1$H-NMR (400 MHz, $CDCl_3$): 1.29 (t, 3H), 1.72 (m, 2H), 2.14 (m, 2H), 2.36 (br, 1H), 2.75 (m, 2H), 3.22 (m, 2H), 3.55 (s, 3H), 4.24 (q, 2H) ppm.

Example (XIV-2) is obtained analogously to Example (XIV-1)

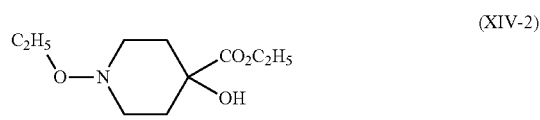 [SMILES: CCOC(=O)C1(O)CCN(OCC)CC1]

(XIV-2)

log P (M+1): 1.16

LC/MS cm-F-1)=218.2

$^1$H-NMR (400 MHz, $CDCl_3$)=1.18 (t, 3H), 1.30 (t, 3H), 1.70 (m, 2H), 2.15 (m, 2H), 2.79 (m, 2H) 3.18 (m, 2H), 3.75 (m, 2H), 4.22 (m, 2H) ppm.

The LC-MS determination in the acidic range is carried out at pH 2.7 using 0.1% aqueous formic acid and acetonitrile (contains 0.1% formic acid) as mobile phases; linear gradient from 10% acetonitrile to 95% acetonitrile.

The LC-MS determination in the neutral range is carried out at pH 7.8 using 0.001-molar aqueous ammonium bicarbonate solution and acetonitrile as mobile phases; linear gradient from 10% acetonitrile to 95% acetonitrile.

Calibration is carried out using unbranched alkan-2-ones (with 3 to 16 carbon atoms) with known log P values (determination of the log P values by the retention times using linear interpolation between two successive alkanones).

The lambda-max values were determined in the maxima of the chromatographic signals using the UV spectra from 200 nm to 400 nm.

USE EXAMPLES

Example 1

Phaedon Test

PHAECO Spray Treatment

| Solvents: | 78.0 | parts by weight of acetone |
| --- | --- | --- |
|  | 1.5 | parts by weight of dimethylformamide |
| Emulsifier: | 0.5 | part by weight of alkylaryl polyglycol ether |

To produce a suitable preparation of active compound, one part by weight of active compound is mixed with the stated amounts of solvents and emulsifier, and the concentrate is diluted with emulsifier-containing water to the desired concentration.

Discs of Chinese cabbage leaves (*Brassica pekinensis*) are sprayed with an active compound preparation of the desired concentration and, after drying, populated with larvae of the mustard beetle (*Phaedon cochleariae*).

After 7 days, the effect in percent is determined. 100% means that all beetle larvae have been killed; 0% means that none of the beetle larvae have been killed.

In this test, for example, the following compounds of the Preparation Examples show an activity of 100% at an application rate of 500 g/ha Ex. Nos.: I-a-4, I-a-6, I-a-13

Example 2

Myzus Test

MVZUPE Spray Treatment

| Solvents: | 78 | parts by weight of acetone |
| --- | --- | --- |
|  | 1.5 | parts by weight of dimethylformamide |
| Emulsifier: | 0.5 | part by weight of alkylaryl polyglycol ether |

To produce a suitable preparation of active compound, one part by weight of active compound is mixed with the stated amounts of solvents and emulsifier, and the concentrate is diluted with emulsifier-containing water to the desired concentration.

Discs of Chinese cabbage leaves (*Brassica pekinensis*) which are infested by all stages of the green peach aphid (*Myzus persicae*) are sprayed with an active compound preparation of the desired concentration.

After 6 days, the effect in percent is determined. 100% means that all aphids have been killed; 0% means that none of the aphids have been killed.

In this test, for example, the following compounds of the Preparation Examples show an activity of 100% at an application rate of 500 g/ha:

Ex. Nos.: I-a-3, I-a-4, I-a-7, I-a-9, I-a-10, I-a-11, I-a-12, I-a-13

In this test, for example, the following compounds of the Preparation Examples show an activity of 100% at an application rate of 100 g/ha:

Ex. No.: I-a-5

Example 3

*Spodoptera frugiperda* Test

SPODFR Spray Treatment

| Solvents: | 78.0 | parts by weight of acetone |
| | 1.5 | parts by weight of dimethylformamide |
| Emulsifier: | 0.5 | part by weight of alkylaryl polyglycol ether |

To produce a suitable preparation of active compound, one part by weight of active compound is mixed with the stated amounts of solvents and emulsifier, and the concentrate is diluted with emulsifier-containing water to the desired concentration.

Discs of maize leaves (*Zea mays*) are sprayed with an active compound preparation of the desired concentration and, after drying, populated with caterpillars of the armyworm (*Spodoptera frugiperda*).

After 6 days, the effect in percent is determined. 100% means that all aphids have been killed; 0% means that none of the aphids have been killed.

In this test, for example, the following compounds of the Preparation Examples show an activity of ≥80% at an application rate of 500 g/ha:

Ex. No.: I-a-5

In this test, for example, the following compounds of the Preparation Examples show an activity of ≥100% at an application rate of 100 g/ha:

Ex. No.: I-a-12

Example 4

*Tetranychus* Test, OP-Resistant

TETRUR Spray Treatment

| Solvents: | 78.0 | parts by weight of acetone |
| | 1.5 | parts by weight of dimethylformamide |
| Emulsifier: | 0.5 | part by weight of alkylaryl polyglycol ether |

To produce a suitable preparation of active compound, one part by weight of active compound is mixed with the stated amounts of solvents and emulsifier, and the concentrate is diluted with emulsifier-containing water to the desired concentration.

Discs of bean leaves (*Phaseolus vulgaris*) which are infested by all stages of the red spider mite (*Tetranychus urticae*) are sprayed with an active compound preparation of the desired concentration.

After 6 days, the effect in percent is determined. 100% means that all spider mites have been killed; 0% means that none of the spider mites have been killed.

In this test, for example, the following compounds of the Preparation Examples show good activity of ≥80% at an application rate of 100 g/ha:

Ex. Nos.: I-a-3, I-a-4, I-a-5, I-a-6, I-a-7, I-a-8, I-a-9, I-a-12, I-a-13

In this test, for example, the following compounds of the Preparation Examples show good activity of ≥90% at an application rate of 100 g/ha:

Ex. Nos.: I-a-9, I-a-13

Example 5

1. Herbicidal pre-emergence action

Seeds of monocotylidonous and dicotylidonous weed and crop plants are placed in sandy loam in wood fibre pots and covered with soil. The test compounds, formulated in the form of wettable powders (WP), are then, as an aqueous suspension with a water application rate of 600 l/ha (converted), with 0.2% of wetting agent added, applied to the surface of the covering soil in different amounts.

After the treatment, the pots are placed in a greenhouse and kept under good growth conditions for the test plants. The visual assessment of the emergence damage on the test plants is carried out after a trial period of three weeks by comparison with the untreated controls (herbicidal effect in percent: 100% effect=the plants have died, 0% effect=like control plants).

In addition to the compounds mentioned above, the following compounds, applied by the pre-emergence method at 320 g/ha a.i., show an activity of ≥80% against *Alopecurus myosuroides, Echinocloa crus-galli* and *Lolium multiflorum*: I-a-3, I-a-10.

2. Herbicidal post-emergence action

Seeds of monocotylidonous and dicotylidonous weed and crop plants are placed in sandy loam in wood fibre pots, covered with soil and cultivated in a greenhouse under good growth conditions. Two to three weeks after sowing, the test plants are treated at the one-leaf stage. The test compounds, formulated as wettable powders (WP), are then with a water application rate of 600 l/ha (converted), with 0.2% of wetting agent added, sprayed onto the green parts of the plants in different amounts. After the test plants have been kept in the greenhouse under optimum growth conditions for about three weeks, the effect of the preparations is assessed visually in comparison to untreated controls (herbicidal effect in percent: 100% effect=the plants have died, 0% effect=like control plants).

In addition to the compounds mentioned above, the following compounds, applied by the pre-emergence method at 80 g/ha, show an effect of ≥80% against *Alopecurus myosuroides, Echinocloa crus-galli, Lolium multiflorum* and *Setaria viridis*: I-a-3, I-a-10, I-a-11.

Use of safeners:

If it is to be additionally tested as to whether safeners can improve the plant compatibility of test substances in the case of crop plants, the following options are used for applying the safeners:

Seeds of the crop plants are, before sowing, dressed with safener substance (the amount of safener stated in percent, based on the weight of the seed)

Before the application of the test substances, the crop plants are sprayed with the safener at a certain application rate per hectare (usually one day before the application of the test substances)

The safener is applied together with the test substance as a tank mix (the amount of safener stated in g/ha or as a ratio, based on the herbicide).

Container trials with cereals in the greenhouse

Mefenpyr 1 day prior to herbicide application

|  | Application rate g of a.i./ha | 10 days after application Summer barley observed (%) | 10 days after application Summer wheat observed (%) |
|---|---|---|---|
| Ex. (I-a-3) | 100 | 30 | 60 |
|  | 50 | 30 | 50 |
|  | 25 | 20 | 50 |
|  | 12.5 | 15 | 40 |
| Ex. (I-a-3) + mefenpyr | 100 + 50 | 20 | 30 |
|  | 50 + 50 | 15 | 15 |
|  | 25 + 50 | 10 | 15 |
|  | 12.5 + 50 | 5 | 5 |

The invention claimed is:

1. A method for controlling animal pests and/or unwanted vegetation, comprising applying to said pests, unwanted vegetation or their habitat at least one compound of formula (I)

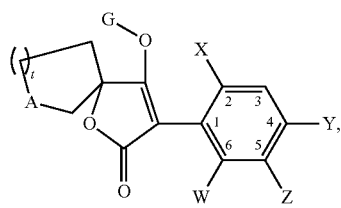

(I)

in which:

W represents hydrogen, halogen, alkyl, alkenyl, alkynyl, optionally substituted cycloalkyl, alkoxy, alkenyloxy, haloalkyl, haloalkoxy or cyano, X represents halogen, alkyl, alkenyl, alkynyl, optionally substituted cycloalkyl, alkoxy, alkenyloxy, alkylthio, alkylsulphinyl, alkylsulphonyl, haloalkyl, haloalkoxy, haloalkenyloxy, nitro or cyano, Y and Z independently of one another represent hydrogen alkyl, alkenyl, alkynyl, optionally substituted cycloalkyl, alkoxy, halogen, haloalkyl, haloalkoxy, cyano, nitro or in each case optionally substituted aryl or heteroaryl, A represents

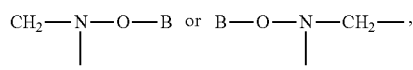

B represents hydrogen, alkyl, haloalkyl, alkoxylalkyl, alkoxylalkoxyalkyl, represents in each case optionally substituted alkenyl, alkynyl, represents cycloalkylalkyl which is optionally interrupted by heteroatoms, represents phenylalkyl, heteroarylalkyl or represents a latentiating group from G, t represents the number 0 or 1, G represents hydrogen (a) or represents one of the groups:

(b)

(c)

(d)

(e)

E, or (f)

(g)

in which:

E represents a metal ion or an ammonium ion,

L represents oxygen or sulphur,

M represents oxygen or sulphur, $R^1$ represents in each case optionally, halogen- or cyano-substituted alkyl, alkenyl, alkoxyalkyl, alkylthioalkyl or polyalkoxyalkyl, represents in each case optionally halogen-, alkyl- or alkoxy-substituted cycloalkyl or heterocyclyl, or represents in each case optionally substituted phenyl, phenylalkyl, heteroaryl, phenoxyalkyl or heteroaryloxyalkyl, $R^2$ represents in each case optionally halogen- or cyano-substituted alkyl, alkenyl, alkoxyalkyl or polyalkoxyalkyl, or represents in each case optionally substituted cycloalkyl, phenyl or benzyl, $R^3$, $R^4$ and $R^5$ independently of one another represent in each case optionally halogen-substituted alkyl, alkoxy, alkylamino, dialkylamino, alkylthio, alkenylthio or cycloalkylthio or represent in each case optionally substituted phenyl, benzyl, phenoxy or phenylthio, and $R^6$ and $R^7$ independently of one another represent hydrogen, in each case optionally halogen- or cyano-substituted alkyl, cycloalkyl, alkenyl, alkoxy, alkoxyalkyl, in each case optionally substituted phenyl or benzyl, or together with the nitrogen atom to which they are attached form an optionally substituted cycle which optionally contains oxygen or sulphur.

2. A composition, comprising an effective amount of an active compound combination comprising, (a') at least one compound of formula (I)

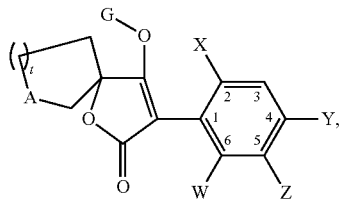

in which W, X, Y, Z, G, A and t have the meaning given above, and (b') at least one crop plant compatibility-improving compound selected from the group consisting of compounds: S1, S2, S3, S4, S5, S6, S7, S8, S9, S10, S11, S12, S13, and S14.

3. A method for controlling unwanted vegetation, comprising applying to said plants or their surroundings a composition according to claim 2.

4. A method for controlling unwanted vegetation, comprising applying at least one compound of formula (I)

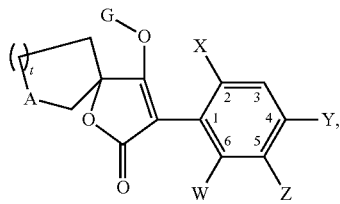

in which W, X, Y, Z, G, A and t have the meaning given above, and at least one crop plant compatibility-improving compound selected from the group consisting of compounds: S1, S2, S3, S4, S5, S6, S7, S8, S9, S10, S11, S12, S13, and S14, separately in close temporal succession to the plants or their surroundings.

5. A composition, comprising
at least one compound of formula (I)

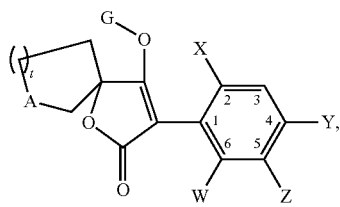

in which W, Y, Z, G, A and t have the meaning given above, or a composition according to claim 2, and
at least one salt of the formula (III')

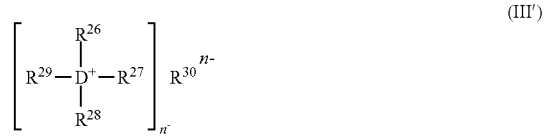

in which:
D represents nitrogen or phosphorus,
$R^{26}$, $R^{27}$, $R^{28}$ and $R^{29}$ independently of one another represent hydrogen or in each case optionally substituted $C_1$-$C_8$-alkyl or mono- or polyunsaturated, optionally substituted $C_1$-$C_8$-alkylene, wherein the substituents are selected from the group consisting of halogen, nitro and cyano,
n represents 1, 2, 3 or 4, and
$R^{30}$ represents an inorganic or organic anion.

6. The composition according to claim 5, farther comprises at least one penetrant.

7. A method for increasing the activity of pesticides and/or herbicides comprising an active compound of the formula (I)

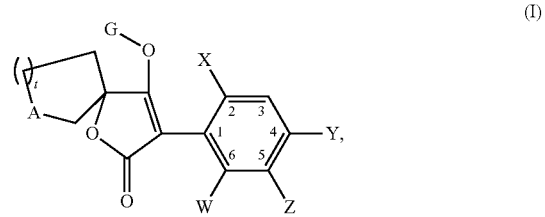

in which W, X, Y, Z, G, A and t have the meaning given above, or a composition according to claim 2, comprising preparing a ready-to-use composition using a salt of the formula (III')

in which:
D represents nitrogen or phosphorus,
$R^{26}$, $R^{27}$, $R^{28}$ and $R^{29}$ independently of one another represent hydrogen or in each case optionally substituted $C_1$-$C_8$alkyl or mono- or polyunsaturated, optionally substituted $C_1$-$C_8$-alkylene, wherein the substituents are selected from the group consisting of halogen, nitro and cyano,
n represents 1, 2, 3 or 4, and
$R^{30}$ represents an inorganic or organic anion.

8. The method according to claim 7, wherein said ready-to-use composition further comprises a penetrant.

* * * * *